(12) United States Patent
Wang et al.

(10) Patent No.: US 9,233,995 B2
(45) Date of Patent: Jan. 12, 2016

(54) QUINAZOLINE DERIVATIVES AND QUINAZOLINE COMPLEX PROTEIN KINASE INHIBITOR FOR INHIBITING MULTIPLICATION OF TUMOR CELLS AND PREPARATION METHOD THEREOF

(75) Inventors: Fuyi Wang, Beijing (CN); Qun Luo, Beijing (CN); Liyun Ji, Beijing (CN); Wei Zheng, Beijing (CN); Shuang Lv, Beijing (CN); Xianchan Li, Beijing (CN)

(73) Assignee: INSTITUTE OF CHEMISTRY, CHINESE ACADEMY OF SCIENCES (CN)

( * ) Notice: Subject to any disclaimer, the term of this patent is extended or adjusted under 35 U.S.C. 154(b) by 52 days.

(21) Appl. No.: 13/882,100

(22) PCT Filed: Oct. 27, 2011

(86) PCT No.: PCT/CN2011/081453
§ 371 (c)(1),
(2), (4) Date: Apr. 26, 2013

(87) PCT Pub. No.: WO2012/055369
PCT Pub. Date: May 3, 2012

(65) Prior Publication Data
US 2013/0225811 A1   Aug. 29, 2013

(30) Foreign Application Priority Data
Oct. 27, 2010   (CN) .......................... 2010 1 0521382

(51) Int. Cl.
*C07F 15/00* (2006.01)
*C07D 239/94* (2006.01)
*C07D 403/12* (2006.01)
*C07F 17/02* (2006.01)

(52) U.S. Cl.
CPC .......... *C07F 15/0053* (2013.01); *C07D 239/94* (2013.01); *C07D 403/12* (2013.01); *C07F 15/0046* (2013.01); *C07F 17/02* (2013.01)

(58) Field of Classification Search
CPC ................................ C07D 239/94; A61K 7/24
USPC ........................................ 514/266.2; 544/293
See application file for complete search history.

(56) References Cited

U.S. PATENT DOCUMENTS

2009/0111772 A1* 4/2009 Cai et al. .................. 514/58

FOREIGN PATENT DOCUMENTS

| CN | 1642552 | 7/2005 |
|---|---|---|
| CN | 1724521 | 1/2006 |
| CN | 1882567 | 12/2006 |
| CN | 101367793 | 2/2009 |
| CN | 101431894 A | 5/2009 |
| CN | 101535279 | 9/2009 |
| WO | 01/68652 | 9/2001 |
| WO | 2005/026150 | 3/2005 |
| WO | 2005097134 | 10/2005 |
| WO | 2005097137 | 3/2007 |
| WO | 2007023073 | 3/2007 |
| WO | 2007/084875 | 7/2007 |
| WO | 2009035718 | 3/2009 |

OTHER PUBLICATIONS

Xiong et al., "Discovery of 7-(4-3(Ethynylphenylamino)-7-methoxyquinazolin-6-yloxy)-N-hydroxyheptanamide (CUDC-101) as a Potent Multi-Acting HDAC, EGFR, and HER2 Inhibitor for the Treatment for Cancer," J. Med. Chem. (2010) 53:2000-2009.

(Continued)

*Primary Examiner* — Paul V Ward

(57) ABSTRACT

Quinazoline derivatives represented by general formula (1) and quinazoline complexes as protein kinase inhibitors, and their preparation methods are provided. Wherein, in general formula (1), at least one of R and R' is a group containing an atom capable of coordinating with noble metals, m and n are either the same or different and are integers from 0 to 5. Said quinazoline complex as protein kinase inhibitor is formed by coordination compound containing noble metal and said quinazoline derivative ligand capable of coordinating with noble metal in the coordination compound. Used as tyrosine protein kinase inhibitors, Quinazoline derivatives and quinazoline complexes as protein kinase inhibitors provided by the present invention have exhibited good inhibitory effect on proliferation of various tumor cells including human breast cancer cells line (drug-resistant) MCF-7/A, human breast cancer cell line (sensitive) MCF-7/S, prostate cancer cell PC-3, keratinocytes Colo-16, human non-small cell lung cancer cell line A549, etc.

38 Claims, 5 Drawing Sheets

(56) References Cited

OTHER PUBLICATIONS

Hennequin et al., "Design and Structure-Activity Relationship of a New Class of Potent VEGF Receptor Tyrosine Kinase Inhibitors," J. Med. Chem. (1999) 42:5369-5389.

Barker et al., "Studies Leading to the Identification of ZD1839 (Iressa TM): An orally Active, Selective Epidermal Growth Factor Receptor Tyrosine Kinase Inhibitor Targeted tot he Treatment of Cancer," Bioorganic & Medicinal Chemistry Letters (2001) 11:1911-1914.

* cited by examiner

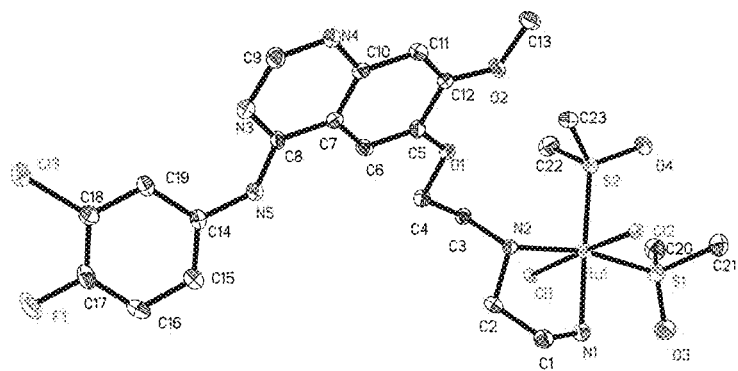
Fig. 1-a
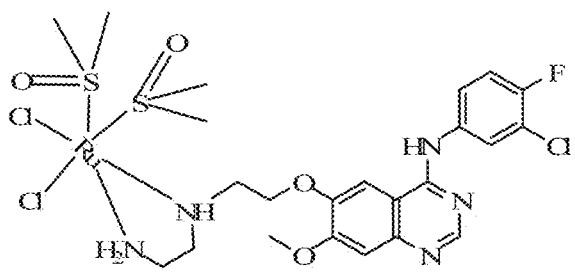
Fig. 1-b
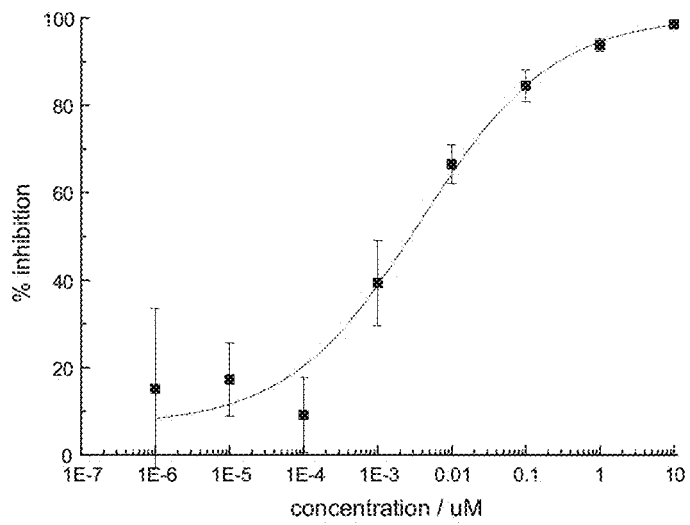
Fig. 2

QUINAZOLINE DERIVATIVES AND QUINAZOLINE COMPLEX PROTEIN KINASE INHIBITOR FOR INHIBITING MULTIPLICATION OF TUMOR CELLS AND PREPARATION METHOD THEREOF

This application is a 35 U.S.C. §371 national phase application of PCT/CN2011/081453, which was filed Oct. 27, 2011 and is incorporated herein by reference as if fully set forth.

TECHNICAL FIELD

The present invention relates to quinazoline derivatives and quinazoline complexes as protein kinase inhibitors, which inhibit tumor cell proliferation, and their preparation methods.

BACKGROUND ART

Anti-tumor chemical drugs used clinically include two major categories, cytotoxic drugs and molecular targeted drugs. Cytotoxic anti-tumor drugs (such as cisplatin, etc.) are all non-specific, while inhibiting and destructing abnormal proliferating tumor cells, they also cause inhibition and killing effect to other normal cells which proliferate rapidly. The side effects arising from this as well as congenital or acquired drug resistance of tumor cells to drugs have been a bottleneck restricting the clinical application of cytotoxic chemotherapy drugs. Over the past decade, highly selective molecular targeted therapeutic drugs against specific proliferation, differentiation and apoptosis mechanisms of tumor cell have developed rapidly. However, many small molecule compounds with good inhibitory activity on the protein kinases that are highly expressed in tumor cells may not be clinically used due to the poor water solubility or severe toxicity side effects, as well as easy to produce drug resistance.

SUMMARY OF THE INVENTION

The object of the present invention is to provide a quinazoline derivative and quinazoline complexes that have molecular targeting properties and are capable of acting as tyrosine protein kinase inhibitors as well as methods for their preparation. The structure of said quinazoline derivative contains potential metal coordination sites, which is capable of coordinating with cytotoxic metal antitumor compounds, so as to improve the water-solubility of tyrosine protein kinase inhibitor, as well as to reduce toxicity side effects of the cytotoxic drugs. This protein kinase inhibitor type such as quinazoline derivative not only have a good kinase inhibitory effect, but also exhibit good inhibition of tumor cell proliferation when coordinating with ruthenium, platinum, and other metals to produce quinazoline complexes. Moreover, in the presence of additional epidermal growth factor (EGF), most compounds have shown even better inhibitory activity on tumor cells (such as human breast cancer cell lines (sensitive) MCF-7/S) in which epidermal growth factor receptor (EGFR) is overexpressed, which indicates that EGFR (a protein tyrosine kinase) is one target of quinazoline derivative and quinazoline complexes as protein kinase inhibitors of the present invention inhibit tumor cell proliferation.

The present invention provides a quinazoline derivative, wherein the derivative has a molecule structure represented by general formula (1):

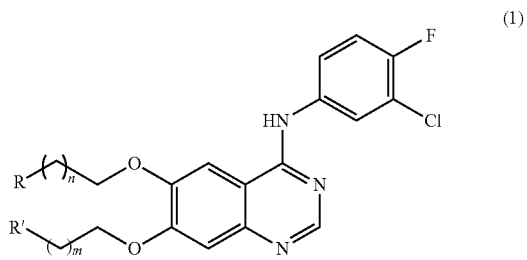

In the general formula (1), at least one of R and R' is a group containing an atom which is capable of coordinating with noble metals, m and n are either the same or different and are an integer from 0 to 5.

The present invention also provides preparation methods of the quinazoline derivative, wherein the method includes providing a first reactant A, said first reactant A is a compound shown by the formula (a), in which $R_{100}$ and $R_{101}$ are either the same or different, and are independently selected from hydrogen or methyl group, and wherein at least one is hydrogen; the method includes substituting hydrogen or methyl group at position $R_{100}$ in formula (a) with group shown by formula (Q1), and/or substituting hydrogen or methyl group at position $R_{101}$ in formula (a) with group shown by formula (Q2); at least one of R and R' is a group containing an atom which is capable of coordinating with noble metals, m and n are either the same or different and are an integer from 0 to 5;

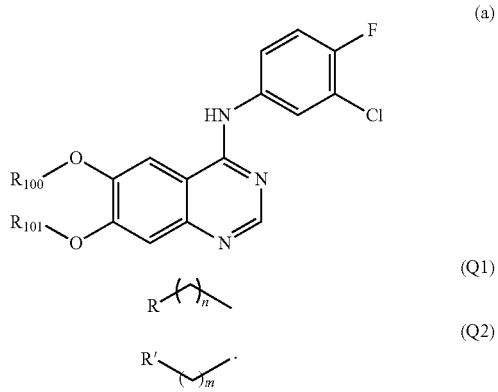

The present invention also provides a quinazoline complex as protein kinase inhibitor, said quinazoline complex is formed by coordination compound containing noble metal and ligand capable of substituting with noble metal in the coordination compound, wherein said ligand is the said quinazoline derivative provided by the present invention.

The present invention also provides a preparation method for quinazoline complex as protein kinase inhibitor, which comprises coordinating a compound containing noble metal with a ligand, said ligand is the quinazoline derivative prepared by method of the present invention. The quinazoline derivative of the present invention is classified as a tyrosine protein kinase inhibitor Iressa derivatives, which contain potential metal coordination sites in their structure and is capable of substituting one or more ligands in cytotoxic metal coordination complexes (such as organometallic complexes of ruthenium, cisplatin, etc.). And quinazoline derivative of the present invention, together with said cytotoxic metal ruthenium (II, III) and/or platinum, can form a quinazoline complex as a tyrosine protein kinase inhibitor, so that a number of protein kinase inhibitors, which have high activity but can not be used as the molecular targeted drugs due to poor water solubility, can again become a candidate compound. Furthermore, by the introduction of one or more molecule targeting drug units, the dose and frequency of using cytotoxic metal anticancer drugs are reduced, so the object of reducing the toxic side effect of single-targeted cytotoxic drugs is achieved. Moreover, the introduction of "single-molecule multi-target" action mechanism will help to decrease the possibility for the tumor cells to develop resistance to the drug.

What's more, using two in vitro analysis methods, inhibition of quinazoline derivative and quinazoline complex provided by the present invention on protein tyrosine kinase activity was examined and:

The results by enzyme-linked immunosorbent assay (ELISA) showed that: quinazoline derivative and quinazoline complex provided by the present invention exhibited good inhibitory activity on phosphorylation of EGFR.

Meanwhile, the results of experiments about the effects on the proliferation of tumor cells showed that: quinazoline derivatives and quinazoline complexes as tyrosine protein kinase inhibitors provided by the present invention exhibited good inhibitory effect on the proliferation of various tumor cells including human breast cancer cells line (drug-resistant) MCF-7/A, human breast cancer cell line (sensitive) MCF-7/S, prostate cancer cell PC-3, keratinocytes Colo-16, human non-small cell lung cancer cell line A549, etc. Moreover, in the presence of additional EGF, quinazoline derivatives and quinazoline complexes provided by the present invention as tyrosine protein kinase inhibitors exhibited higher inhibitory effect on the proliferation of tumor cells in which epidermal growth factor receptor (EGFR) overexpresses (such as human breast cancer cell lines (sensitive) MCF-7/S).

BRIEF DESCRIPTION OF DRAWINGS

FIG. 1-*a* is the X-ray diffraction crystal structure of compound No. JLY2009, and FIG. 1-*b* is the corresponding general formula;

FIG. 2 is the graph of reference compound No. LQ1001 measured under the condition of ELISA showing $IC_{50}$=4 nM;

DESCRIPTIONS OF THE PREFERRED EMBODIMENTS

Figure 3:
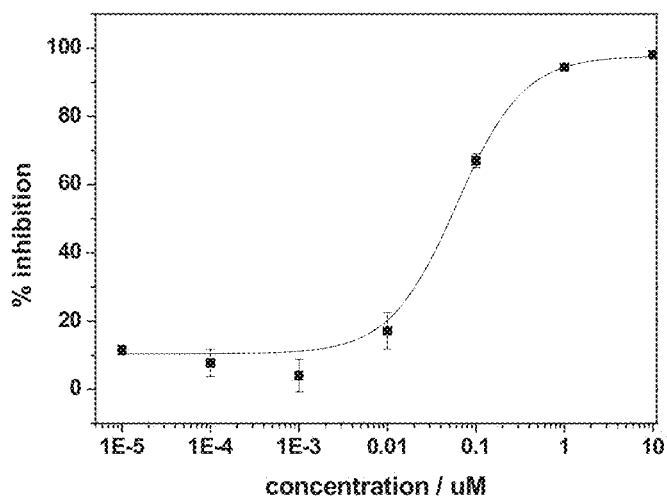
FIG. 3 is the graph of compound No. JLY1002 measured under the condition of ELISA showing $IC_{50}$=60.2 nM.

According to the present invention, a quinazoline derivative is provided, wherein the derivative has a molecular structure represented by the general formula (1):

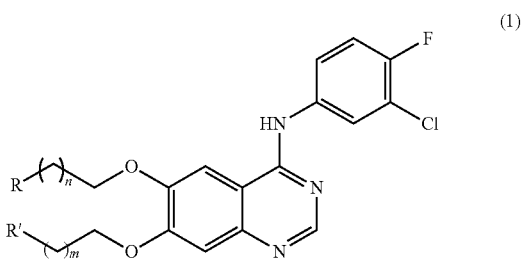

In general formula (1), at least one of R and R' is a group containing an atom which is capable of coordinating with noble metals, m and n are either the same or different and are integers from 0 to 5.

Wherein, at least one of R and/or R' is a group containing atom which is capable of coordinating with noble metal. For example, said atom in R and/or R' may be one or more from an oxygen atom, a nitrogen atom and a sulfur atom. Preferably, said atom in R and/or R' is an oxygen atom and/or nitrogen atom, said oxygen atom may be oxygen atom in hydroxyl, and said nitrogen atom may be nitrogen atom from amine group or nitrogen atom from aromatic heterocycle. Specifically, said amine group may be an aliphatic amine, said aromatic heterocycle may be one selected from imidazole ring, pyridine ring, 2,2'-bipyridine ring, phenanthroline ring, and 8-hydroxy quinoline ring. The number of atoms which can coordinate with noble metal in R and/or R' can be appropriately selected according to the requirement of coordination, and it may usually be 1-3.

According to the present invention, said noble metal can often be ruthenium and/or platinum and the like.

According to the present invention, in formula (1), said R and R' with a coordination function may be various groups that can form coordination complexes with metal, especially cytotoxic metal ruthenium.

Preferably, according to one embodiment of the present invention, m is 0, R' is hydrogen, and said group R with coordination function is any one selected from fused heterocyclic imino or substituted fused heterocyclic imino, aminoalkyl imino, group having on the ring a tertiary amino group and imidazole type five-membered heterocyclic structure, six-membered aromatic heterocyclic imino or substituted six-membered aromatic heterocyclic imino, and nitrogen in said imino or tertiary amino group bonds to the 6-oxygen of the alkyl chain. That is to say, nitrogen from the imino of fused heterocyclic imino or substituted fused heterocyclic imino, six-membered aromatic heterocyclic imino or substituted six-membered aromatic heterocyclic imino is used to bond to the 6-oxygen of the alkyl chain, and at least one of nitrogen atom, oxygen atom and sulfur atom on the ring is capable of coordinating with noble metal; nitrogen on the imino of aminoalkyl imino is used to bond to the 6-oxygen of the alkyl chain, and nitrogen on both amino and imino is capable of coordinating with noble metal; nitrogen on the tertiary amino group of the group having on the ring a tertiary amino group and imidazole type five-membered heterocyclic structure bound to the 6-oxygen of the alkyl chain, and at least one of other nitrogen atom, oxygen atom and sulfur atom on the imidazole type five-membered heterocyclic structure is capable of coordinating with noble metal.

Specifically, the fused heterocyclic imino or substituted fused heterocyclic imino has the structure shown by any one of general formula (2)-(7):

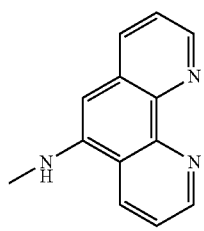
(2)

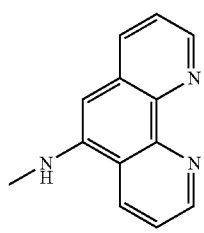
(3)

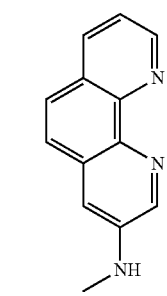
(4)

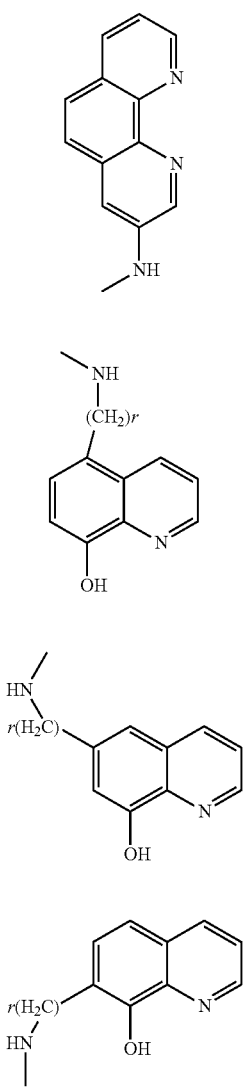

Wherein, in the above mentioned formula (5)-(7), each n may be an integer from 0 to 3. Preferably, said fused heterocyclic imino or substituted fused heterocyclic imino has the structure shown by any one of general formula (2) and (16):

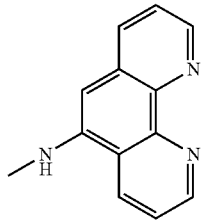
(2)

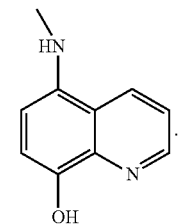
(16)

Said aminoalkyl imino has the structure shown by general formula (8):

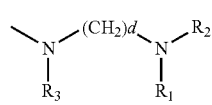
(8)

Wherein, in formula (8), d is an integer from 2 to 5, $R_1$, $R_2$ and $R_3$ are independently selected from the group consisting of hydrogen atom and C1-C3 alkyl groups. More preferably, said aminoalkyl imino has the structure shown by general formula (17):

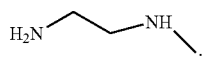
(17)

Said group having on the ring a tertiary amino group and imidazole type five-membered heterocyclic structure has the structure shown by general formula (9):

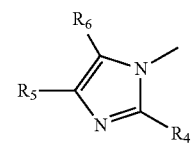
(9)

Wherein, in formula (9), $R_4$, $R_5$ and $R_6$ are independently selected from the group consisting of hydrogen atom and C1-C3 alkyl groups. Preferably, said group having on the ring a tertiary amino group and imidazole type five-membered heterocyclic structure has the structure shown by general formula (18):

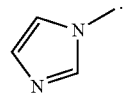
(18)

Said six-membered aromatic heterocyclic imino or substituted six-membered aromatic heterocyclic imino has the structure shown by general formula (10)-(14):

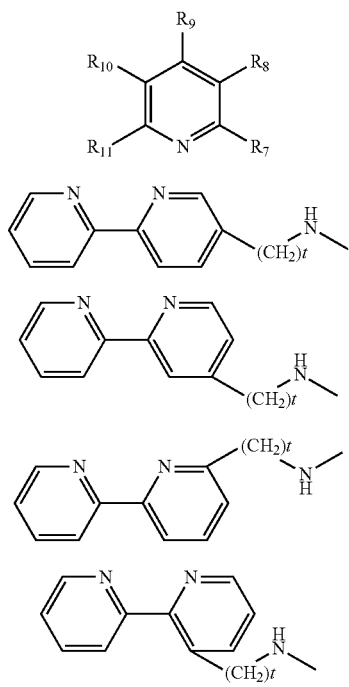

(10)

(11)

(12)

(13)

(14)

Wherein, in general formula (10), $R_7$, $R_8$, $R_9$, $R_{10}$ and $R_{11}$ are independently any one of hydrogen atom, imino and C1-C3 alkyl group, and at least one of $R_7$, $R_8$, $R_9$, $R_{10}$ and $R_{11}$ is an imino; in formula (11)-(14), each t is an integer from 0 to 3. Preferably, said six-membered aromatic heterocyclic imino or substituted six-membered aromatic heterocyclic imino may be represented by any one of the general formula (19)-(20) as described below:

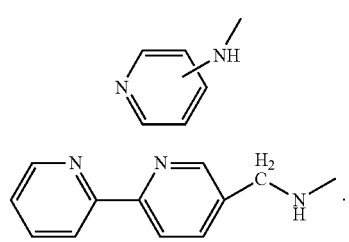

(19)

(20)

Wherein, in general formula (19), the amino may be located on para, meta or ortho-position to pyridine nitrogen, such as the following general formulae:

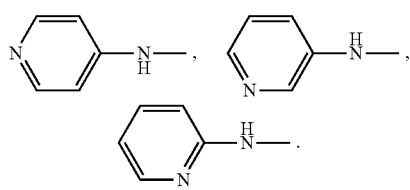

According to the present invention, said preparing method of quinazoline derivative includes providing the first reactant A represented by formula (a), in which $R_{100}$ and $R_{101}$ are either the same or different, independently selected from hydrogen atom or methyl group, and at least one of them is hydrogen; the method includes substituting hydrogen atom or methyl group at position $R_{100}$ in formula (a) with group shown by formula (Q1), and/or substituting hydrogen or methyl group at position $R_{101}$ in formula (a) with group shown by formula (Q2); at least one of R and R' is a group containing an atom capable of coordinating with noble metal, m and n are either the same or different and are integers from 0 to 5;

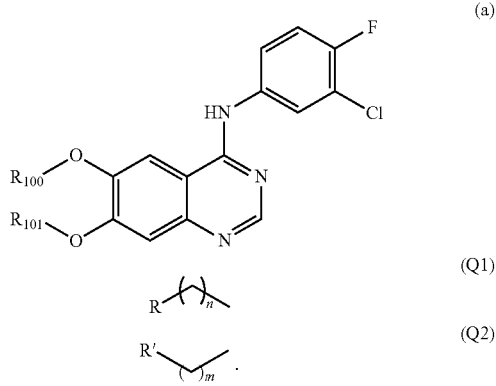

(a)

(Q1)

(Q2)

Wherein, the atoms capable of coordinating with the noble metal in R and/or R' are the same as what defined above.

When m is 0, R' is hydrogen atom and R is a group having coordination function, according to preparing method for protein tyrosine kinase provided by the present invention, in means (I), said first organic amine is any one selected from the group consisting of alkyl diamine or substituted alkyl diamines, compound having on the ring a tertiary amino group and imidazole type five-membered heterocyclic structure; in means (II), said second organic amine is any one selected from the group consisting of fused heterocyclic group-substituted amine or substituted fused heterocyclic substituted amine and six-membered aromatic heterocyclic group-substituted amine or substituted six-membered aromatic heterocyclic substituted amine.

Preferably, said fused heterocyclic group-substituted amine or substituted fused heterocyclic substituted amine is represented by general formula (21)-(26), said compound having on the ring a tertiary amino group and imidazole type five-membered heterocyclic structure is represented by general formula (27), six-membered aromatic heterocyclic group-substituted amine or substituted six-membered aromatic heterocyclic substituted amine is represented by general formula (28)-(32), and the alkyl diamine or substituted alkyl diamine is represented by formula (33):

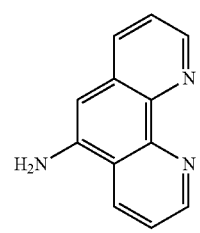

(21)

(22) 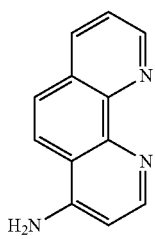

(23) 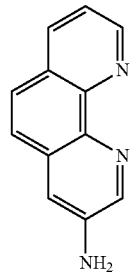

(24) 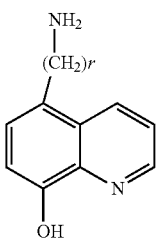

(25) 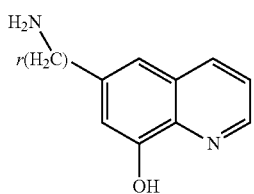

(26) 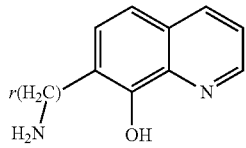

(27) 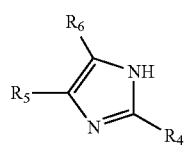

(28) 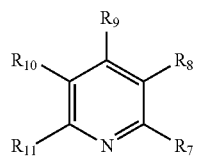

(29) 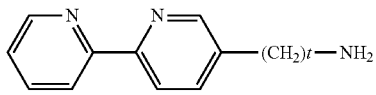

(30) 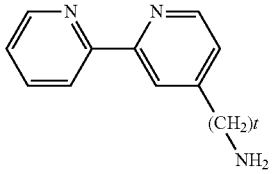

(31) 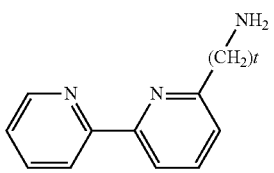

(32) 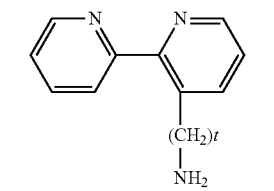

(33) 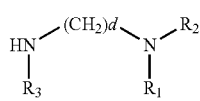

Wherein, in general formula (24)-(26), r can each be an integer from 0 to 3; in formula (27), $R_4$, $R_5$ and $R_6$ may be any one independently selected from the group consisting of hydrogen atoms and C1-C3 alkyl groups; in general formula (28), $R_7$, $R_8$, $R_9$, $R_{10}$ and $R_{11}$ may be each independently any one of hydrogen atom, imino and C1-C3 alkyl groups, and at least one group of $R_7$, $R_8$, $R_9$, $R_{10}$ and $R_{11}$ is a amine group; in general formula (29)-(32), t can each be an integer from 0 to 3; and in general formula (33), d may be an integer from 2 to 5, $R_1$, $R_2$ and $R_3$ may be each independently selected from the group consisting of hydrogen atoms and C1-C3 alkyl groups.

Preferably, said first organic amine is any compound as shown in formula (34) to (35); said second organic amine is any compound as shown in formula (21), (37) to (39):

(34) 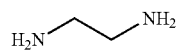

(35) 

(21) 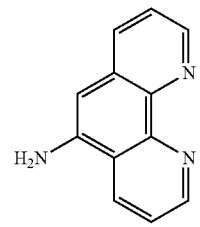

-continued

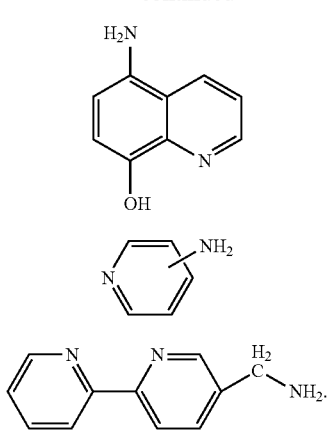

(37)

(38)

(39)

That is to say, said compound represented by formula (33) in the first organic amine is preferably compound as shown in general formula (34), said compound represented by formula (27) in first organic amine is preferably compound as shown in general formula (35), said compound represented by formula (24) in the second organic amine is preferably compound as shown in general formula (37), said compound represented by formula (28) in the second organic amine is preferably compound as shown in general formula (38), said compound represented by formula (29) in the second organic amine is preferably compound as shown in general formula (39).

According to the method provided in the present invention, both said first organic amine and second organic amine are commercially available, and may also be obtained in accordance with the various conventional preparation methods.

According to the method provided by the present invention, $R_{100}$ is hydrogen, $R_{101}$ is methyl, methods to substitute hydrogen in formula (a) with group shown in formula (Q1) include means (I) and means (II):

According to the present invention, the means (I) includes:
(1) In the presence of a first organic solvent, allow the first reactant A to contact and react with dihaloalkane to produce the intermediate product B, said dihaloalkane is represented by the formula (k) below, said intermediate product B is represented by the formula (b) below, wherein, X, $X_1$, $X_2$ all represent halogen atom;

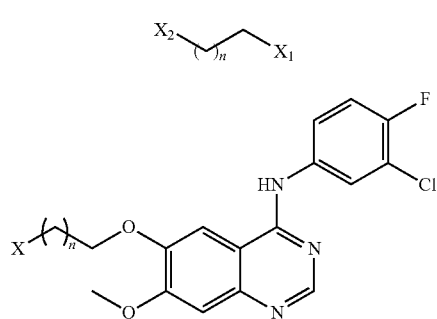

(k)

(b)

(2) In the presence of a second organic solvent and under condensation reaction conditions, intermediate product B obtained in step (1) is heated with a first organic amine containing atom capable of coordinating with noble metal to reflux. The condensation reaction conditions allow halogen atom of 6-haloalkoxy in intermediate product B to undergo condensation reaction with said first organic amine.

In means (I):
In step (1), the conditions allowing the first reactant A to contact and react with dihaloalkane may include reaction temperature and time, and said reaction temperature can be selected within a wide temperature range; preferably, the reaction temperature may be 50-100° C., more preferably 70-90° C. Longer reaction time is beneficial for improving the conversion rate of reactant or the yield of reaction product, but if the reaction time is too long, further improvement of the conversion rate of reactant or the yield of reaction product is not obvious. Therefore, generally, the reaction time may be 1-10 hours, more preferably 2-6 hours.

Molar ratio of said first reactant A to dihaloalkane may be 1:(3-8), preferably 1:(3-4.5).

To further promote the reaction to the positive direction, in step (1), the contacting and reaction between the first reactant A and dihaloalkane is preferably performed in the presence of acid binding agent. The amount of said acid binding agent used may vary in a wide range, as long as it can further promote the reaction between the first reactant A and dihaloalkane toward the positive direction, preferably, molar ratio of said acid binding agent to the first reactant A is (3-8):1.

Said alkylhalide may be one or more selected from the group consisting of dihalo ethane, dihalo propane, dihalo butane and dihalo pentane; specifically, said alkylhalide may be one or more selected from the group consisting of dibromoethane, dibromopropane, dibromobutane and dibromopentane.

In step (2), the conditions allowing the intermediate product B obtained in step (1) to be heated with a first organic amine to reflux may include heating reflux temperature and time, said temperature is usually 50-95° C.; the time usually ranges from 1-10 hours, preferably 2-6 hours. The molar ratio of said intermediate product B to the first organic amine may be 1:(1-10), preferably 1:(1-8).

To further promote the reaction to the positive direction, in step (2), heated reflux of the intermediate product B and the first organic amine is preferably performed in the presence of acid binding agent, and amount of said acid binding agent used may vary in a wide range, as long as it can further promote heated reflux of the intermediate product B and the first organic amine toward the positive direction, preferably, molar ratio of said acid binding agent to the first organic amine is (3-8):1.

For the said condensation reaction conditions, it can be any one as long as they allow halogen atom of 6-haloalkoxy in intermediate product B to undergo condensation reaction with amino or imino in compound containing group with coordinating function.

When the first organic amine is a compound represented by general formula (33), particularly by general formula (34), as long as under the heated reflux conditions, its condensation reaction with said intermediate product is guaranteed. When said first organic amine is compound represented by general formula (27), particularly by general formula (35), said condensation reaction conditions also include the presence of catalyst, in order to further promote the reaction. Said catalyst may be a variety of alkalis and a phase transfer catalyst, for example, one or more catalysts including KI and $(C_4H_9)_4$NBr.

Said first organic solvent and the second organic solvents may be one or more independently selected from the group consisting of N,N-dimethyl formamide (DMF) and acetonitrile. On the basis that the total amount of the first reactant and dihaloalkane is 1000 mg, the amount of said first organic solvent used may be 4-20 mL. On the basis that the total amount of the intermediate product and the second reactant is 1000 mg, the amount of the second organic solvent used may be 10-60 mL.

The type of said acid binding agent can be various conventional acid binding agents well known to those skilled in the art; for example, said acid binding agent may be one or more selected from the group consisting of $K_2CO_3$, $CsCO_3$, NaOH and triethylamine.

According to the present invention, means (II) comprises:

(1) in the presence of a first organic solvent, the first reactant A is allowed to contact and react with a halogenated carboxylic ester, so as to generate the intermediate product C. Said halogenated carboxylic ester is represented by the following formula (1), said intermediate product C is represented by the following formula (c), wherein, X represents a halogen atom;

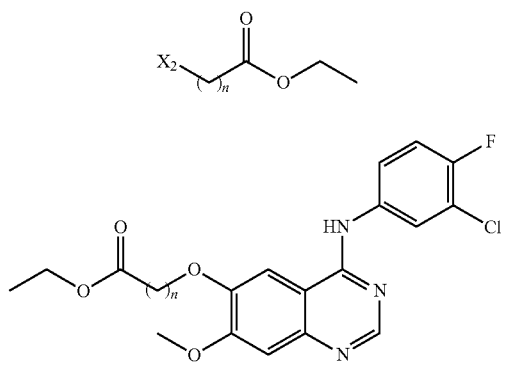

(2) under catalyzing by alkali, the intermediate product C obtained in step (1) is hydrolyzed, to obtain the intermediate D as shown in the following formula (d); the intermediate product D is allowed to undergo halogenation reaction to obtain an intermediate product E as shown in the formula (e) below; said intermediate product E is allowed to contact and react with a second organic amine which is a compound containing group with coordinating function under conditions allowing halogen atom in 6-alkoxy acyl halide of the intermediate product E to undergo condensation reaction with the second organic amine, so as to obtain condensation product F as shown in the following formula (f);

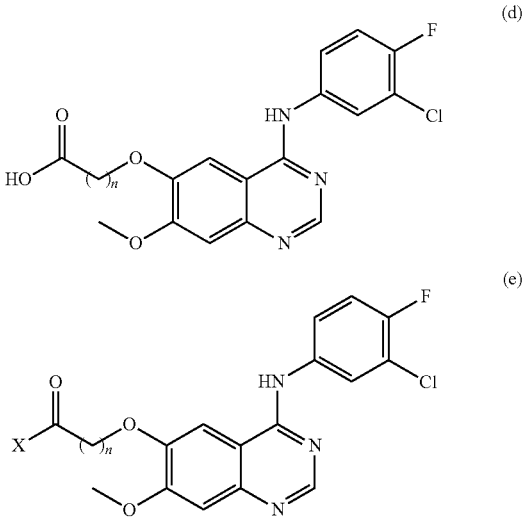

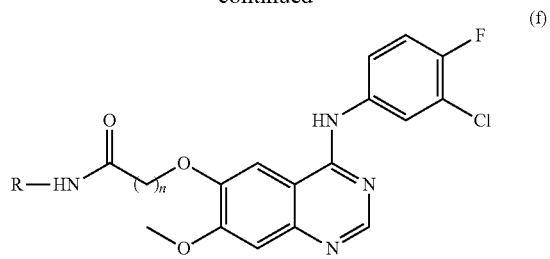

(3) Carbonyl group of 6-alkoxy amide in the condensation product F obtained in step (2) is reduced to alkylene group;

According to the method provided by the present invention, in means (II):

In step (1), conditions allowing the first reactant A to contact and react with halogenated carboxylic ester include reaction temperature and time, for said reaction temperature, it may be selected from a wide temperature range, preferably, the reaction temperature may be 10-60° C., preferably 20-50° C. Longer reaction time is beneficial for improving the conversion rate of reactant or the yield of reaction product, but if the reaction time is too long, further improvement of the conversion rate of reactant or the yield of reaction product is not obvious. Therefore, generally, the reaction time may be 0.3-5 hours, more preferably 0.5-4 hours.

The molar ratio of said first reactant to halogenated carboxylic ester may be 1:(1-1.5), preferably 1:(1-1.1).

In order to further promote the reaction to the positive direction, in step (1), the contacting and reaction between the first reactant and halogenated carboxylic ester is preferably performed in the presence of acid binding agent. The amount of said acid binding agent used may vary in a wide range, as long as it can further promote the reaction between the first reactant and halogenated carboxylic ester toward the positive direction, preferably, molar ratio of said acid binding agent to the first reactant A is (2-5):1.

According to the present invention, said halogenated carboxylic ester may be one or more selected from the group consisting of halogenated ethyl acetate, halogenated methyl acetate and halogenated ethyl pyruvate. Specifically, said halogenated carboxylic ester may be one or more selected from the group consisting of ethyl acetate bromide, methyl acetate bromide and ethyl pyruvate bromide.

On the basis that the total amount of the first reactant and halogenated carboxylic ester is 1000 mg, the amount of said first organic solvent used is usually 10-20 mL.

In step (2), catalyzed by alkali, the hydrolysis conditions of intermediate product C obtained in step (1) may be conventional conditions used in hydrolyzing ester to acid. For example, the hydrolysis temperature may be 20-60° C., preferably 25-40° C.; the hydrolysis time may be 1-15 hours, preferably 2-6 hours. Said alkali may generally be one or more selected from the group consisting of NaOH, LiOH and KOH, and the amount of said alkali used may generally be 3-5 times of the molar amount of the intermediate product C. Usually the hydrolysis reaction is carried out in the presence of a mixed solvent, such as a mixed solution of water-methanol-tetrahydrofuran. On the basis that the total amount of the reactant is 1000 mg, the total amount of said mixed solvent is 60-150 ml. And the volume ratio of the mixed solvent may be is 1:(1-2):(2-4).

In step (2), the method for halogenation reaction of the intermediate product D comprises allowing intermediate product D to contact and react with thionyl chloride, said contacting and reaction conditions generally include that the reaction temperature is 25-75° C., the reaction time 1-5 hours, and the amount of thionyl chloride used 5-15 times of the molar amount of the intermediate product D (4-(3'-chloro-4'-fluoro-phenylamino)-6-alkoxy carboxylic-7-methoxy quinazoline). In order to facilitate the dissolution of the hydrolyzate, said reaction is preferably conducted in the presence of a first organic solvent, the amount of which can be determined according to the dissolution status of the hydrolyzate. More preferably, in the step of halogenating the intermediate product D, in order to further promote the reaction to the positive direction, said reaction is also carried out in the presence of acid binding agent, preferably pyridine, and the amount of pyridine used may be 1-3 drops (about 0.5-2 mmol).

The contacting and reaction of the intermediate product E, which is obtained by contacting and reaction of the intermediate product D with thionyl chloride, with the second organic amine is preferably carried out in the presence of a third organic solvent; the contact reaction conditions include that, reaction temperature may be 3-30° C., the reaction time 2-8 hours, and molar ratio of said intermediate product E and the second organic amine 1:(1-2), preferably 1:(1.1-1.5). Said third organic solvent may be selected from methylene chloride ($CH_2Cl_2$) and/or chloroform. On the basis that the total amount of the intermediate E and the second organic amine is 1000 mg, the amount of said third organic solvent used is 30-60 ml.

In the step (3), the method, by which the carbonyl group in 6-alkoxy amide of the condensation product F obtained in step (2) is reduced in the presence of a fourth organic solvent, comprises heating the sodium borohydride together with the condensation product F to reflux; conditions of refluxing typically include a temperature of 40-60° C. and time of 6-20 hours, and the amount of sodium borohydride used may be 2-4 times of the molar amount of the condensation product F. Said fourth organic solvent may be selected from THF and/or dioxane. And on the basis that the total amount of the sodium borohydride and the condensation product of F is 1000 mg, the amount of the fourth organic solvent is 50-80 ml. In addition, said reduction reaction is preferably carried out in an acidic environment. For example, trifluoro acetic acid (TFA) was added to the reaction system in an inert atmosphere, in order to promote the reaction to go forward (the amount of trifluoroacetic acid used may be 1-3 drops (about 0.5-2 mmol)). Said inert atmosphere may be any inert atmosphere that will not react with reactants or reaction product, e.g., at least one of nitrogen and group 0 gases in the periodic table. And said inert atmosphere may be either flowing atmosphere or static atmosphere.

According to method provided by the present invention, in order to further promote the reaction to the positive direction, the contacting and reaction between the first reactant A and halogenated carboxylic ester as well as the contacting and reaction between intermediate product E and the second organic amine are preferably performed in the presence of acid binding agent, the molar ratio of said acid binding agent to the first reactant A is (2-5):1, and the molar ratio of said acid binding agent to intermediate product E is (2-5):1. The type of said acid binding agent is described above.

According to the method provided by the present invention, when $R_{100}$ is hydrogen and $R_{101}$ is methyl, the method to substitute hydrogen at $R_{100}$ position of formula (a) by the group shown by formula (Q1) and substitute methyl at $R_{101}$ position of formula (a) by the group shown by formula (Q2) comprises:

(1) under the protection of inert gas, allow the first reactant A to contact and react with molten pyridine hydrochloride, to produce intermediate product H which is a compound represented by the following formula (h);

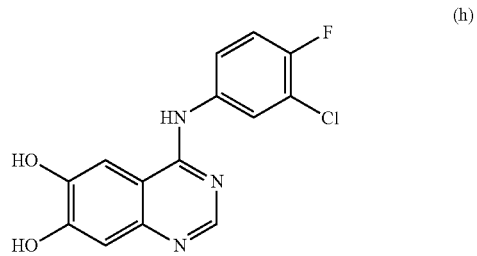 [SMILES: Oc1cc2ncnc(Nc3ccc(F)c(Cl)c3)c2cc1O]

(2) in the presence of the first organic solvent, the intermediate product H obtained in the step (1) is allowed to contact and react with halogenated fatty alcohol to obtain an intermediate product I which is a compound represented by the following formula (1); the intermediate product I undergo halogenation reaction, so as to obtain intermediate product J which is a compound shown by the following formula (j) and the intermediate product J is allowed to undergo ammonolysis reaction with ammonia, wherein $X_1$ and $X_2$ are halogen atom;

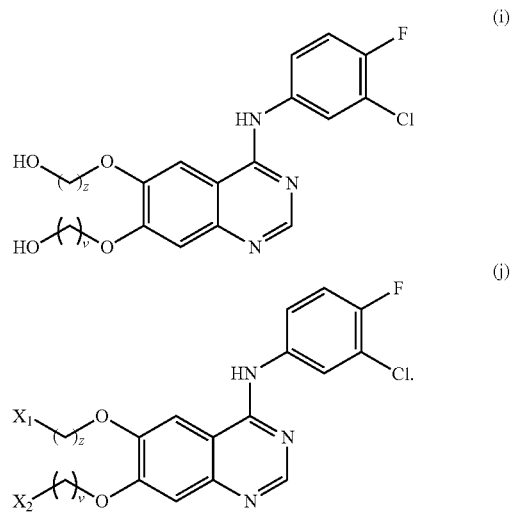

wherein, in step (1), the conditions allow first reactant A to contact and react with molten pyridine hydrochloride include reaction temperature and time, and the reaction temperature may be 150-185° C., the reaction time may be 2-5 hours.

Said inert atmosphere may be any inert atmosphere which does not react with the reactants or product, e.g., at least one of nitrogen and group 0 gases in the periodic table, and said inert atmosphere may be either flowing atmosphere or static atmosphere.

In step (1), molar ratio of said first reactant A to molten pyridine hydrochloride may be 1:(15-25).

In step (2), conditions that allow the intermediate product H obtained in step (1) to contact and react with a halogenated fatty alcohol may include that the reaction temperature is 40-60° C., and the reaction time is 5-15 hours. Molar ratio of said intermediate product H to halogenated fatty alcohols may be 1:(3-8). Number of carbon atoms of said halogenated fatty alcohol may be 1-5, for example, said halogenated fatty alcohol may be one or more selected from the group consisting of 2-halogenated ethanol, 3-halogenated propanol and 4-halogenated butanol, specifically, it may be one or more selected from the group consisting of 2-bromoethanol, 3-bromopropanol and 4-bromobutanol.

In the step (2), methods to allow intermediate product I to undergo halogenation reaction include, contacting and reacting of the intermediate D with the phosphorus trihalide in the presence of a fifth organic solvent. The contact reaction conditions include reaction temperature and time, and said reaction temperature may be 90-110° C., said reaction time may be 1-10 hours; the molar ratio of intermediate D and phosphorus trihalide may be 1:(1.2-2.5).

Said fifth organic solvents may be one or more selected from the group consisting of chlorobenzene, pyridine and N,N-dimethyl formamide. On the basis that the total amount of the intermediate product D and phosphorus trihalide is 1000 mg, amount of said fifth organic solvent may be 20-80 ml.

In order to further promote the reaction to the positive direction, halogenation reaction that intermediate product I undergoes is carried out in the presence of acid binding agent, preferably pyridine. And the molar amount of said acid binding agent used is 3-8 times of intermediate product I.

In the step (2), methods to carry out ammonolysis between intermediate product J and ammonia comprises allowing intermediate product J to contact and react with ammonia in the presence of a sixth organic solvents, and the molar ratio of intermediate product J to ammonia may be 1:(10-30).

Conditions that allow intermediate J to contact and react with ammonia so as to carry out ammonolysis typically include reaction temperature and reaction time, wherein said reaction temperature may be 25-50° C., and the reaction time may be 5-15 hours.

Said sixth organic solvent may be one or more selected from the group consisting of methanol, ethanol and isopropanol. And on the basis that the amount of intermediate J is 1000 mg, the amount of said sixth organic solvent used may be 20-50 ml.

In order to improve the purity of the final product, the method also includes separation and purification steps to separate and purify said intermediate products, and said separation and purification methods may use conventional separation and purification methods in the art, for example, said separation method includes filtering, centrifugation, extraction, etc.; said purification method includes column chromatographic separation, recrystallization, etc. Specific operating conditions and methods thereof are well known by all those skilled in the art, so they are omitted here.

In organic synthesis process, some of the conventional operations, such as removing the solvent, washing and drying methods, can all be performed using conventional operation methods, for example, method for solvent removal may be vacuum distillation method. Washing method may be carried out with water, isopropanol, diethyl ether, etc., to remove some unreacted raw materials. Drying method and conditions are well known to those skilled in the art, for example, said drying temperature may be 40-80° C., preferably 50-60° C.; drying duration may be 2-12 hours, preferably 5-8 hours.

According to the present invention, said quinazoline complex as protein kinase inhibitor is formed of coordination compound containing noble metal and ligand being capable of coordinating with the noble metal in the coordination compound, wherein said ligand is said quinazoline derivative provided by present invention.

According to the present invention, said quinazoline complex as protein kinase inhibitor may be represented by the following four general formulae, respectively, namely:

According to a particular embodiment of the present invention, said quinazoline complex as protein kinase inhibitor is represented by AG(X'Y')Z:

X'Y' is group formed by quinazoline derivative shown by the general formula (1) in Claim 1, wherein, m is 0, R' is hydrogen, R is fused heterocyclic imino or substituted fused heterocyclic imino represented by any one of general formula (5)-(7) in Claim 8; and nitrogen of said imino bonds to the 6-oxygen of the alkyl chain in general formula (1); nitrogen on said fused heterocyclic ring and oxygen in hydroxyl group coordinate with G; and preferably, R is structure shown by formula (16) in claim 9;

wherein, Z may be a group selected from the group consisting of halogen, —SCN, —N$_3$, and —CN;

A may be any one selected from benzene, biphenyl, isopropyl toluene and benzo-cyclane; B is Cl$^-$, PF$_6^-$ or BF$_4^-$; and G is preferably ruthenium.

Specifically, X'Y', i.e. group formed by quinazoline derivative represented by formula (1), may be a group shown by the following general formulae:

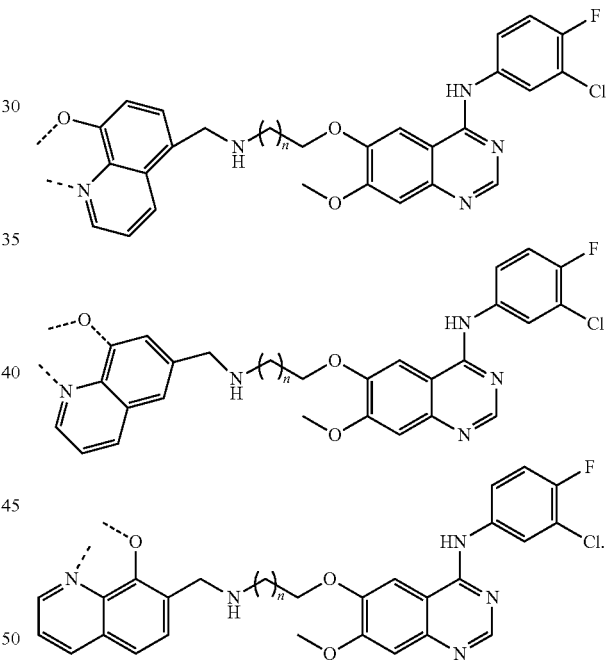

According to another particular embodiment of the present invention, said quinazoline complex as protein kinase inhibitor may also be represented by general formula [AG(XY)Z]$^+$ B$^-$:

XY is a group formed by the quinazoline derivative represented by general formula (1) in Claim 1, wherein, m is 0, R' is hydrogen, R is any one of fused heterocyclic imino or substituted fused heterocyclic imino represented by the general formula (2)-(4) and aminoalkyl imino represented by general formula (8) as well as six-membered aromatic heterocyclic imino or substituted six-membered aromatic heterocyclic imino represented by general formula (11)-(14) in Claim 8, and nitrogen on said imino bonds to the 6-oxygen of the alkyl chain where 6-oxygen exists in general formula (1); wherein, these two nitrogen atoms in said fused heterocycle can coordinate with G, or these two nitrogen atoms on said aminoalkyl imino can coordinate with G, or these two nitrogen atoms on the said six-membered aromatic heterocycle can coordinate with G. Preferably, R is structure represented by formula (2), formula (17), or formula (20) in Claim 9;

alternatively, R and R' are —NH$_2$; n is an integer from 1 to 3, and m is an integer from 1 to 3, wherein, nitrogen on R and R' can coordinate with G;

wherein, Z can be a group selected from the group consisting of halogen, —SCN, —N$_3$ and —CN;

A can be one selected from the group consisting of benzene, biphenyl, isopropyl toluene and benzo-cyclane; B is Cl$^-$, PF$_6^-$ or BF$_4^-$; and G is preferably ruthenium.

Specifically, XY, i.e. group formed by quinazoline derivative represented by formula (1), may be a group shown by the following general formulae:

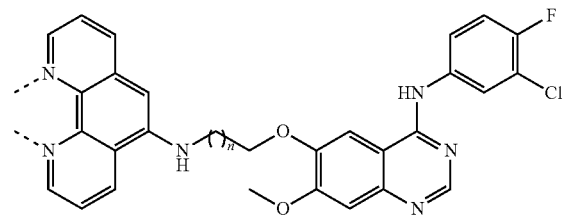

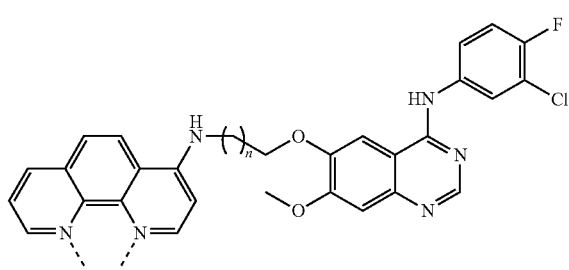

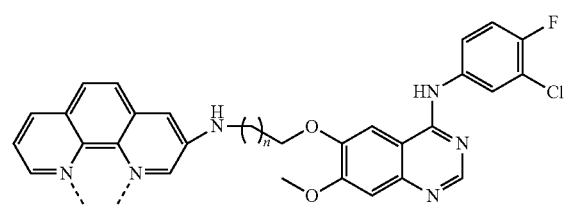

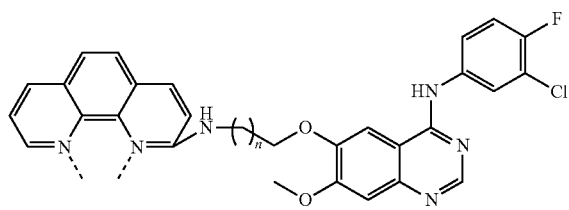

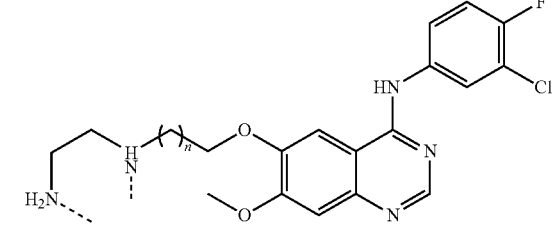

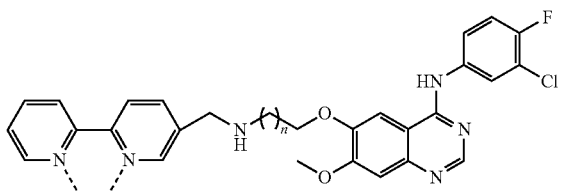

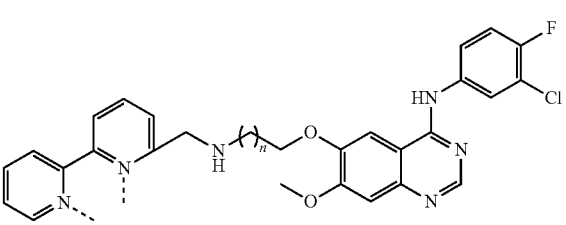

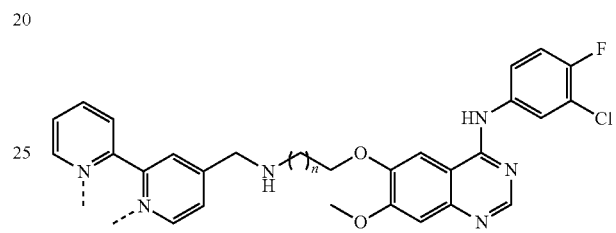

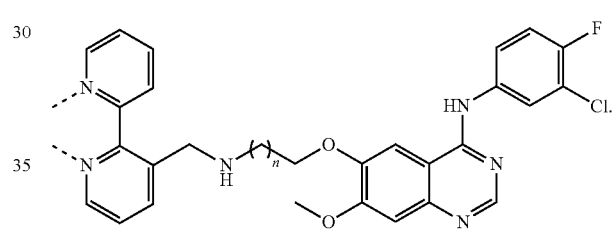

According to another particular embodiment of the present invention, said quinazoline complex as protein kinase inhibitors may also be represented by general formula [AG(X1Y1)Z1]$^+$B$^-$: X1Y1 is an alkyl diamine group of 1-5 carbon atoms, Z1 is a group formed by quinazoline derivative represented by formula (1) in Claim 1, wherein, m is 0, R' is hydrogen, R is any one of group having on the ring a tertiary amino group and imidazole type five-membered heterocyclic structure represented by general formula (9) and six-membered aromatic heterocyclic imino or substituted six-membered aromatic heterocyclic imino represented by general formula (10) in Claim 8, and nitrogen on said imino or tertiary amino group bonds to the 6-oxygen of the alkyl chain in general formula (1); wherein, all nitrogen atoms on said imidazole type five-membered heterocyclic structure except those on tertiary amino group can coordinate with G; or nitrogen atom on said six-membered heterocycle can coordinate with G;

preferably, R is the structure represented by formula (18) or formula (19) in Claim 9; X1Y1 is alkyl diamine group containing 1-2 carbon atoms;

wherein, A is selected from the group consisting of benzene, biphenyl, isopropyl toluene and benzo-cyclane; B is Cl$^-$, PF$_6^-$ or BF$_4^-$; and G is preferably ruthenium.

Specifically, Z1, i.e., group formed by quinazoline derivative represented by formula (1), may be a group shown by the following general formulae:

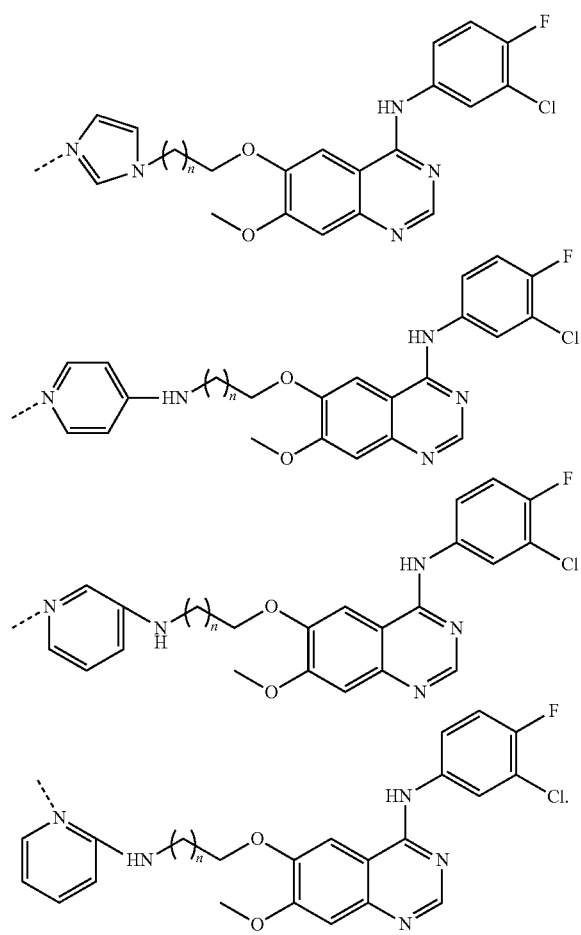

According to another particular embodiment of the present invention, said quinazoline complex as protein kinase inhibitor is represented by G(M)W:

M is a group formed by quinazoline derivative represented by general formula (1) in Claim 1, wherein, m is 0, R' is hydrogen, R is any one group of fused heterocyclic imino or substituted fused heterocyclic imino represented by general formula (2)-(7), aminoalkyl imino represented by general formula (8), group having on the ring a tertiary amino group and imidazole type five-membered heterocyclic structure represented by general formula (9), six-membered aromatic heterocyclic imino or substituted six-membered aromatic heterocyclic imino represented by any one of general formula (10)-(14) in Claim 8, W is at least one selected from halogen and DMSO; and G is ruthenium or platinum;

Preferably, R is the structure represented by formula (17) or (18) in Claim 9; W is halogen and DMSO;

nitrogen on said fused heterocycle and oxygen on hydroxyl group coordinate with G, or two nitrogen atoms on said fused heterocycle coordinate with G; alternatively, two nitrogen atoms on aminoalkyl imino coordinate with G; alternatively, two nitrogen atoms on said six-membered aromatic heterocycle can coordinate with G; alternatively, nitrogen on said R and R' coordinates with G; alternatively, nitrogen atoms on said imidazole type five-membered heterocyclic structure except those on tertiary amino group can coordinate with G; alternatively, nitrogen atom on said six-membered heterocycle coordinates with G.

Specifically, M, i.e. group formed by quinazoline derivative represented by general formula (1), has already been listed in detail above, and therefore is not discussed here repeatedly.

According to the present invention, the synthetic routes of said quinazoline complex as protein kinase inhibitor are generally divided into two categories:

I. Preparation of Organometallic Ruthenium-Based Coordination Complexes Series:

organometallic ruthenium-based coordination complexes are represented by general formula ARu(X'Y')Z, [ARu(XY)Z]$^+$B$^-$ or [ARu(X1Y1)Z1]$^+$B$^-$, wherein, A may be selected from benzene, p-cymene, biphenyl, benzo-cyclane and other aromatic hydrocarbons.

Situation (I):

(A) The preparation is performed through reaction between halogenated arene ruthenium dimer [($\eta^6$-Arene)RuCl$_2$]$_2$ containing two A groups and chelating ligand of X'Y' or XY or X1Y1 group containing two coordinating atoms (i.e. preferably Iressa derivatives containing structures of ethylene diamine, bipyridine, 8-hydroxyquinoline, phenanthrolines). Wherein, Z is Cl, B$^-$ is PF$_6^-$.

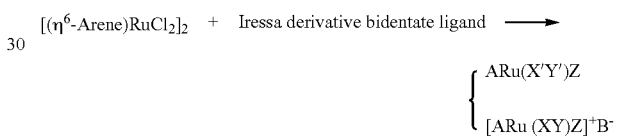

Situation (II):

(B) The preparation is performed through reacting halogenated arene ruthenium dimer [$\eta^6$-Arene)RuCl$_2$]$_2$ containing two A groups with chelating ligand of X1Y1 group containing two coordinating atoms (X1Y1 is preferably ethylene diamine), and then reacting with monodentate ligand of Z1 group containing a single coordinating atom (i.e. Iressa derivatives containing structures including imidazole). Wherein, B$^-$=PF$_6^-$.

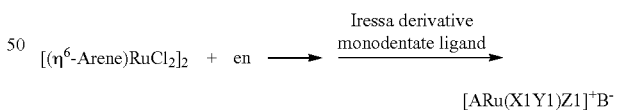

II. Preparation of NAMI as Ru (II, III) Coordination Complexes, Represented by General Formula Ru(M)W:

M is group formed by quinazoline derivative represented by general formula (1) in Claim 1 (i.e., chelating ligand including group X'Y' or XY or X1Y1 containing two coordinating atoms (i.e. preferably Iressa derivatives containing structures including ethylene diamine, bipyridine, 8-hydroxyquinoline, phenanthrolines) and monodentate ligand of Z1 group containing a single coordinating atom (i.e. Iressa derivatives containing structures including pyridine, imidazole and the like) described above), W is selected from at least one of halogen and DMSO.

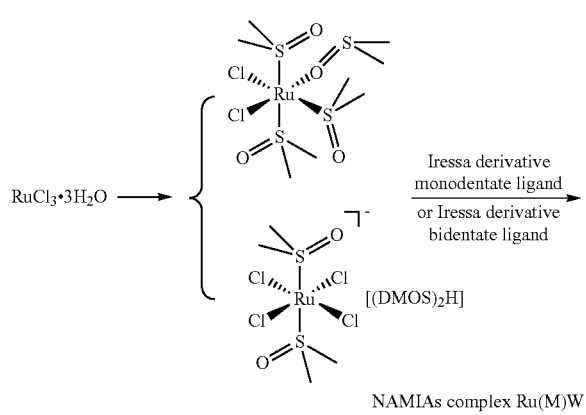

NAMIAs complex Ru(M)W

According to a specific embodiment of the present invention, method for preparation of quinazoline complex as protein kinase inhibitor represented by general formula AG(X'Y')Z or [AG(XY)Z]⁺B⁻ comprises:

contacting halogenated arene ruthenium dimer containing two A groups with the chelating ligand containing two coordinating atoms in alcohol or aqueous alcohol solution, so the ruthenium in said halogenated arene ruthenium dimer can chelate and coordinate with two coordinating atoms in chelating ligand.

Wherein, molar ratio of said halogenated arene ruthenium dimer containing two A groups to chelating ligand containing two coordinating atoms may be 1:1-3, and said contacting is carried out at temperature of 20-50° C. for 0.5-2 hours. On the basis that the total amount of said halogenated arene ruthenium dimer containing two A groups and chelating ligand containing two coordinating atoms is 100 mg, the amount of said alcohol or aqueous alcohol solution used is 30-50 ml. Said alcohol is preferably methanol, and said aqueous alcohol solution is preferably a mixed solution of methanol and water. Preferably, method by which the reaction product is separated from the reaction product mixture may be various conventional methods, for example, the method including the steps of adding NH₄PF₆ into the reaction product mixture. After fully dissolved, concentrating the reaction solution to precipitate the reaction product, and then filter it. Amount of said NH₄PF₆ used may be 6-20 times molar amount of arene ruthenium chloride dimer in this step (3).

Preferably, method for preparation of protein kinase inhibitor represented by general formula AG(X'Y')Z or [AG(XY)Z]⁺B⁻ also comprises step in which halogen atom in reaction product is substituted by one group from SCN, —N₃, —SCH₃, —SH, pyridyl, pyridyl substituted by one or several groups of alkyl with 1-3 carbon atoms, imidazolyl and imidazolyl substituted by one or several groups of alkyl with 1-3 carbon atoms, said reaction product is obtained from chelating and coordination between ruthenium in halogenated arene ruthenium dimer containing two A groups and two coordinating atoms in chelating ligand.

Wherein, method used to substitute halogen atom in reaction product, which is obtained from chelating and coordination between ruthenium in halogenated arene ruthenium dimer containing two A groups and two coordinating atoms in chelating ligand, may be a variety of conventional methods, preferably, the method comprises: in a ninth organic solvent, said reaction product is mixed with AgPF₆ or AgBF₄ at room temperature, such as 20-50° C., for 0.5-2 hours (molar ratio of the reaction product described above to AgPF₆ or AgBF₄ is typically 1:0.95-1.05), then filtered, and the filtrate is mixed with one of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms.

There is no specified limits on the used amount of said one of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms, as long as it can ensure that halogen ion is precipitated and substituted by anion of the above mentioned thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms. Generally, molar ratio of said one of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms to said reaction product is (1-5):1; preferably (1-3):1.

On the basis that the total amount of one of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms is 100 mg, the amount of said ninth organic solvent used is 30-50 mL; the said ninth organic solvent is methanol and/or ethanol.

According to the present invention, in quinazoline complex as protein kinase inhibitor represented by general formula AG(X'Y')Z and [AG(XY)Z]⁺B⁻, ligand containing two coordinating atoms for the chelating and coordinating has already been described above in detail, and will not be discussed here.

According to a specific embodiment of the present invention, preparing method for protease inhibitor represented by general formula [AG(X1Y1)Z1]⁺B⁻ comprises:

(1) contacting halogenated arene ruthenium dimer containing two A groups with alkyl diamine with 1-5 carbon atoms in alcohol or aqueous alcohol solution, under the conditions of allowing ruthenium in said halogenated arene ruthenium dimer containing two A groups to chelate and coordinate with two coordination nitrogen atoms in alkyl diamine;

(2) substituting halogen ion in reaction product obtained from chelating and coordination between ruthenium in halogenated arene ruthenium dimer containing two A groups and two coordination nitrogen atoms in alkyl diamine with 1-5 carbon atoms with monodentate ligand containing a single coordinating atom.

In step (1), molar ratio of said halogenated arene ruthenium dimer containing two A groups to alkyl diamine with 1-5 carbon atoms is 1:(1-3), and the contacting temperature may be 20-50° C., the contacting time may be 0.5-2 hours. On the basis that the total amount of said halogenated arene ruthenium dimer containing two A groups and alkyl diamine with 1-5 carbon atoms is 100 mg, amount of said alcohol or aqueous alcohol solution used may be 30-50 mL. Said alcohol is preferably methanol, and said aqueous alcohol solution is preferably aqueous solution of methanol.

In step (2), method to substitute halogen atom in reaction product obtained from chelating and coordination between ruthenium in halogenated arene ruthenium dimer containing two A groups and two coordination nitrogen atoms in alkyl diamine with 1-5 carbon atoms may be performed by a variety of conventional methods, for example, be a method comprising: in the ninth organic solvent, mixing said reaction product with $AgPF_6$ or $AgBF_4$ at room temperature, such as 20-50° C., for 0.5-2 hours (the molar ratio of the reaction product described above and $AgPF_6$ or $AgBF_4$ is generally 1:0.95-1.05), then filtering, and mixing the filtrate with a monodentate ligand with a single coordinating atom. There is no limit on the amount of said monodentate ligand with single coordinating atom used, as long as it can be sure that halogen ion is precipitated and substituted by one of the monodentate ligands with a single coordinating atom mentioned above. Generally, molar ratio of said monodentate ligand with a single coordinating atom to said reaction product is (1-5):1; preferably (1-3):1. On the basis that the total amount of said reaction product and monodentate ligand with a single coordinating atom is 100 mg, amount of said ninth solvent used may be 30-50 mL. Said ninth organic solvent is methanol and/or ethanol.

According to the present invention, in quinazoline complex as protein kinase inhibitor represented by general formula $[AG(X1Y1)Z1]^+B^-$, monodentate ligand with a single coordinating atom for coordination has already been described above in detail, and will not be discussed here.

According to the present invention, said halogenated arene ruthenium dimer containing two A groups is commercially available, and may also be prepared in accordance with method well known to those skilled in the art. For example, the preparation method of said halogenated arene ruthenium dimer containing two A groups may comprise:
(1) in a mixture of liquid ammonia and lower alcohol, mixing an aromatic hydrocarbon with an alkali metal to obtain dihydride aromatics;
(2) contacting dihydride aromatics with ruthenium halide in the seventh organic solvent so as to produce halogenated arene ruthenium dimer.

Wherein, in said step (1) of the method to prepare halogenated arene ruthenium dimer containing two A groups, said reaction by which aromatic hydrocarbon is deoxidized to dihydride aromatics is the Birch reaction, which is well known to those skilled in the art, reaction conditions and methods are also well known to those skilled in the art. For example, molar ratio of alkali metal, such as sodium, potassium or lithium, to reactant aromatic hydrocarbon may be (4-8):1, molar ratio of liquid ammonia, lower alcohol and reactant aromatic hydrocarbon may be (200-300):(10-15):1. Said lower alcohol may be one or more selected from methanol, ethanol, isopropanol, and butanol. Said reaction temperature may be −78° C. to −50° C., and said reaction time may be 1-3 hours.

Usually, the reaction product obtained after performing Birch reaction is a mixture of dihydride aromatics and some unreacted raw aromatic hydrocarbon. Even though part of the solvent and unreacted raw material can be removed by vacuum distillation, it is impossible to separate dihydride aromatics completely from the mixture of reaction product. Therefore, in fact, the mixture of reaction product is used as a raw material of the subsequent reaction. And it is demonstrated by nuclear magnetic resonance (NMR) analysis that, the purity of dihydride aromatics is generally at 60-90% by weight in the reaction product mixture.

Wherein, in said step (1) of the method to prepare halogenated arene ruthenium dimer containing two A groups, the amount of said reaction product mixture containing dihydride aromatics obtained from step (1) used should allow that the molar ratio of said dihydride aromatics wherein to ruthenium halide (III) is 3-5:1. Conditions of said contacting include that the contacting temperature may be 60-90° C., the contacting time maybe 1-12 hours. Said seventh organic solvent may be selected from ethanol and/or methanol. On the basis that the total amount of dihydride aromatics and ruthenium halide (III) is 100 mg, amount of said seventh organic solvent used may be 30-50 mL. And then the halogenated arene ruthenium dimer may be separated through methods comprising filtration and washing.

Preferably, said A groups in said halogenated arene ruthenium dimer containing two A groups are selected from the group consisting of benzene, biphenyl, isopropyl toluene and benzo-cyclane.

According to a particular embodiment of the present invention, when M is ruthenium, the preparation method of the quinazoline complex as protease inhibitor represented by general formula G(M)W comprises:
(1) in the presence of a tenth organic solvent, heating ruthenium halide and a mixture of aqueous hydrochloric acid and DMSO to reflux, or heating ruthenium halide and DMSO to reflux so as to obtain ruthenium compound coordinating with DMSO;
(2) contacting the ruthenium compound coordinating with DMSO obtained in step (1) with quinazoline derivative ligand containing a single or two coordinating atoms in alcohol or in aqueous alcohol solution or in hydrochloric acid solution of alcohol, so as to allow ruthenium of ruthenium compound coordinating with DMSO to coordinate with single or two coordinating atoms in said ligand.

According to the present invention, in step (1), the temperature of said heating and refluxing may be 70° C. to 200° C., duration of said heating and refluxing may be 3-6 hours. The molar ratio of said ruthenium halide to chlorine hydride in aqueous hydrochloric acid may be 1:(40-80), and the molar ratio of said ruthenium halide to DMSO may be 1:(40-80). Said tenth organic solvent may be a conventionally used organic solvent, for example, it may be one or more selected from methanol, ethanol, isopropanol. On the basis that the total amount of ruthenium halide, aqueous hydrochloric acid and DMSO is 2000 mg, the amount of said tenth organic solvent used may be 30-50 mL.

According to the present invention, in step (2), the molar ratio of said ruthenium compound coordinating with DMSO to quinazoline derivative chelating ligand containing two coordinating atoms may be 1:(1-3), the contacting temperature may be 20-50° C., and the contacting time may be 0.5-6 hours. On the basis that the total amount of ruthenium compound coordinating with DMSO and chelating ligand containing two coordinating atoms is 100 mg, the amount of said alcohol or aqueous alcohol solution used may be 3-10 ml. Said alcohol is preferably ethanol, and said aqueous alcohol solution is preferably aqueous solution of ethanol. Alternatively, according to the present invention, in step (2), the molar ratio of said ruthenium compound coordinating with DMSO to monodentate ligand containing a single coordinating atom may be 1:(1-3), said contacting temperature may be 20-50° C., and the contacting time may be 0.5-6 hours. On the basis that the total amount of ruthenium compound coordinating with DMSO and quinazoline derivative chelating ligand containing a single coordinating atom is 100 mg, the amount of said alcohol or hydrochloric acid solution of alcohol may be 8-20 mL. Said alcohol is preferably ethanol.

According to a particular embodiment of the present invention, the preparation method of the quinazoline complex as protease inhibitor represented by general formula G(M)W comprises allowing a dissolved platinum compound such as dipotassium tetrachloroplatinate in the presence of a eleventh organic solvent to contact quinazoline derivative ligand containing a single or two coordinating atoms under the conditions of allowing platinum compound coordinating with single or two coordinating atoms in said ligand.

Said dissolved platinum compound could be used in a solution in water.

Said eleventh organic solvent is preferably DMF.

Said molar ratio of said dissolved platinum compound to quinazoline derivative ligand containing a single or two coordinating atoms may be 1:(0.8-3), said conditions of allowing platinum compound coordinating with single or two coordinating atoms in said ligand comprises contacting temperature being 40-80° C., and the contacting time may be 6-18 hours.

According to the present invention, in quinazoline complex as protein kinase inhibitor represented by general formula G(M)W, said chelating ligand containing two coordinating atoms used for coordination as well as monodentate ligand containing a single coordinating atom have already been described above in detail, and therefore they are not discussed here.

Preferred embodiments of present invention are described above in detail; however, the present invention is not limited to specific details in the embodiment described above. Within the field of technical concept of present invention, a variety of simple transformations may be made to technical schemes of the present invention, and all these simple transformations belong to the protection scope of present invention.

It is also important that, each specific technical feature as described in the specific embodiment above may be combined in any suitable manner, as long as there is no contradiction. In order to avoid any unnecessary duplication, various possible combinations will not be discussed any more in the present invention.

In addition, various different embodiments of the present invention can also be combined freely, as long as it is not contrary to the concept of the invention, and the combinations should also be considered as content disclosed in the present invention.

The present invention will be further described through specific embodiments in detail as below.

Example 1

This example is intended to explain the preparation of quinazoline derivative ligand and quinazoline complex as protein kinase inhibitors provided by the present invention.

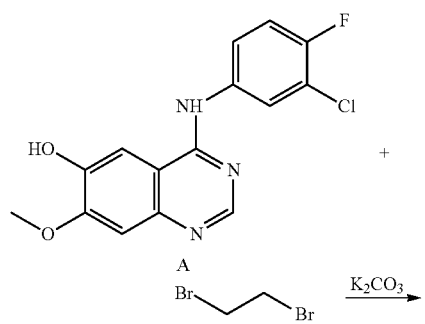

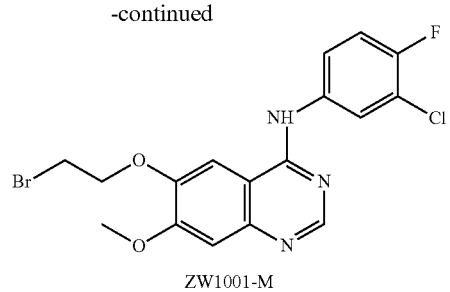

ZW1001-M (1) 2.0 g of the first reactant A (4-(3'-chloro-4'-fluoro-phenylamino)-6-hydroxy-7-methoxy-quinazoline (purchased from Nanjing Ange Pharmaceutical Co., Ltd.) in reaction scheme above and 5.0 g acid binding agent anhydrous potassium carbonate are added into 30 mL DMF, the temperature of the oil bath is controlled to 87° C., stirring for 15 minutes, then 2 mL 1,2-dibromoethane is added dropwise. The temperature is maintained to allow the reaction to continue for 4.5 hours. After completion of the reaction, the mixture is cooled to room temperature and filtered by suction, the filtrate is collected and slowly poured into 120 ml of cold water while stirring. Then a viscous substance is precipitated and extracted by ethyl acetate 50 mL for three times, the extracts are combined and washed with 30 mL water once, and dried with anhydrous sodium sulfate. The product is separated by silica gel column chromatography (ethyl acetate/petroleum ether=4:1), to give 0.5 g pale yellow powder of intermediate product ZW1001-M, and the yield is 17%.

$^1$H-NMR (DMSO-$d_6$, 400 MHz), δ(ppm): 9.55 (1H, s), 8.52 (1H, s), 8.12 (1H, dd, $J_1$=6.7 Hz, $J_2$=2.4 Hz), 7.85 (1H, s), 7.78 (1H, dd, $J_1$=8.6 Hz, $J_2$=4.6 Hz), 7.48 (1H, t, $J_1$=$J_2$=9.0 Hz), 7.24 (1H, s), 4.50 (2H, t, $J_1$=$J_2$=5.5 Hz), 3.93 (5H, m); ESI-MS: m/z 428.61, 430.61 ([M]$^+$).

IC$_{50}$ value of the intermediate product, compound No. ZW1001-M, obtained by the present example is determined to be 18 nM under ELISA test conditions, indicating that the compound has a good kinase inhibitory activity.

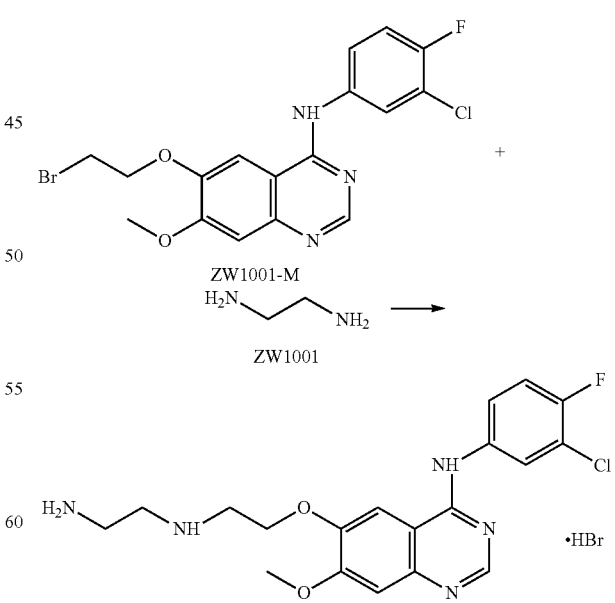

(2) 0.80 g of the intermediate product ZW1001-M (4-(3'-chloro-4'-fluoro-phenylamino)-6-(2-bromo-ethoxy)-7-methoxy quinazoline) obtained in step (1) and 1 mL distilled ethylenediamine (purchased from Beijing Chemical Reagent Co.), was heated to reflux in 40 mL of acetonitrile for 3 hours, the temperature for heating and refluxing is 80° C. After the reaction stops, crystal is precipitated through natural cooling. The resulted was suction filtered, and the filter cake is washed with acetonitrile and dried to give 0.6 g of white solid No. ZW1001, and the yield is 67%.

ESI-MS: m/z 406.9 ([M+H]$^+$).

Figure 5:
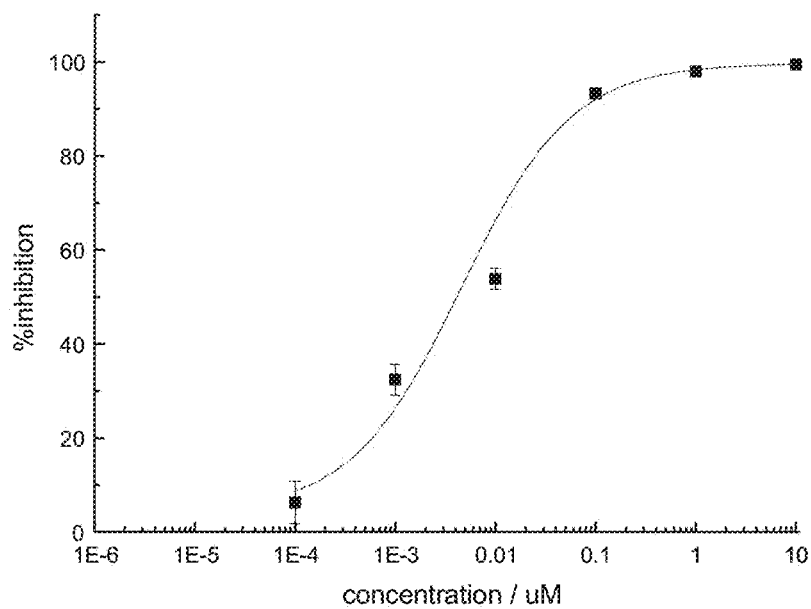
FIG. 5 is the graph of compound No. ZW1001 under the condition of ELISA showing $IC_{50}$=4.6 nM.

FIG. 5 is the $IC_{50}$ graph of compound No. ZW1001 at $IC_{50}$=4.6 nM under ELISA test conditions, which indicates that this inhibitor has a good inhibitory activity on EGFR protein kinase inhibitor.

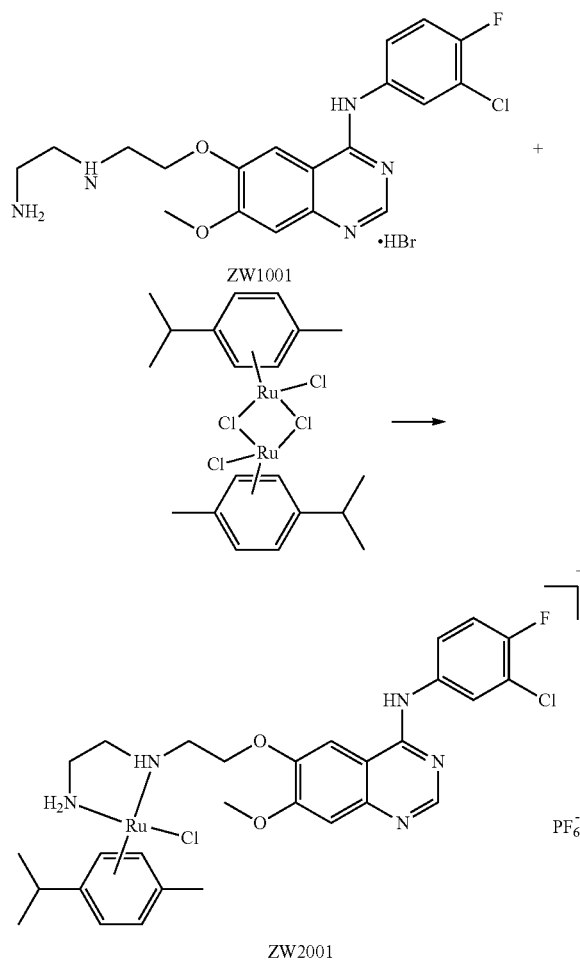

ZW1001

ZW2001

(3) 0.2 g of product ZW1001 prepared in step (2) is placed in a 50 ml round-bottomed flask, 12 mL of anhydrous methanol is added for dissolving, and then 0.2 g of anhydrous potassium carbonate is added. The mixture is stirred at room temperature (25° C.) for 0.5 h, insoluble is filtered off under normal atmosphere, and the filtrate is collected. 0.12 g of arene ruthenium dimer (p-cymene ruthenium dimer, purchased from Tokyo Chemical Industry Co., Ltd.) is added, and then the reaction is allowed to occur under stirring at room temperature (25° C.) for 7 h. After completion of the reaction, 0.4 g of ammonium hexafluorophosphate is added, and stirring at room temperature for 0.5 h. The product is separated by silica gel column chromatography (the ratio of methanol/dichloromethane is 1:20 by volume), to give a red oil, and the column chromatography product is further purified by thin layer chromatography (the ratio of methanol/ dichloromethane is 1:10 by volume) to obtain 0.10 g of pale yellow powder No. ZW2001. The yield is 35%.

$^1$H-NMR (DMSO-d$_6$, 400 MHz), δ(ppm): $^1$H-NMR δ(ppm): 9.62 (1H, s), 8.54 (1H, s), 8.15 (1H, d), 7.94 (1H, s), 7.80 (1H, m), 7.45 (1H, m), 7.31 (1H, s), 6.60 (2H, m), 5.78 (1H, m), 5.64 (4H, m), 4.46 (2H, d), 4.00 (3H, s), 3.81 (1H, m), 3.51 (1H, m), 2.85 (2H, m), 2.72 (3H, m), 2.32 (1H, s), 2.23 (3H, s), 2.02 (1H, s), 1.98 (3H, m).

ESI-MS: 676.1 (M$^+$), 640.1 (M-Cl)$^+$

Figure 6:
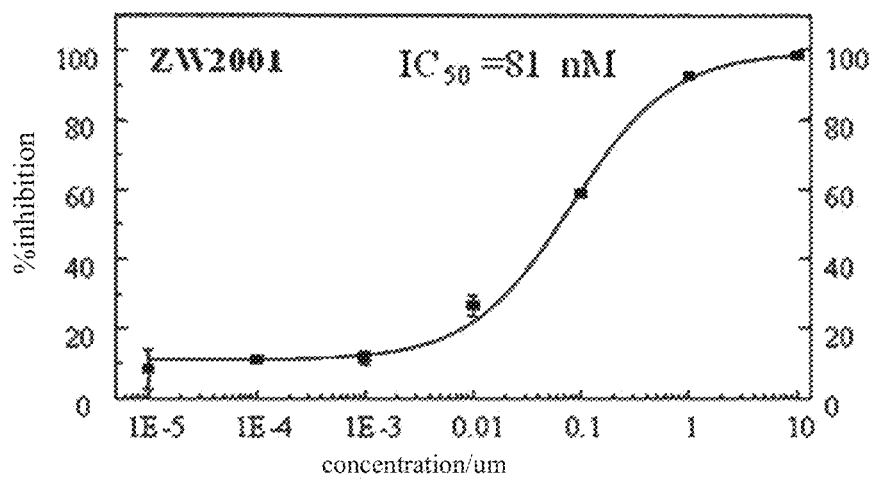
FIG. 6 is the graph of compound No. ZW2001 under the condition of ELISA showing $IC_{50}$=81 nM.

FIG. 6 is the $IC_{50}$ graph of compound No. ZW2001 at $IC_{50}$=81 nM under ELISA test conditions, which indicates that this inhibitor has a good inhibitory activity on EGFR protein kinase inhibitor.

Examples 2-6

These examples are intended to explain the preparation of quinazoline derivative ligand and quinazoline complex as protein kinase inhibitors provided by the present invention.

In Example 2 and Example 3, ligand and coordination complex are prepared according to the method of Example 1, except for the following difference: in step (3), 0.1 g benzene ruthenium dimer (purchased from Tokyo Chemical Industry Co., Ltd.) and 0.15 g biphenyl ruthenium dimer are used instead of p-cymene ruthenium dimer used in the step (3) of Example 1, respectively, so as to obtain quinazoline complex as protein kinase inhibitor No. ZW2002 and ZW2003 with the following structures.

Wherein, preparation method of said ruthenium biphenyl dimer is: in a mixture of liquid ammonia and ethanol, biphenyl is mixed with metallic sodium at −78° C. for 1 hour (the molar ratio of liquid ammonia, ethanol, biphenyl and sodium is 250:10:1:5), to obtain dihydride biphenyl; then the reaction product is subjected to vacuum distillation at 150° C., the solvent and a portion of the unreacted raw material are removed, and the purity of dihydride biphenyl in the reaction product mixture is determined by NMR analysis to be approximately 70% by weight.

(2) The reaction product mixture containing dihydride biphenyl is made to contact ruthenium chloride in ethanol, wherein, amount of the reaction product mixture containing dihydride biphenyl should be such that the molar ratio of dihydride biphenyl to ruthenium chloride is 5:1, the contacting temperature is 80° C., the contacting time is 8 hours. On the basis that the total weight of dihydride biphenyl and ruthenium chloride is 100 mg, 60 ml of ethanol should be used. The mixture is filtered and washed with methanol to obtain biphenyl ruthenium trichloride dimer.

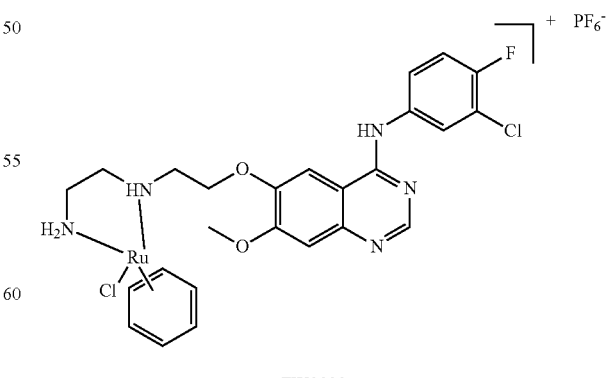

ZW2002

$^1$H-NMR δ(ppm): 8.61 (1H, s), 8.12 (2H, d), 8.10 (1H, s), 7.77 (1H, s), 7.40 (4H, m), 6.85 (1H, m), 6.25 (1H, m), 5.69

(1H, m), 4.45 (3H, s), 4.02 (4H, m), 2.50 (2H, m), 2.33 (1H, d), 2.02 (1H, d) MALDI-TOF: 620.1 (M⁺), 584.31 (M-Cl)⁺

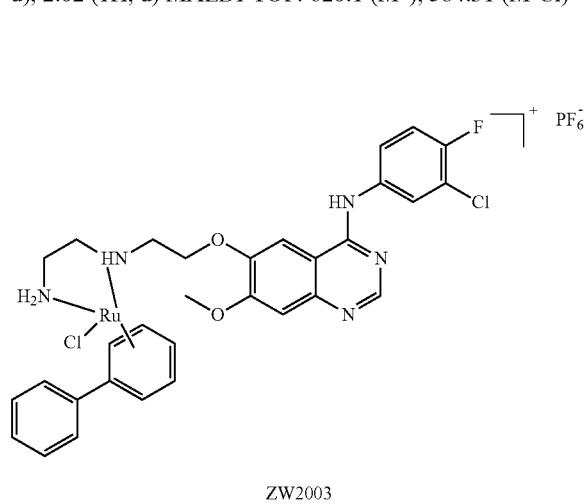

ZW2003

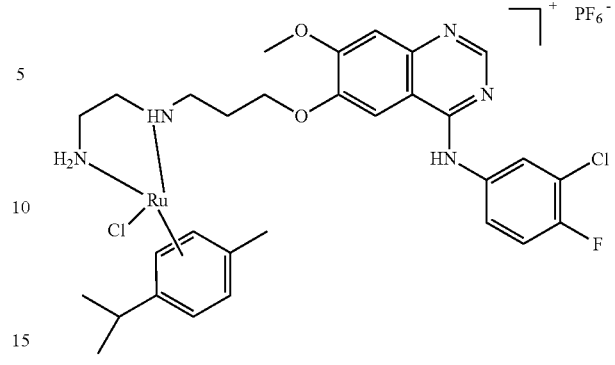

ZW2004

¹H-NMR δ(ppm): 8.63 (1H, s), 8.11 (1H, s), 8.10 (1H, s), 7.78 (3H, m), 7.46 (5H, m), 7.31 (1H, s), 6.78 (1H, d), 6.28 (2H, m), 6.04 (1H, m), 5.89 (1H, m), 4.38 (2H, s), 4.06 (3H, s), 3.74 (2H, s), 3.69 (2H, s), 2.02 (2H, s).

MALDI-TOF: 696.1 (M⁺), 660.3 (M-Cl)⁺

In Example 4, ligand and coordination complex are prepared according to the method of Example 1, except for the following difference:

In step (1), 4.8 mL of 1,3-dibromopropane is used instead of 1,2-dibromoethane to give 1.3 g pale yellow powder of intermediate product ZW1002-M, and the yield is 37.8%; acetone is used as solvent instead of DMF.

In step (2), 0.70 g of intermediate product ZW1002-M (4-(3'-chloro-4'-fluoro-phenylamino)-6-(2-bromo-propoxy)-7-methoxy-quinazoline) obtained by the step (1) is allowed to react with 1.3 mL distilled ethylenediamine (purchased from Beijing Chemical Reagent Co.), in 40 mL of acetonitrile at room temperature (25° C.) for 9 hours. After the reaction stops, crystal is precipitated by natural cooling and filtered, the filter cake is washed with acetonitrile once and dried to obtain 5 g white solid of No. ZW1002, the yield is 65.62%.

In step (3), 0.3 g of product ZW1002 prepared by step (2) is placed in a 50 ml round-bottomed flask, 12 mL of anhydrous methanol is added for dissolving, and then 0.3 g of anhydrous potassium carbonate is added. The mixture is stirred at room temperature (25° C.) for 0.5 h, insolubles are filtered off under normal atmosphere, the filtrate is collected. 0.22 g of arene ruthenium dimer (p-cymene ruthenium dimer, purchased from Tokyo Chemical Industry Co., Ltd.) is added, and then the reaction is allowed to occur under stirring at room temperature (25° C.) for 7 h. After completion of the reaction, 0.4 g of ammonium hexafluorophosphate is added, and stirring at room temperature for 0.5 h. The product is separated by silica gel column chromatography (the ratio of methanol/dichloromethane is 1:20 by volume), to give a red oil, and the column chromatography product is further purified by thin layer chromatography (the ratio of methanol/dichloromethane is 1:10 by volume) to obtain 0.15 g of pale yellow powder No. ZW2004. The yield is 23%.

MALDI-TOF: 690.6 (M⁺), 655.3 (M-Cl)⁺

Figure 8:
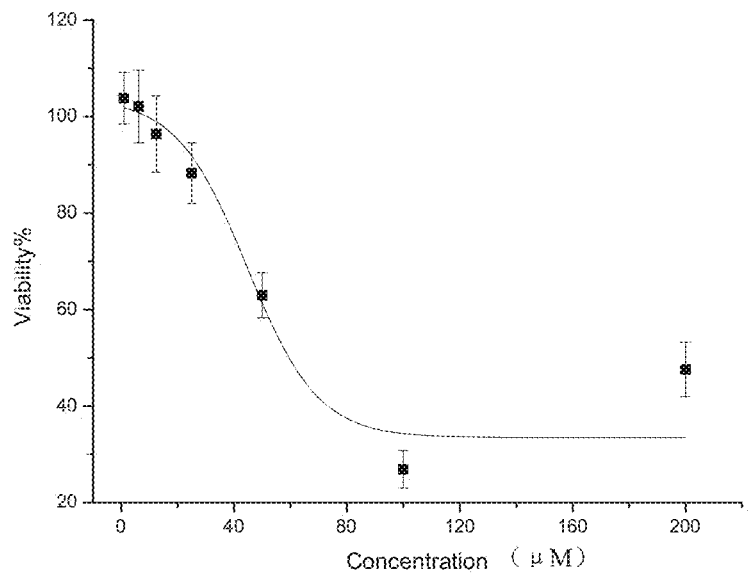
FIG. 8 is the graph of compound No. ZW2004 measured under the test condition of MCF-7/S+EGF inhibiting the proliferation of tumor cells showing $IC_{50}$=33.87 µM.
Figure 9:
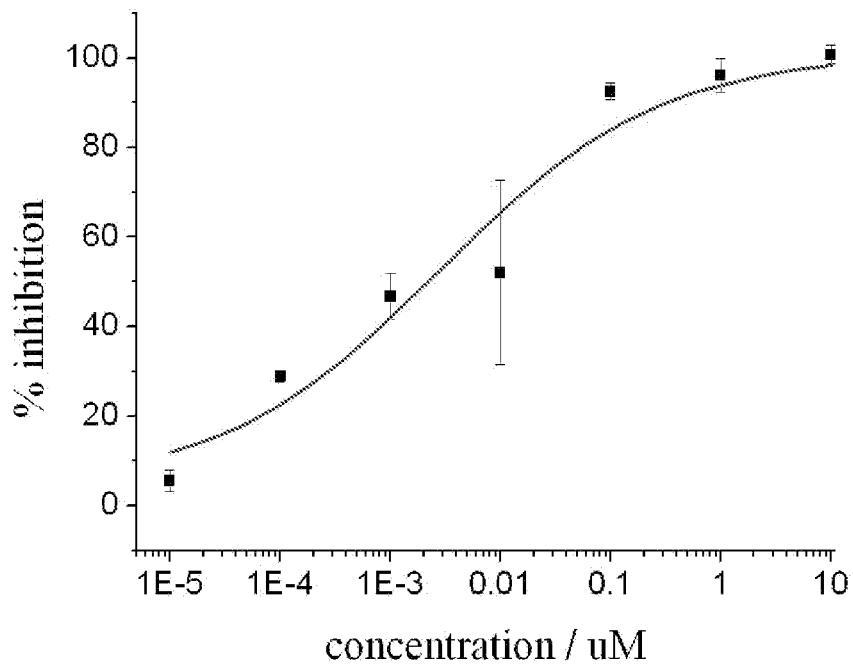
FIG. 9 is the graph of compound No. ZY-1 measured under the condition of ELISA showing $IC_{50}$=2.8 nM.
Figure 10:
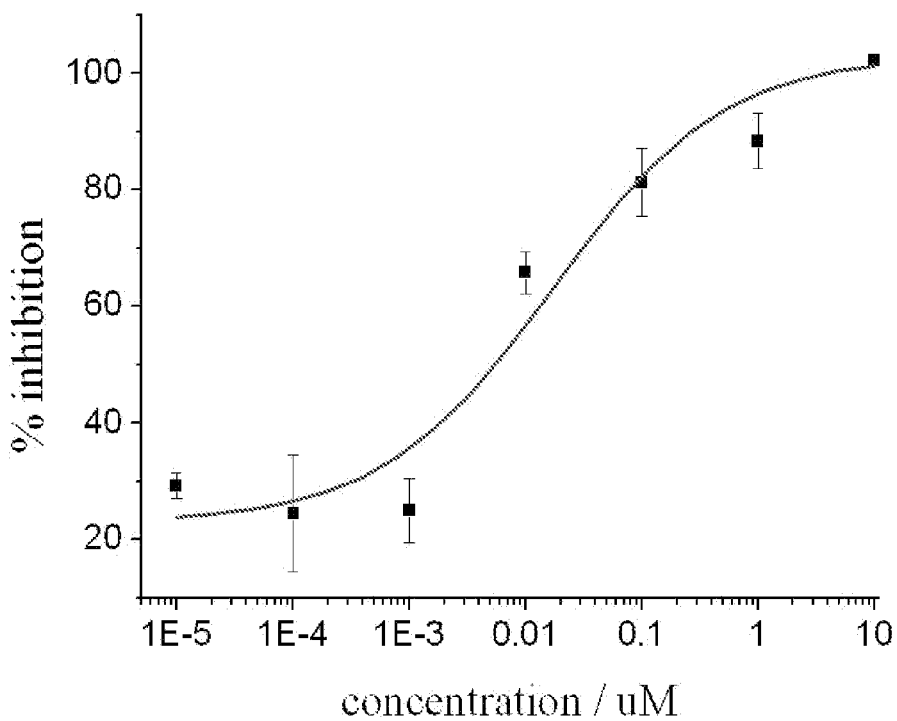
FIG. 10 is the graph of compound No. ZY-2 measured under the condition of ELISA showing $IC_{50}$=16.99 nM.

FIG. 8 is the graph of compound No. ZW2004 at $IC_{50}$=33.87 uM under the test conditions of MCF-7/S+EGF inhibiting tumor cell proliferation, showing that this inhibitor has a good inhibitory activity on EGFR protein kinase inhibitor.

In Examples 5-6, ligand and coordination complex are prepared according to the method in Example 4, except for the following difference: in step (3), 0.3 g benzene ruthenium dimer (purchased from Tokyo Chemical Industry Co., Ltd.) and 0.25 g ruthenium biphenyl dimer (prepared according to method described in Example 3) are used instead of p-cymene dimer used in the step (3) of Example 1, respectively, so as to obtain quinazoline complex as protein kinase inhibitor No. ZW2005 and ZW2006 with the following structures.

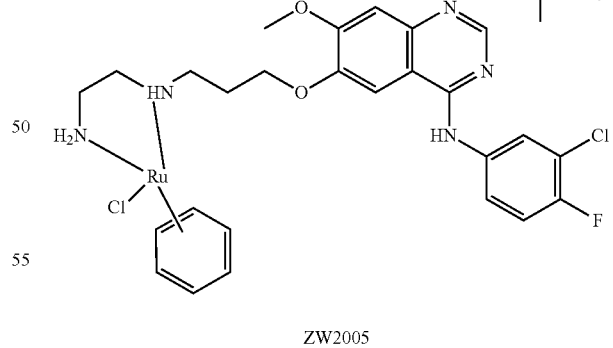

ZW2005

¹H-NMR δ(ppm): 8.81 (1H, s), 8.04 (2H, m), 7.72 (1H, m), 7.55 (1H, m), 7.26 (2H, m), 6.85 (1H, m), 6.65 (2H, m), 5.85 (1H, s), 4.00 (3H, s), MALDI-TOF: 634.3 (M⁺), 598.1 (M-Cl)ᶦ

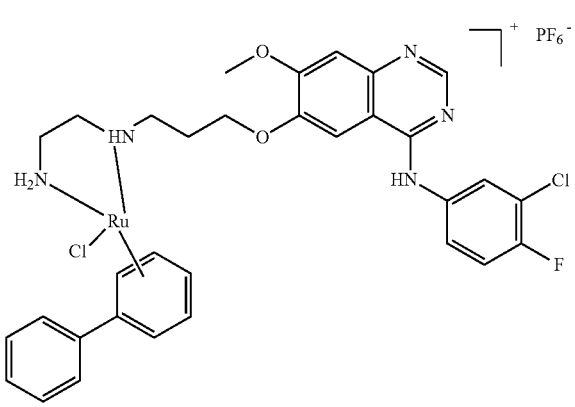

ZW2006

MALDI-TOF: 709.1 (M+), 674.3 (M-Cl)+

Example 7

This example is intended to explain the preparation of quinazoline derivative ligand and quinazoline complex as protein kinase inhibitors provided by the present invention.

The synthetic route is shown as the following reaction scheme:

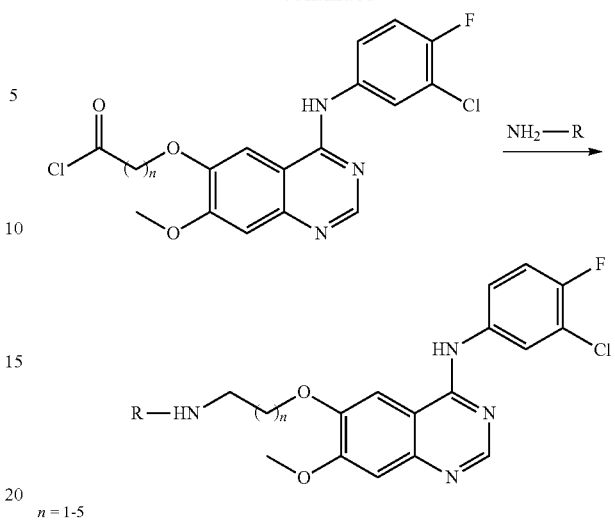

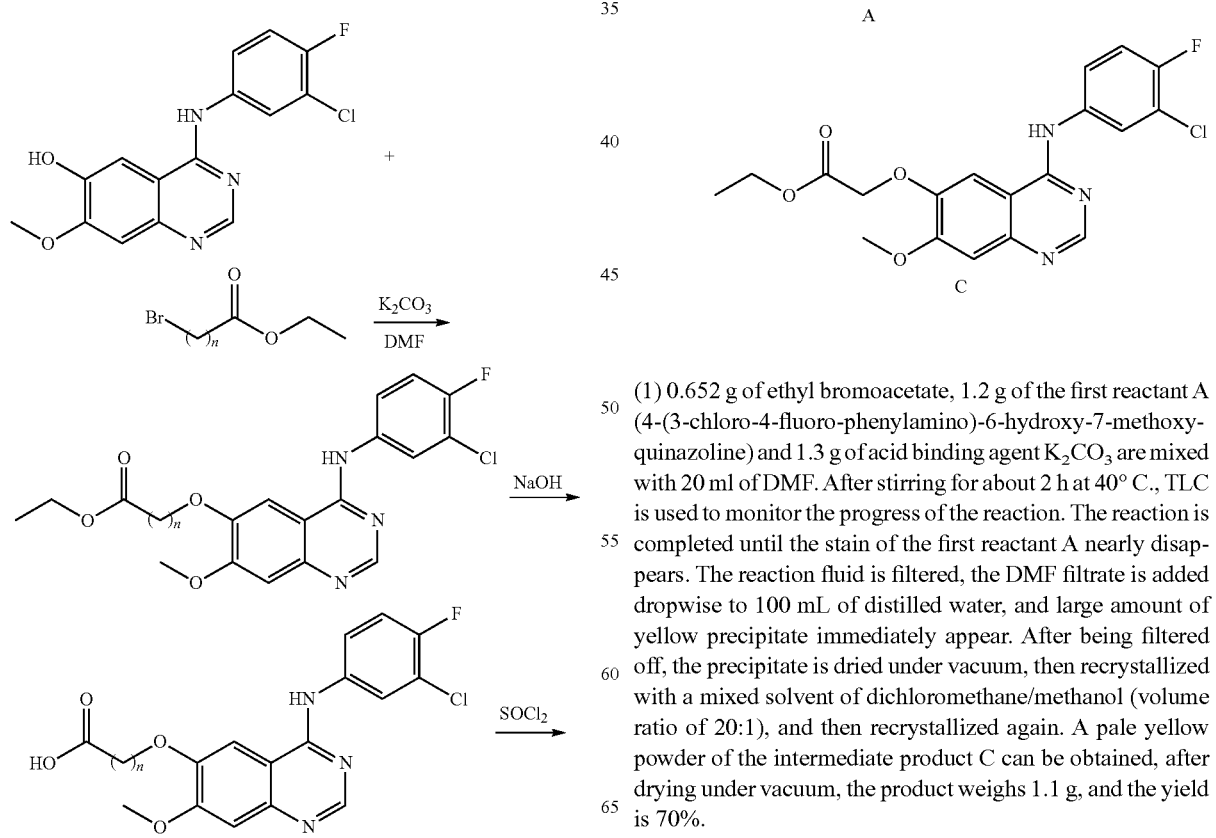

(1) 0.652 g of ethyl bromoacetate, 1.2 g of the first reactant A (4-(3-chloro-4-fluoro-phenylamino)-6-hydroxy-7-methoxy-quinazoline) and 1.3 g of acid binding agent $K_2CO_3$ are mixed with 20 ml of DMF. After stirring for about 2 h at 40° C., TLC is used to monitor the progress of the reaction. The reaction is completed until the stain of the first reactant A nearly disappears. The reaction fluid is filtered, the DMF filtrate is added dropwise to 100 mL of distilled water, and large amount of yellow precipitate immediately appear. After being filtered off, the precipitate is dried under vacuum, then recrystallized with a mixed solvent of dichloromethane/methanol (volume ratio of 20:1), and then recrystallized again. A pale yellow powder of the intermediate product C can be obtained, after drying under vacuum, the product weighs 1.1 g, and the yield is 70%.

ESI-MS: m/z 406.2 ([M+H]$^+$); 444.2 ([M+K]$^+$).

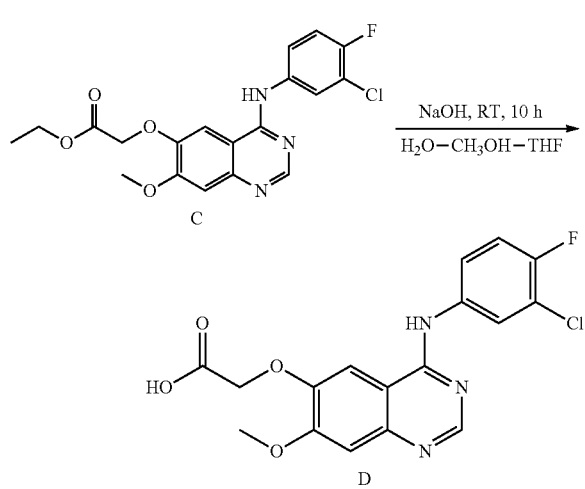

(2) About 88 mg (2.2 mmol) of NaOH and 446.6 mg of intermediate product C (dispersed in 20 mL of mixed solvent of water-methanol-tetrahydrofuran with the same ratio by weight) obtained by the step (1) are mixed with 30 mL of mixed solvent of water-methanol-tetrahydrofuran (the volume ratio is 1:1:3), and the reaction is stirred for 12 hours at room temperature. After the reaction stops, the reaction mixture is concentrated to 10 mL by vacuum rotary evaporation, and is adjusted to acidic using 25% HCl solution (mass %). A large amount of white floc is precipitated, vacuum suction filtration is performed, and the filter cake is dried in vacuum, to give the intermediate D. The product weighs 415 mg, and the yield is 82%.

MS (EI, 80 eV) m/z 377 (M+)

(3) In a 100 ml three-necked flask equipped with a reflux condenser (upper end with anhydrous calcium chloride drying tube, and connected to an airway passing into the NaOH saturated liquid to absorb exhaust), 5 mmol of the intermediate product D obtained in step (2), and 3.5 mL (about 40 mmol) of thionyl chloride are added. One drop of pyridine (about 0.6 mmol) as well as additional 1-2 drops of DMF (approximately 0.5-2.0 mmol) are added in order to aid carboxylic acid dissolving. The mixture resulted is heated in an oil bath and stirred thoroughly for about 50 minutes, and then temperature is raised to 75° C. and maintained at 70-75° C. (2-3 hours), until no gas escapes. After the completion of the reaction, excess thionyl chloride is distilled off under reduced pressure, and the mixture is cooled to give the intermediate product E, which is then dissolved in about 10 ml of anhydrous dichloromethane, and placed in a constant pressure funnel of 50 ml. 0.77 g of 5-methyl-amine-2,2'-bipyridyl and 0.64 g of acid binding agent triethylamine (molar ratio of the three substances is approximately 1.2:1.0:1.5) are dissolved in 30 mL of dichloromethane, and put into a 100 ml three-necked flask and stirred at ice-bath, meanwhile a solution of the intermediate product E is added slowly and dropwise. After the dropping (10 minutes), the reaction temperature is maintained at about 5° C. The stirring continues for 3 hours so as to complete the reaction. Then the resulted is filtered to remove the precipitate, and the filtrates are combined and concentrated under reduced pressure, so as to obtain a crude target product. Then it is recrystallized with ethanol, or recrystallized again, to give pure product. Product weighs 1.32 g, and the yield is 48.5%.

ESI-MS: m/z 544 ([M+H]+)

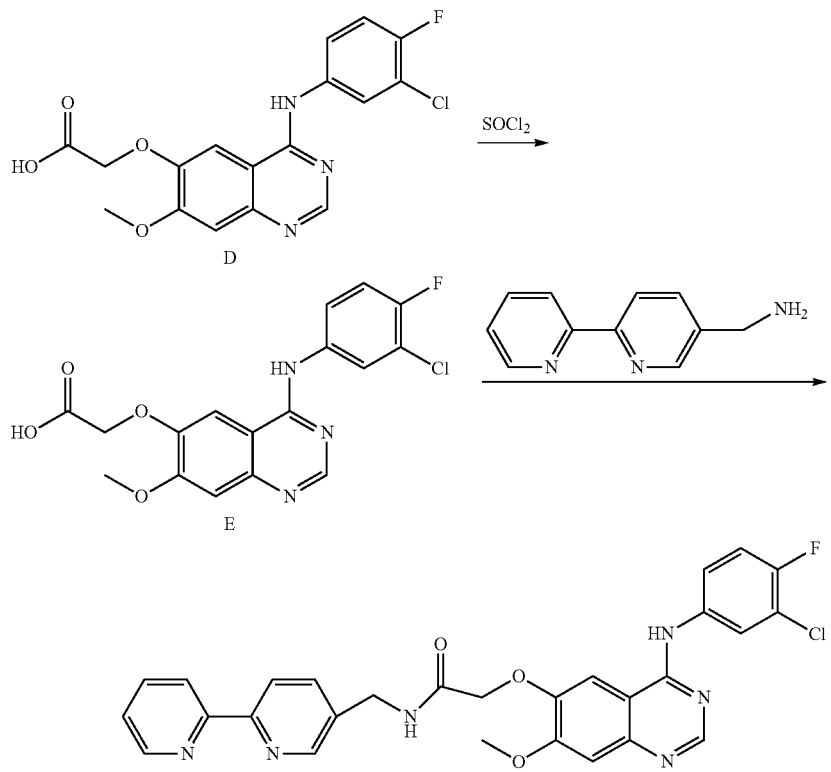

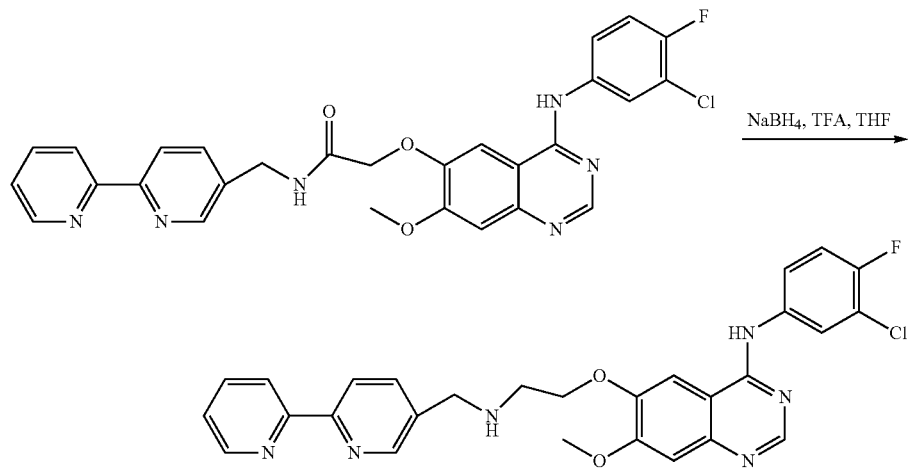

(4) Sodium borohydride (380 mg, 10 mmol) is suspended in 100 mL of dry THF, trifluoroacetic acid (TFA, 2 mL) is added dropwise under the protection of argon, and it is stirred at room temperature until no bubbles. The solution of target product (544 mg, about 1 mmol) obtained in step (3) in 50 mL THF is added. And the resulted is heated to reflux for 2 hours, and 100 mL of water is added to quench the reaction. Extracted with ethyl acetate, the organic layer is dried over anhydrous sodium sulfate, concentrated to completely dry under reduced pressure, and separated by silica gel column chromatography (volume ratio of dichloromethane/methanol is 20/1), a white target product is obtained in the yield of 32%.

ESI-MS: m/z 531.2 ([M+H]$^+$).

Example 8

This example is intended to explain the preparation of quinazoline derivative ligand and quinazoline complex as protein kinase inhibitors provided by the present invention.

Take 0.5 g (approximately 1.56 mmol) of the first reactant A (4-(3-chloro-4-fluoro-phenylamino)-6-hydroxy-7-methoxy-quinazoline) into a 50 mL round bottom flask, add 3.0 g of pyridine hydrochloride solids, and the temperature is raised to 170° C. in oil bath under the protection of argon, the reactants melt gradually under magnetic stirring, and the reaction temperature is maintained for 4 h. After the completion of the reaction, it is cooled to room temperature, and add 30 mL water, heat at reflux for 10 min, cool and suction filtration. And the filter cake is dried and recrystallized with anhydrous methanol to give 0.36 g of a yellow-green powder of intermediate product H, and the yield is 75%.

ESI-MS: m/z 306.8 ([M+H]$^+$)

The synthetic route is as following:

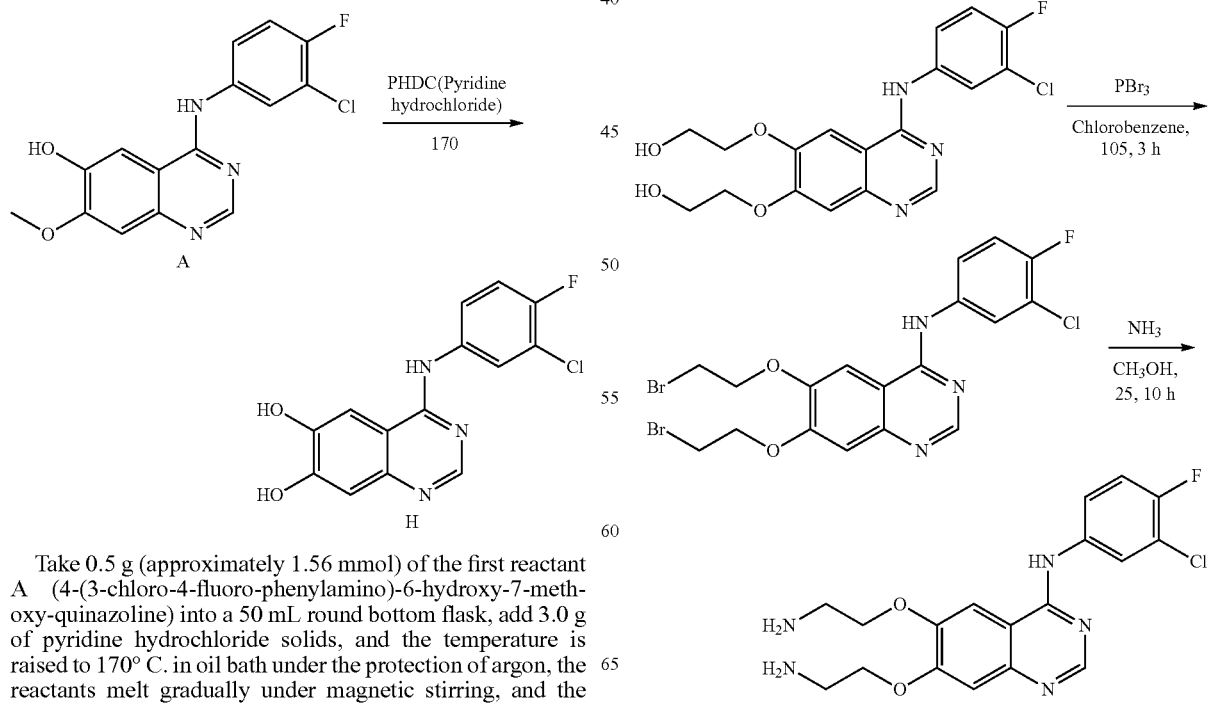

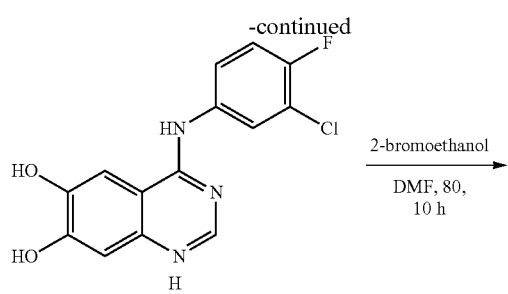

(1) 1.33 g of the intermediate product H (4-(3-chloro-4-fluoro-phenylamino)-6,7-dihydroxy-quinazoline) obtained in the step above, and 7.0 g of anhydrous potassium carbonate are mixed with 70 ml acetone. The temperature of the oil bath is controlled to 50° C., it is heated to reflux and stirred for 15 min, then 3 mL of 2-bromoethanol is added dropwise. The temperature is maintained to allow the reaction to continue for 10 h. After the completion of the reaction, the mixture is cooled to room temperature and suction filtered, and the filtrate is collected and concentrated. The product is separated by silica gel column chromatography (the volume ratio of methanol/dichloromethane is 1:15), 0.8 g of a white powder of the intermediate product I is obtained, and the yield is 46.8%.

ESI-MS testing: m/z 394.8 ([M+H]$^+$)

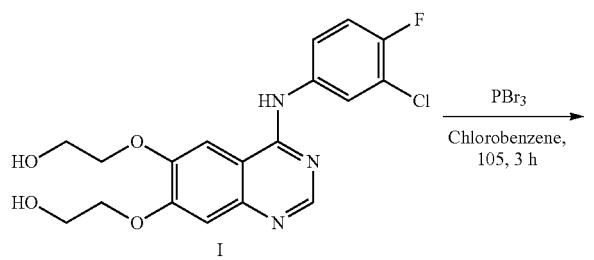

(2) 0.4 g of the intermediate product I obtained by step (1) together with 15 mL of dry chlorobenzene and 0.5 mL of pyridine are stirred at room temperature (25° C.), to obtain a suspension. Additionally, take 0.15 mL of phosphorus tribromide, add 3 mL of chlorophenyl for dilution, and the result solution is slowly added to the suspension above dropwise at room temperature (25° C.). And after the completion of the dropping, the solution is heated to reflux for reaction for 3 hours. The reaction is completed when TLC shows that the stain of the reactant I nearly disappears. The reaction solution is cooled to room temperature and washed successively with saturated sodium bicarbonate solution and saturated sodium chloride solution, dried over anhydrous magnesium sulfate and concentrated to give pale yellow viscous substance of the intermediate product J. It is separated by silica gel column chromatography (the volume ratio of methanol/dichloromethane is 1:15), to give 0.25 g of product (9) white powder, and the yield is 47%.

ESI-MS testing: m/z 520.40 ([M+H]$^+$) 542.4 ([M+Na]$^+$)

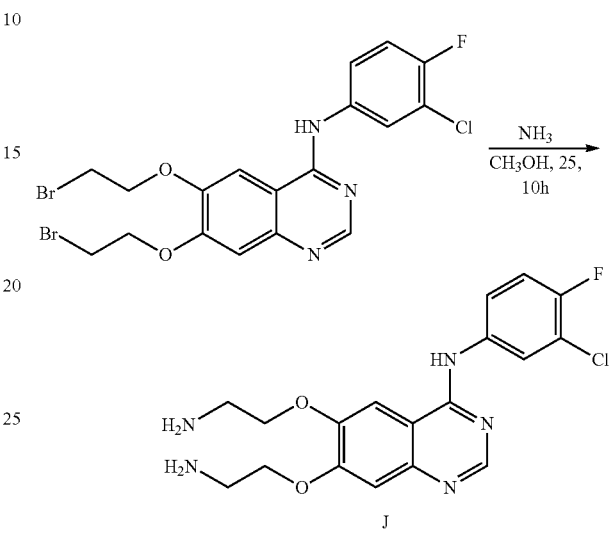

(3) At room temperature (25° C.), 0.5 g of the intermediate product J obtained by step (2) is mixed with 15 mL of saturated ammonia-methanol solution (the molar ratio of intermediate product J to ammonia used is 1:20), and then the reaction is allowed under stirring at room temperature (25° C.) for 10 h. The reaction is completed when TLC shows that the stain of the reactant J nearly disappears. A white powder is obtained by rotary evaporation, washed with cold water once, and 0.28 g product white powder is obtained through recrystallization with methanol and water, and the yield is 76%.

ESI-MS testing: m/z 392.83 ([M+H]$^+$) 414.74 ([M+Na]$^+$)

Example 9

This example is intended to explain the preparation of quinazoline derivative ligand and quinazoline complex as protein kinase inhibitors provided by the present invention.

Synthesis of Quinazoline Derivative Protein Kinase Inhibitor Ligand JLY1002:

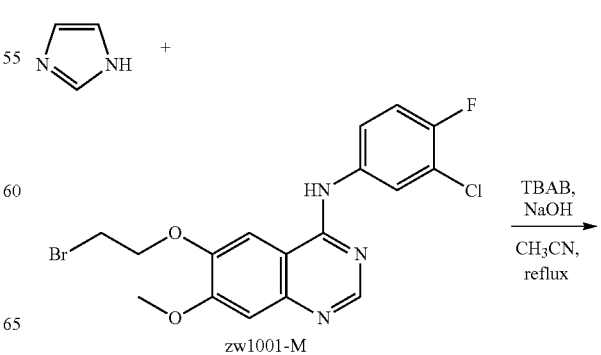

-continued

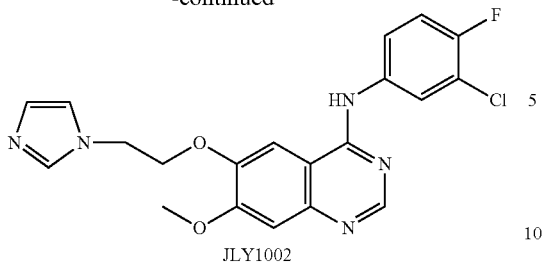
JLY1002

414 mg (6 mmol) imidazole (purchased from Beijing Chemical Reagent Co.), 32 mg TBAB (tetrabutylammonium bromide) (purchased from Beijing Chemical Reagent Co.), and 480 mg NaOH are added to 30 ml of acetonitrile, and the mixture is heated to reflux for 1 hour (temperature of refluxing is 80° C.). 2587 mg (6 mmol) of the intermediate product ZW1001-M prepared in Example 1 is added dropwise, and stirring is continued under reflux for 3 hours, the temperature of refluxing is 80° C. After the reaction is stopped, the solvent is removed by rotary evaporation, 25 mL water and 25 mL of ethyl acetate are added to the residue, a white solid is precipitated between the ethyl acetate and the aqueous layer. The solid is filtered off and washed with water and ethyl acetate, and then the product is dried in vacuum at room temperature for 20 hours to obtain 1.16 g of No. JLY1002 white solid. The yield is 70%.

ESI-MS: m/z 414.7 ([M+H]$^+$); 436.6 ([M+Na]$^+$).

FIG. 3 is the IC$_{50}$ graph of compound No. JLY1002 at IC$_{50}$=60.2 nM under ELISA test conditions, which indicates that this inhibitor has a good inhibitory activity on EGFR protein kinase inhibitor.

Synthesis of Compounds No. JLY2008 and No. JLY2007 of Quinazoline Complex as Protein kinase inhibitor:

The synthetic route is as following:

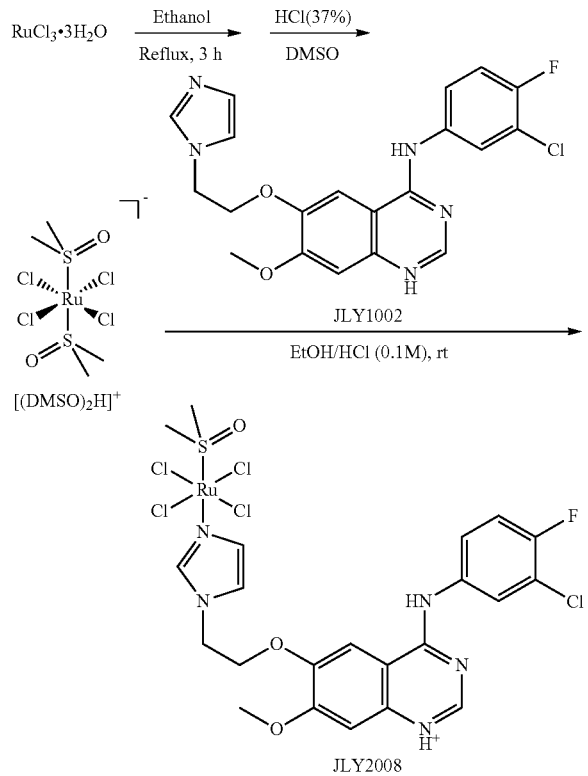
JLY2008

-continued
Synthesis of [trans-RuCl$_4$(Me$_2$SO)$_2$][(Me$_2$SO)$_2$H]:

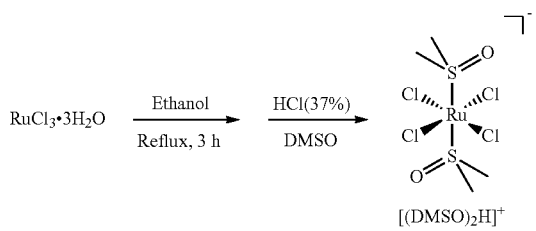

100 mg RuCl$_3$.3H$_2$O is added to 30 ml of ethanol, to form a suspension, and then it is heated to reflux for 3 h (the temperature of refluxing is 80° C.) to form a dark green solution. Potential insoluble solid in the resulting solution is removed through filter paper, and the solution is concentrated by a rotary evaporator to 2 mL. 0.75 mL of aqueous hydrochloric acid (the concentration is 37% by mass percentage) and 1.5 mL DMSO are added to the mixture, then it is allowed to stand for 30 min at 80° C., so as to form a bright orange solution.

The solution obtained above is cooled to room temperature (25° C.), add 10 ml acetone, and orange-red crystal is precipitated from the solution. Adding a small amount of ether may accelerate the precipitation of the crystal. The crystal above is collected by filtration, washed with 20 ml cold acetone solvent at −4° C., and then washed with ether (10 ml), and finally dried under vacuum at room temperature (25° C.).

Synthesis of Compound No. JLY2008:

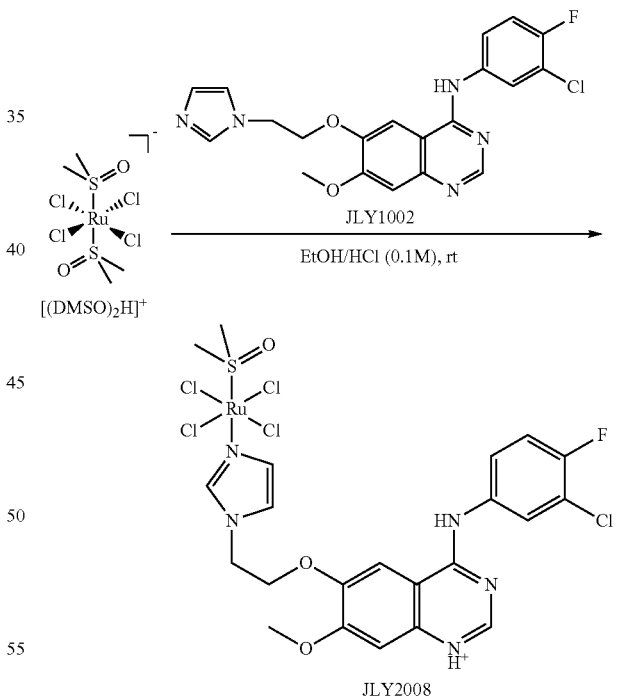
JLY2008

20 mg (0.036 mmol) of the [trans-RuCl$_4$(Me$_2$SO)$_2$][(Me$_2$SO)$_2$H] prepared above is added to 4 mL of ethanol/hydrochloric acid (0.1 m) at room temperature (25° C.), and stirred for 5 min and then 29.8 mg (0.072 mmol) of the quinazoline derivative ligand, No. JLY1002 prepared above is added. Some solid is precipitated after about 10 minutes, and stirring is continued for 4 h. The reaction is stopped, the solution is filtered, and the filter cake is washed successively with water, ethanol and ether, and dried in vacuum. 10.6 mg of yellow product is obtained. The yield is 40%.

ESI-MS (negative): m/z 735.2 [Ru$^{III}$Cl$_4$(DMSO)(L$_2$)]$^-$, 241.8 [Ru$^{III}$Cl$_4$]$^-$. Anal. Calcd for C$_{22}$H$_{24}$Cl$_5$FN$_5$O$_3$RuS (735.86): C, 35.91; H, 3.29; N, 9.52. Found: C, 35.88; H, 3.70; N, 8.93.

Synthesis of Compound No. JLY2007:

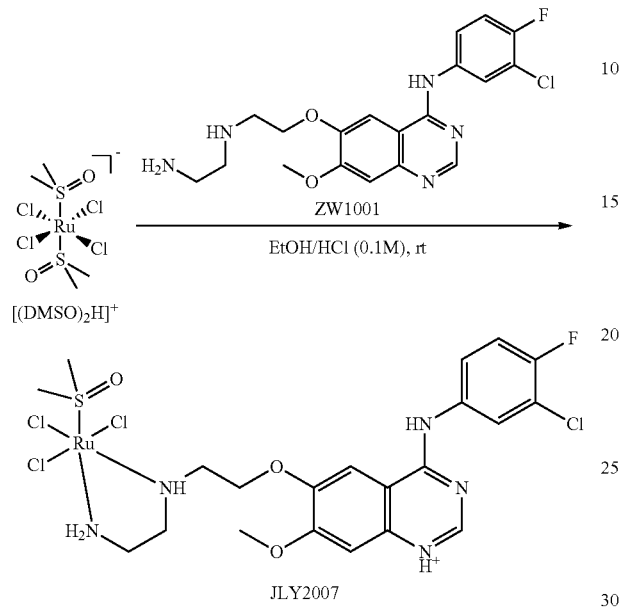

55.6 mg (0.1 mmol) of the [trans-RuCl$_4$(Me$_2$SO)$_2$][(Me$_2$SO)$_2$H] prepared above is added to ethanol (4 mL) at room temperature (25° C.), stirred for 5 min and 40.58 mg (0.1 mmol) of the quinazoline derivative ligand, No. ZW1001, prepared in Example 1 is added. Some solid is precipitated after about 10 minutes, and stirring is continued for 30 mins. Then 4 mL water is added, and stirring is continued for 30 mins. After the reaction is stopped, the solid is filtered off, washed successively with ethanol and ether, and dried in vacuum. 43 mg of yellow product is obtained. The yield is 62%.

Figure 4:
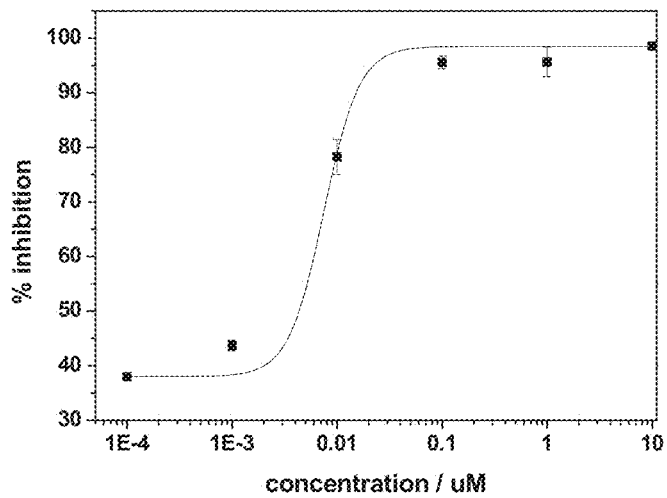
FIG. 4 is the graph of compound No. JLY2007 measured under the condition of ELISA showing $IC_{50}$=7.5 nM.

ESI-MS (positive): m/z 693.1 [Ru$^{III}$Cl$_3$(DMSO)(L5)]$^+$, 615.12 [Ru$^{III}$Cl$_3$(L5)]$^+$, 505.14 [Ru$^{III}$(L5)]$^+$. Anal. Calcd for C$_{21}$H$_{27}$Cl$_4$FN$_5$O$_3$RuS.3H$_2$O (745.46): C, 33.83; H, 4.46; N, 9.39. Found: C, 33.8; H, 4.13; N, 9.18. FIG. 4 is IC$_{50}$ graph of compound No. JLY2007 at IC$_{50}$=7.5 nM measured under ELISA test conditions, showing this inhibitor has a good inhibitory activity on EGFR protein kinase.

Figure 7:
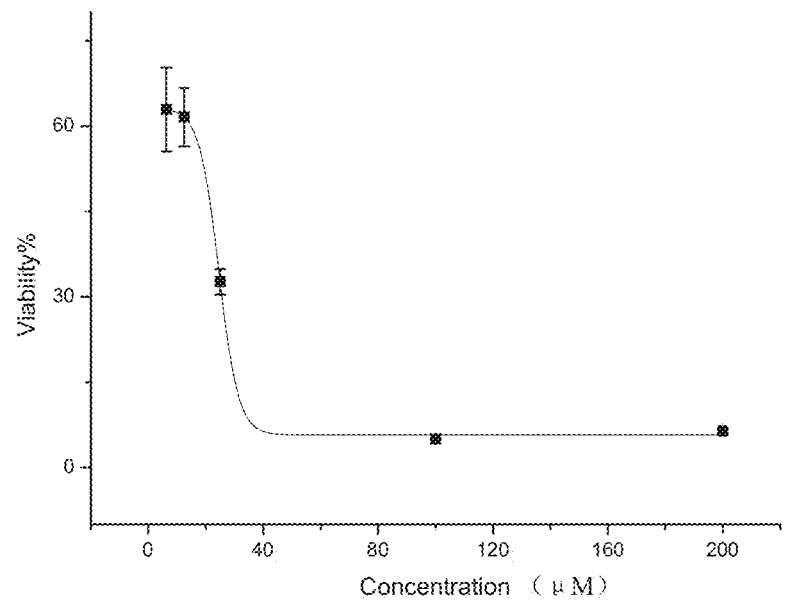
FIG. 7 is the graph of compound No. JLY2007 measured under the test condition of MCF-7/S+EGF inhibiting the proliferation of tumor cells showing $IC_{50}$=24.48 µM.

FIG. 7 is graph of compound No. JLY2007 at IC$_{50}$=24.48 uM measured under test conditions of MCF-7/S+EGF inhibiting tumor cell proliferation. Without EGF, this compound has a IC50>100, virtually no inhibitory activity. When in conjunction with EGF, tumor cell proliferation is greatly suppress, with an IC$_{50}$=24.48 uM. It shows that the inhibitory activity of the compound is associated with EGF, and EGFR may be one of the targets of the compound's action.

Synthesis of Compounds No. JLY2009 of Quinazoline Complex as Protein Kinase Inhibitor:

The synthetic route is as following:

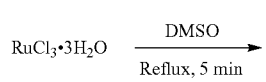

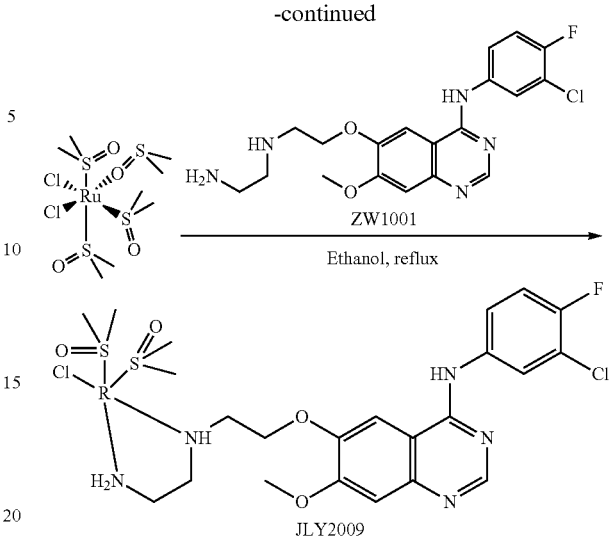

Synthesis of Cis-RuCl$_2$(Me$_2$SO)$_4$:

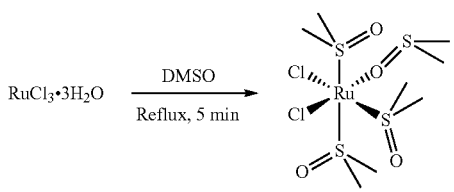

100 mg of RuCl$_3$.3H$_2$O was added to 1 mL of dimethyl sulfoxide, and the mixture is heated to reflux for 5 min (the temperature of refluxing is 189° C.), to get a bright yellow transparent solution. After cooling, 15 mL of acetone is added, the mixture is concentrated to half the original volume by rotary evaporation, and yellow crystal is precipitated. The crystal above is collected by filtration and washed with acetone and ether, and finally dried under vacuum at room temperature (25° C.).

Synthesis of Compounds No. JLY2009:

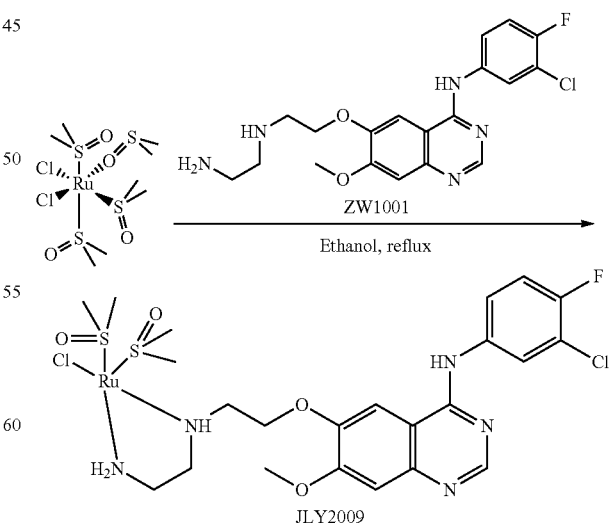

48.5 mg (0.1 mmol) of cis-Ru$^{II}$Cl$_2$(DMSO)$_4$ is added to 10 mL of ethanol, and heated to reflux at 80° C. 40.58 mg (0.1 mmol) of the quinazoline derivative ligand, No. ZW1001 prepared in Example 1 is added, stirring and refluxed is continued at the temperature above for 6 h. Some solid is precipitated and filtered off, washed with ethanol and ether and dried in vacuum. 40 mg of the product JLY2009 is obtained, and the yield is 55%.

ESI-MS (positive): m/z 736.21 [Ru$^{II}$Cl$_2$(DMSO)$_2$(L)]$^+$, 658.17 [Ru$^{II}$Cl$_2$(DMSO)(L)]$^+$, 580.14 [Ru$^{II}$Cl$_2$(L5)]$^+$, 542.15 [Ru$^{II}$Cl(L)]$^+$, 506.17 [Ru$^{II}$(L)]$^+$. $^1$H NMR: (DMSO-d$_6$) δ(ppm): 9.49 (s, 1H), 8.48 (s, 1H), 8.11-8.09 (m, 1H), 7.85 (s, 1H), 7.81-7.77 (m, 1H), 7.45-7.40 (t, 1H), 7.20 (s, 1H), 4.42-4.38 (m, 2H), 4.33-4.30 (m, 1H), 4.24-4.21 (m, 1H), 3.92 (s, 3H), 3.88-3.83 (m, 1H), 3.44-3.37 (m, 1H), 3.29 (s, 6H), 3.23 (s, 3H), 3.12-3.11 (m, 8H).

JLY2009 is dissolved in a mixed solution of DMSO/acetone (volume ratio of 1:5), with ether slowly evaporating into the mixture, and monocrystalline of JLY2009 is precipitated.

FIG. 1-a is X-ray diffraction crystal structure of compound No. JLY2009, and FIG. 1-b is general formula of compound corresponding to it.

Synthesis of platinum based compounds No. ZY-1 and No. ZY-2 of quinazoline complex as protein kinase inhibitor:

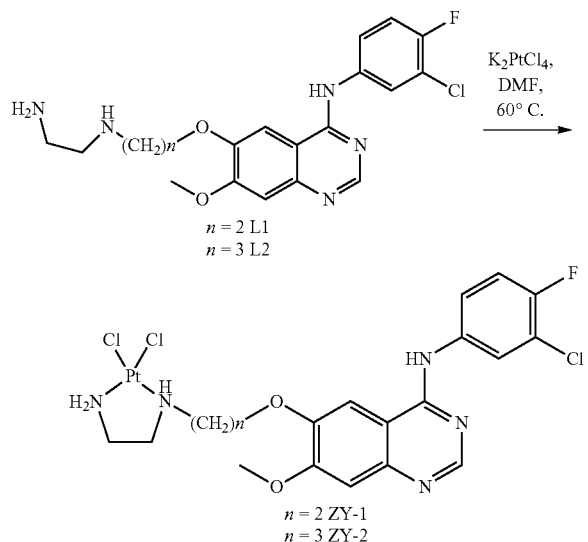

6-(2-(2-aminoethylamino)ethoxy)-4-(3-Chloro-4-fluoro-phenylamino)-7-methoxy quinazoline (L1) (purchased from Shanghai Fluorine Chemical Co. Ltd) or 6-(3-(2-aminoethylamino) propoxy)-4-(3-Chloro-4-fluoro-phenylamino)-7-methoxy quinazoline (L2) (purchased from Shanghai Fluorine Chemical Co. Ltd) (0.24 mmol) is dissolved in 10 ml DMF, dipotassium tetrachloroplatinate (K$_2$PtCl$_4$, purchased from Shenyang Enke Reagent Factory, content of Pt is not less than 46.0%) (0.24 mmol) is dissolved in 5 ml distilled water (purified by Millpore), and the resulted two solution are mixed followed by adding 30 ml DMF, the reaction is carried out at 60° C. for 12 h, and then the reaction is stopped. Most of DMF is removed by rotary evaporator, and then 60 ml distilled water is added into the remaining. The resulted mixture is placed in 4° C. refrigerator overnight then subjected to suction filtration under reduced pressure. The filtration cake is washed successively by methanol, ethanol and ester and then vacuum dried to give the final products.

ZY-1. yellow power, yield 80%.
ESI-MS (m/z): 671 (M$^+$, C$_{19}$H$_{21}$Cl$_3$FN$_5$O$_2$Pt, calc. M.W.=671.84).
$^1$H-NMR (DMSO-d6, 400 MHz) δ(ppm): 8.56 (s, 1H), 8.23 (dd, J=4 Hz, 1H), 8.17 (s, 1H), 7.90-7.95 (m, 1H), 7.43-7.48 (m, 1H), 7.25-7.29 (m, 1H), 4.67-4.43 (m, 3H), 3.96 (s, 3H), 3.65 (s, 1H), 3.52 (s, 1H), 2.93-3.0 (m, 2H), 2.89 (s, 1H), 2.78 (s, 1H), 2.73 (s, 1H), 2.65 (s, 1H).

ZY-2. yellow power, yield 84%.
ESI-MS (m/z): 686 (M$^+$, C$_{20}$H$_{23}$Cl$_3$FN$_5$O$_2$Pt, calc. M.W.=685.86).
$^1$H-NMR (DMSO-d6,400 MHz) δ(ppm): 8.53 (s, 1H), 8.19 (dd, J=4 Hz, 1H), 8.02-8.08 (m, 1H), 7.86-7.91 (m, 1H), 7.45 (t, J$_1$=J$_2$=8 Hz, 1H), 7.23 (s, 1H), 6.25-6.12 (m, 2H), 5.45-5.32 (m, 1H), 3.95 (s, 3H), 3.28-3.17 (m, 2H), 3.12-3.05 (m, 2H), 3.0-2.78 (m, 2H), 2.76-2.66 (m, 2H), 2.32-2.21 (m, 2H).

Example 10

This example is intended to explain the in vitro activity tests on quinazoline derivatives and quinazoline complexes protein kinase inhibitors prepared in Examples 1-9.

I. Enzyme-Linked Immunosorbent Assay (ELISA)

Enzyme-linked immunosorbent assay (ELISA) is used to determine the kinase inhibitory activity of compounds synthesized in Examples 1-9, respectively (the concentration of the compounds synthesized are 40 µM (micromol/L), 4 µM, 400 nM (nanomol/L), 40 nM, 4 nM, 400 µM (picomol/L), 40 µM, 4 µM). Protein kinase assay kit: PTP1B(Tyr66) Biotinylated Peptide from CST company is used as a substrate of kinase EGFR (Epidermal Growth Factor Receptor). The kinase inhibitors of the compounds synthesized by Examples 1-9 were added, respectively, absorbance OD values at a specific wavelength of 450 nm are determined using a Spectramax M5 (USA, Molecular Devices) microplate reader through spectrophotometric method, and cell growth inhibition rates of compounds are calculated according to the following formula, and δ curves are obtained using OriginPro 7.0 data processing software on the basis of cell growth inhibition rate values above. The extent of inhibition of the kinase inhibitors of the compounds synthesized by the present invention on the phosphorylation reaction of the kinase substrates is examined, thus IC50 values (i.e., the concentration value of the kinase inhibitor when the extent of inhibition on the phosphorylation of kinase substrate reaches 50%) are obtained. The experimental result is the average of two independent parallel experiments, typically ±15% change. The physicochemical properties and IC$_{50}$ values from the enzyme activity inhibition test results of each compound are shown in the following Table 1.

$$\text{Growth inhibition rate} = \frac{OD_{kinase} - OD_{tested}}{OD_{kinase} - OD_{blank}} \times 100\%$$

Compounds and compounds numbers tested by ELISA test are as following:

1. LQ1001: LQ1001:C$_{16}$H$_{13}$ClFN$_3$O$_2$, M.W.=333.7

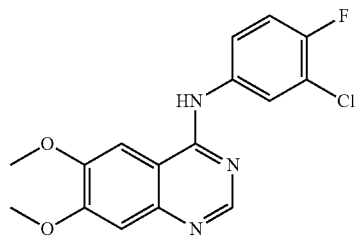 [SMILES: COc1cc2ncnc(Nc3ccc(F)c(Cl)c3)c2cc1OC]

As shown in FIG. 2, IC$_{50}$ of the reference compound, No. LQ1001 is determined to be 4 nM under ELISA testing conditions, indicating a good inhibitor effect on phosphorylation of protein kinase EGFR.

2. JLY1002: $C_{20}H_{17}ClFN_5O_2$, M.W=413.8
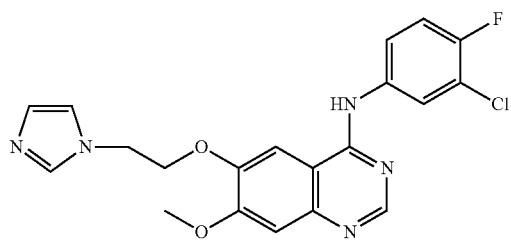 [SMILES: COc1cc2ncnc(Nc3ccc(F)c(Cl)c3)c2cc1OCCn1ccnc1]
6. ZW1001-M: $C_{17}H_{14}BrClFN_3O_2$, M.W=426.7
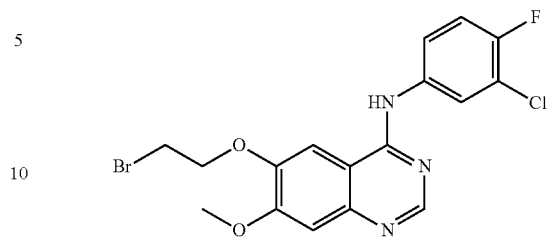
3. JLY2007: $C_{21}H_{27}Cl_4FN_5O_3RuS$, M.W=691.4
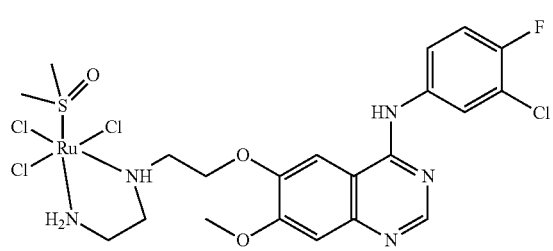
7. ZW1001: $C_{19}H_{21}ClFN_5O_2$, M.W=405.9
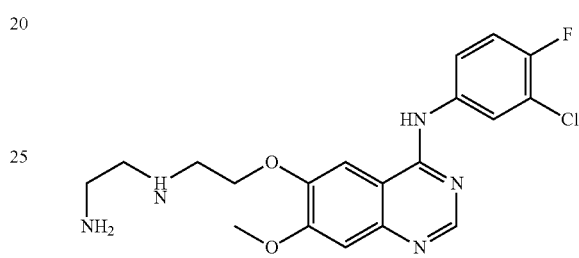
8. ZW1002: $C_{20}H_{23}ClFN_5O_2$, M.W=419.9
4. JLY2008: $C_{22}H_{24}Cl_5FN_5O_3RuS$, M.W=735.8
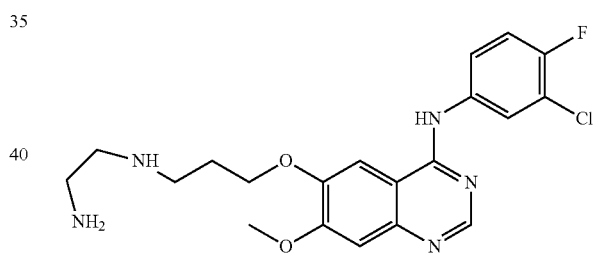
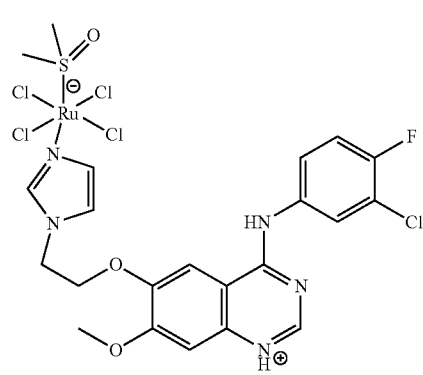
9. ZW2001: $C_{34}H_{49}Cl_2F_7N_5O_2PRu$, M.W=895.7
5. JLY2009: $C_{23}H_{33}Cl_3FN_5O_4RuS_2$, M.W=734.1
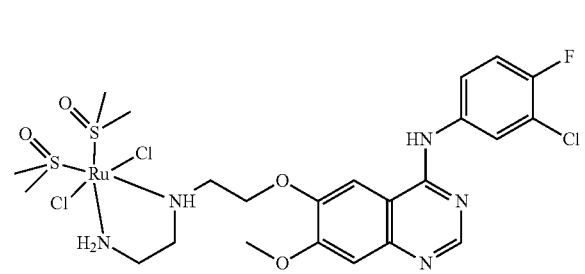
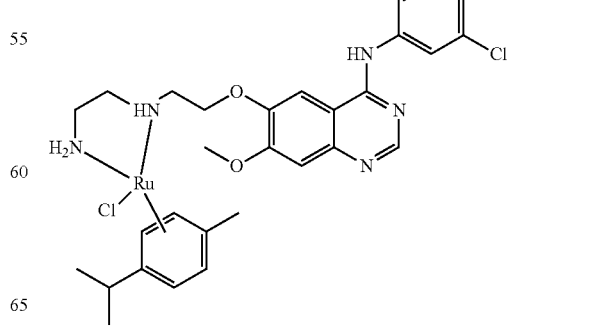

10. ZW2002: $C_{30}H_{41}Cl_2F_7N_5O_2PRu$, M.W=839.6

13. ZW2005: $C_{31}H_{43}Cl_2F_7N_5O_2PRu$, M.W=853.6

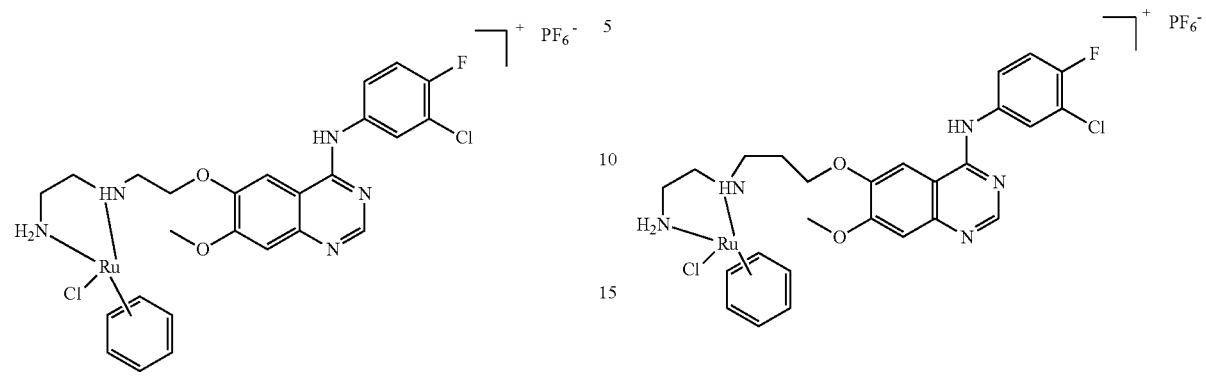

11. ZW2003: $C_{36}H_{45}Cl_2F_7N_5O_2PRu$, M.W=915.7

14. ZW2006: $C_{37}H_{47}Cl_2F_7N_5O_2PRu$, M.W=929.7

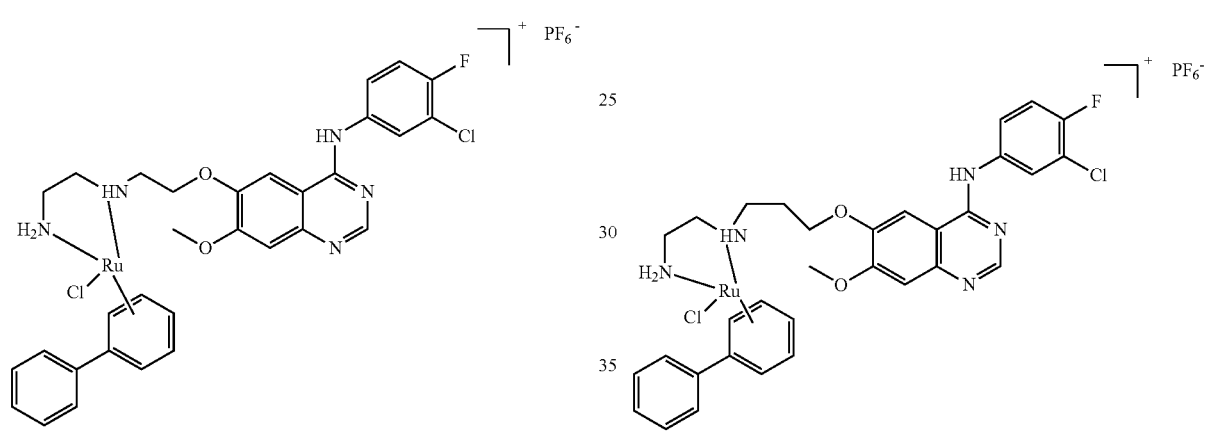

12. ZW2004: $C_{35}H_{51}Cl_2F_7N_5O_2PRu$, M.W=909.8

15. ZY-1: $C_{19}H_{21}Cl_3FN_5O_2Pt$, M.W.=671.84
ZY-2: $C_{20}H_{23}Cl_3FN_5O_2Pt$, M.W.=685.86:

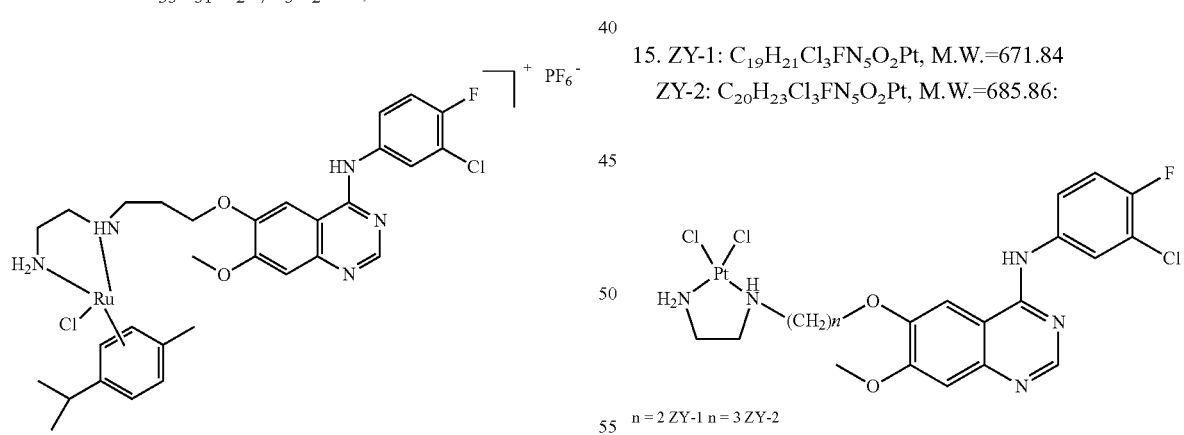

n = 2 ZY-1  n = 3 ZY-2

TABLE 1

| Compound No. | EGFR IC$_{50}$ (nM) | Molecular weight | Stability | Solubility |
|---|---|---|---|---|
| LQ1001 | 4 | 333.7 | Stable in air, photostable | Highly soluble in DMSO, slightly soluble in water, soluble in methanol and ethanol |
| JLY1002 | 60.2 | 413.8 | Stable in air, photostable | Highly soluble in DMSO, slightly soluble in water, soluble in methanol and ethanol |

TABLE 1-continued

| Compound No. | EGFR IC$_{50}$ (nM) | Molecular weight | Stability | Solubility |
|---|---|---|---|---|
| JLY2007 | 7.5 | 691.4 | Stable in air, photostable | Highly soluble in DMSO, slightly soluble in water, soluble in methanol and ethanol |
| JLY2008 | 60.8 | 735.8 | Stable in air, photostable | Highly soluble in DMSO, slightly soluble in water, soluble in methanol and ethanol |
| JLY2009 | 283 | 734.1 | Stable in air, photostable | Highly soluble in DMSO, slightly soluble in water, soluble in methanol and ethanol |
| ZW1001-M | 18 | 426.7 | Stable in air, photostable | Highly soluble in DMSO, slightly soluble in water, soluble in methanol and ethanol |
| ZW1001 | 4.6 | 405.9 | Stable in air, photostable | Highly soluble in DMSO, slightly soluble in water, soluble in methanol and ethanol |
| ZW1002 | 7.2 | 419.9 | Stable in air, photostable | Highly soluble in DMSO, slightly soluble in water, soluble in methanol and ethanol |
| ZW2001 | 81 | 895.7 | Stable in air, photostable | Highly soluble in DMSO, slightly soluble in water, soluble in methanol and ethanol |
| ZW2002 | 93.8 | 839.6 | Stable in air, photostable | Highly soluble in DMSO, slightly soluble in water, soluble in methanol and ethanol |
| ZW2003 | 126.4 | 915.7 | Stable in air, photostable | Highly soluble in DMSO, slightly soluble in water, soluble in methanol and ethanol |
| ZW2004 | 106.1 | 909.7 | Stable in air, photostable | Highly soluble in DMSO, slightly soluble in water, soluble in methanol and ethanol |
| ZW2005 | 174.4 | 853.6 | Stable in air, photostable | Highly soluble in DMSO, slightly soluble in water, soluble in methanol and ethanol |
| ZW2006 | 76.2 | 929.7 | Stable in air, photostable | Highly soluble in DMSO, slightly soluble in water, soluble in methanol and ethanol |
| ZY-1 | 2.8 | 671.84 | Stable in air, photostable | Highly soluble in DMSO, slightly soluble in water, soluble in methanol and ethanol |
| ZY-2 | 16.99 | 685.86 | Stable in air, photostable | Highly soluble in DMSO, slightly soluble in water, soluble in methanol and ethanol |

In the table above,
"highly soluble in DMSO" means, at room temperature and under atmospheric pressure, the solubility in DMSO is not less than 1.0 gram;
"slightly soluble in water" means, at room temperature and under atmospheric pressure, the solubility in water is 0.09-0.10 g,
"soluble in methanol and ethanol" means, at room temperature and under atmospheric pressure, the solubility in methanol is 1.0-9.9 grams, the solubility in ethanol is 1.0-9.9 g.

As can be seen from the results in Table 1 above, quinazoline derivatives and their quinazoline complexes with ruthenium or platinum provided by the present invention have shown good inhibitory activity on protein kinase epidermal growth factor receptor (EGFR).

II. Experiments on Effect on Proliferation of a Variety of Tumor Cells:

1. Cytotoxicity Experiment

Human breast cancer cell line (drug-resistant) MCF-7/A, human breast cancer cell line (sensitive) MCF-7/S, prostate cancer cell PC-3, keratinocyte Colo-16, human non-small cell lung cancer cell line A549 and etc. are cultured in RPMI1640 medium (Invitrogen, USA) containing 10 wt % fetal bovine serum (FBS, Hyclone, USA), and epidermal growth factor (EGF) at a concentration of 100 ng/ml is added to stimulate growth. After 2-3 days, cells in logarithmic growth phase are collected, and inoculated at 96 well plates (6500 cells/well/100 ul, RPMI1640 containing 100 ng/mL EGF) for 24 h, and then compound at gradient concentrations (200, 100, 50, 25, 12.5, 6.25, 1 μM/L) are added. The same volume of RPMI1640 containing 1 wt % of dimethyl sulfoxide (DMSO) is used as control group of the experiment; the blank group is only culture medium without cell. Three parallel wells are set up for each concentration group. After incubation is continued for 48 h, the cell survival rate is measured by SRB method. Results are shown in Table 2 and Table 3, respectively.

2. Cytotoxicity Experiment Under the Condition of Additional EGF

Human breast cancer cell line (sensitive) MCF-7/S and human non-small cell lung cancer cell line A549 are cultured in HAM'S/F-12 medium (HyClone, USA) containing 10 wt % fetal bovine serum (FBS, Hyclone, USA), and 100 ng/ml epidermal growth factor (EGF, Sigma, USA) is added to this medium. Cells described above were purchased from Cell Resource Center, Shanghai Institute for Biological Science, CAS, they are placed in a CO$_2$ incubator and used for the experiment 3-5 days later. The results are shown in Table 2.

Wherein, for experiment on compound cytotoxicity assay by sulforhodamine B (SRB) method: Cells in the logarithmic growth phase are collected and inoculated at 96-well plates (6500 cells/well/100 ul, RPMI1640 containing 100 ng/ml of EGF). After incubation for 24 h, compounds at gradient concentrations (200, 100, 50, 25, 12.5, 6.25, 1 (μM/L)) are added. The same volume of RPMI1640 containing 100 ng/ml of EGF is used as control group of the experiment; the blank group is only culture medium without cell. Three parallel wells are set up for each concentration group. After incubation is continued for 48 h, the cell survival rate is measured by SRB method. 50 μl 10% trichloroacetic acid (TCA) pre-cooled (4° C.) is added to each well, it is fixed for 1 hour at 4° C., washed with water for five times, and completely dried, and then 100 μl of SRB solution (Sigma, USA) at concentration of 0.4% by weight is added, and staining is performed at 37° C. in the dark for 30 min. Wash with acetic acid at a concentration of 1% by weight for 4-5 times, dry in the air, add 200 μl of Tris solution (10 mM, pH 10.5), after sufficiently dissolved, the absorbance (absorption wavelength is 570 nm) is measured in microplate reader.

The growth inhibition rate (IR) is calculated according to the following formula: IR (%)=[1−(experiment group A value−blank group A value)/(control group A value−blank group A value)]×100%, and the $IC_{50}$ value is calculated using Origin 6.0 software.

Note:

Positive control 1: LQ1001, protein kinase inhibitor, molecular targeted drug.

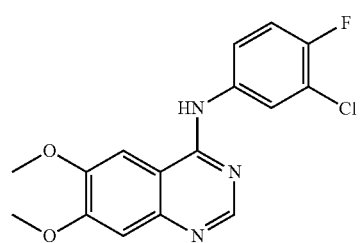 [SMILES: COc1cc2ncnc(Nc3ccc(F)c(Cl)c3)c2cc1OC]

Positive control 2: Pcy-Ru, metal type antineoplastic agent, cytotoxic antineoplastic agent.

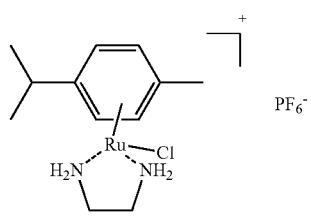

Positive control 3: Taxol, cytotoxic antineoplastic agent.

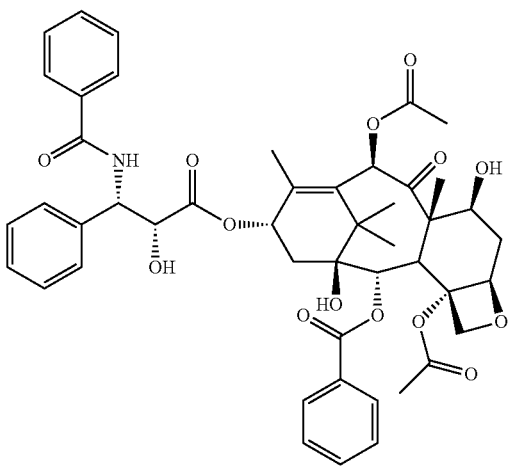 [SMILES: CC(=O)O[C@H]1C(=O)[C@@]2(C)C([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Positive control: NAMI-A, metal type antineoplastic agent.

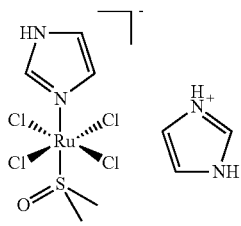

TABLE 2

Human breast cancer cell line (drug-resistant) MCF-7/A, human breast cancer cell line (sensitive) MCF-7/S and MCF-7/S + EGF.

| $IC_{50}$ (umol/L) | Breast cancer cell (drug-resistant) MCF-7/A | Breast cancer cell (sensitive) MCF-7/S | Breast cancer cell (sensitive) MCF-7/S + EGF |
|---|---|---|---|
| JLY1002 | >100 | >100 | >100 |
| JLY2007 | >100 | >100 | 24.48 ± 0.42 |
| JLY2008 | >100 | >100 | >100 |
| JLY2009 | 59.67 ± 2.18 | >100 | >100 |
| Positive control NAMI-A | >100 | >100 | >100 |
| ZW1001 | >100 | 38.34 ± 0.10 | 36.30 ± 5.77 |
| ZW1002 | >100 | 16.39 ± 0.62 | 15.93 ± 1.15 |
| ZW2001 | >100 | >100 | 56.11 ± 2.66 |
| ZW2002 | >100 | >100 | >100 |
| ZW2003 | >100 | 79.06 ± 11.60 | 28.70 ± 8.75 |
| ZW2004 | >100 | 86.78 ± 6.66 | 33.87 ± 1.39 |
| ZW2005 | >100 | >100 | 17.41 ± 1.09 |
| ZW2006 | >100 | 48.84 ± 7.82 | 21.67 ± 7.44 |
| Positive control 1 LQ1001 | >100 | >100 | 53.30 ± 3.12 |
| Positive control 2 Pcy-Ru | >100 | 13.00 ± 3.37 | 21.83 ± 1.73 |
| Positive control 3 Taxol | 0.44 ± 0.50 | 0.026 ± 0.98 | 0.029 ± 0.09 |

TABLE 3

Prostate cancer cell PC-3, keratinocyte Colo-16, non-small cell lung cancer cell A549.

| $IC_{50}$ (μmol/L) | Prostate cancer cell PC-3 | Keratinocyte Colo-16 | Non-small cell lung cancer cell A549 |
|---|---|---|---|
| JLY1002 | >100 | >100 | 48.25 ± 0.51 |
| JLY2007 | >100 | >100 | >100 |
| JLY2008 | >100 | >100 | — |
| JLY2009 | >100 | >100 | >100 |
| Positive control NAMI-A | >100 | >100 | — |
| ZW1001 | 38.36 ± 2.36 | >100 | 51.04 ± 1.02 |
| ZW1002 | 13.6 ± 0.85 | 14.49 ± 0.37 | 57.41 ± 1.98 |
| ZW2001 | >100 | 42.78 ± 2.46 | >100 |
| ZW2002 | >100 | 42.08 ± 2.55 | >100 |
| ZW2003 | 81.33 ± 6.94 | 54.25 ± 4.98 | >100 |
| ZW2004 | 79.90 ± 7.44 | 58.19 ± 1.49 | — |
| ZW2005 | 38.29 ± 3.56 | 39.80 ± 4.85 | 45.09 ± 2.34 |
| ZW2006 | 43.84 ± 3.90 | 55.76 ± 1.55 | >100 |
| Positive control 1 Iressa-LQ1001 | >100 | 88.22 ± 3.98 | >100 |
| Positive control 2 Pcy-Ru | >100 | 14.29 ± 1.50 | 17.27 ± 0.76 |
| Positive control 3 Taxol | 0.74 ± 0.18 | 1.06 ± 0.31 | 4.07 ± 1.63 |

As can be seen from the results in Table 2 and Table 3 above, quinazoline derivatives and quinazoline complexes as protein kinase inhibitors provided by the present invention have shown good inhibitory activity on proliferation of various tumor cell types including human breast cancer cell lines (drug-resistant) MCF-7/A, human breast cancer cell line (sensitive) MCF-7/S, prostate cancer cell PC-3, keratinocytes Colo-16, and non-small cell lung cancer cell line A549. Moreover, in the presence of additional epidermal growth factor (EGF), said compounds have shown even better inhibitory activity on proliferation of cells which excessively express epidermal growth factor receptor (EGFR) (such as human breast cancer cell lines (sensitive) MCF-7/S), which indicates that EGFR (a protein tyrosine kinase) is one of the target through which quinazoline derivatives and quinazoline complexes as protein kinase inhibitors provided by the present invention inhibit tumor cell proliferation.

The invention claimed is:

1. A quinazoline complex as protein kinase inhibitor, formed by coordinating a coordination compound containing noble metal and a ligand capable of coordinating with the noble metal in the coordination compound, wherein said ligand is quinazoline having a molecular structure represented by formula (1):

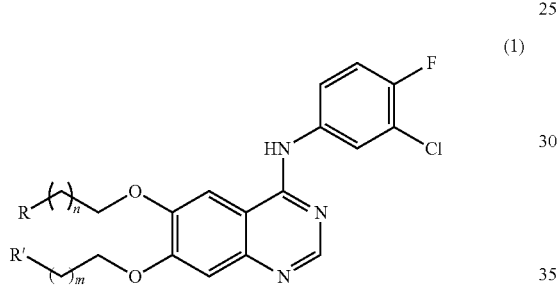

(1)

wherein m is 0, R' is hydrogen, and R is a group containing at least one atom capable of coordinating with noble metals and is any one selected from the group consisting of a fused heterocyclic imino or substituted fused heterocyclic imino, an aminoalkyl imino, a group having an imidazole type five-membered heterocyclic structure and on the ring a tertiary amino group, and a six-membered aromatic heterocyclic imino or substituted six-membered aromatic heterocyclic imino, where a nitrogen in said imino or tertiary amino group bonds to the 6-oxygen of the alkyl chain, and n is an integer from 0 to 5; alternatively, both R and R' are —NH$_2$; n is an integer from 1 to 3, and m is an integer from 1 to 3; and wherein the noble metal is ruthenium and/or platinum.

2. The quinazoline complex as protein kinase inhibitor according to claim 1, wherein the number of said atom capable of coordinating with noble metal in R is 1-3.

3. The quinazoline complex as protein kinase inhibitor according to claim 1, wherein said fused heterocyclic imino or substituted fused heterocyclic imino has the structure shown by any one of general formulae (2)-(7), said aminoalkyl imino has the structure shown by general formula (8), said group having on the ring a tertiary amino group and imidazole type five-membered heterocyclic structure has the structure shown by general formula (9), said six-membered aromatic heterocyclic imino or substituted six-membered aromatic heterocyclic imino has the structure shown by general formulae (10)-(14):

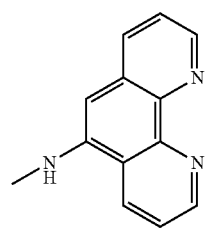
(2)

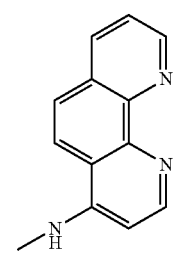
(3)

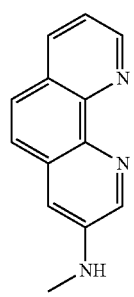
(4)

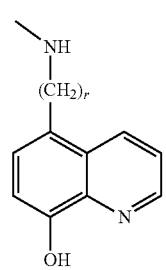
(5)

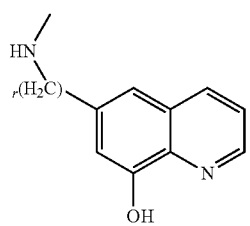
(6)

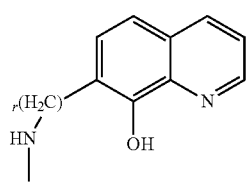
(7)

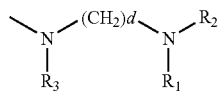
(8)

-continued

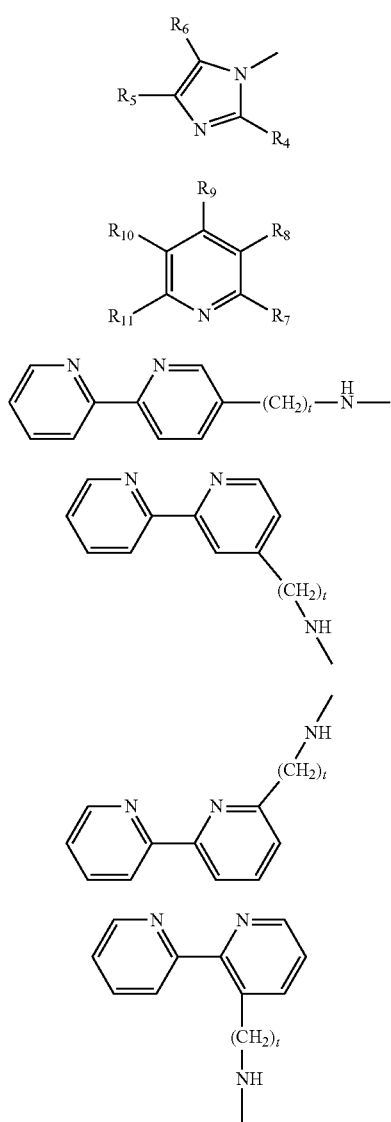

wherein r, d and t represent number of alkylidene in each general formula, and are integer from 1 to 3, from 2 to 5 and from 0 to 3, respectively; $R_1$, $R_2$, $R_3$, $R_4$, $R_5$ and $R_6$ each independently are any one of hydrogen atom and C1-C3 alkyl group; $R_7$, $R_8$, $R_9$, $R_{10}$ and $R_{11}$ each independently are any one of hydrogen atom, imino and C1-C3 alkyl group, and at least one group among $R_7$, $R_8$, $R_9$, $R_{10}$ and $R_{11}$ is an imino.

4. The quinazoline complex as protein kinase inhibitor according to claim 3, wherein said R is any one of groups represented by general formulae (2), (16)-(20);

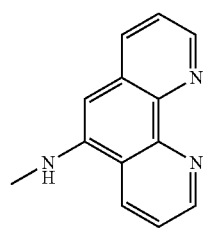

-continued

(16)
(17)
(18)
(19)
(20)

5. The quinazoline complex as protein kinase inhibitor according to claim 1, wherein,
said quinazoline complex as protein kinase inhibitor is represented by AG(X'Y')Z, wherein, X'Y' is group formed by the quinazoline shown by the general formula (1), wherein, m is 0, R' is hydrogen, R is fused heterocyclic imino or substituted fused heterocyclic imino represented by any one of general formulae (5)-(7); and nitrogen of said imino bonds to the 6-oxygen of alkyl chain in general formula (1);
alternatively, said quinazoline complex as protein kinase inhibitor is represented by general formula [AG(XY)Z]$^+$ B$^-$, wherein, XY is a group formed by the quinazoline represented by general formula (1), wherein, m is 0, R' is hydrogen, R is any one of fused heterocyclic imino or substituted fused heterocyclic imino represented by the general formulae (2)-(4) and aminoalkyl imino represented by general formula (8) as well as six-membered aromatic heterocyclic imino or substituted six-membered aromatic heterocyclic imino represented by general formulae (11)-(14), and nitrogen on said imino bonds to the 6-oxygen of the alkyl chain in general formula (1); alternatively, R and R' are —NH$_2$; n is an integer from 1 to 3, m is an integer from 1 to 3; Z is a group selected from halogen, —SCN, —N$_3$ and —CN; A is one selected from benzene, biphenyl, isopropyl toluene and benzo-cyclane; B is Cl$^-$, PF$_{6-}$ or BF$_{4-}$; alternatively, said quinazoline complex as protein kinase inhibitors is represented by general formula [AG(X1Y1)Z1]$^+$B$^-$, wherein, X1Y1 is an alkyl diamine of 1-5 carbon atoms, Z1 is group formed by the quinazoline represented by formula (1), wherein, m is 0, R' is hydrogen, R is any one of group having on the ring a tertiary amino group and imidazole type five-membered heterocyclic structure represented by general formula (9) and six-membered aromatic heterocyclic imino or substituted six-membered aromatic heterocyclic imino represented by general formula (10), and nitrogen on said imino or tertiary amino group bonds to the 6-oxygen of the alkyl chain in general formula (1); alternatively, said quinazoline complex as protein kinase inhibitor is represented by G(M)W, wherein, M is group formed by the quinazoline represented by general formula (1), wherein, m is 0, R' is hydrogen, R is any one of fused heterocyclic imino or substituted fused heterocyclic imino represented by general formulae (2)-(7), aminoalkyl imino represented by general formula (8), group having on the ring a tertiary amino group and imidazole type five-membered heterocyclic structure represented by general formula (9), six-membered aromatic heterocyclic imino or substituted six-membered aromatic heterocyclic imino represented by any of general formulae (10)-(14), W is at least one selected from halogen and DMSO; G is ruthenium or platinum; nitrogen on said fused heterocycle and oxygen on hydroxyl group coordinate with G, or two nitrogen atoms on said fused heterocycle coordinate with G; alternatively, two nitrogen atoms on aminoalkyl imino coordinate with G; alternatively, two nitrogen atoms on said six-membered aromatic heterocycle coordinate with G; alternatively, nitrogen on said R and R' coordinates with G; alternatively, nitrogen atoms on said imidazole type five-membered heterocyclic structure except those on tertiary amino group coordinate with G; alternatively nitrogen atom on said six-membered heterocycle coordinates with G.

6. The quinazoline complex as protein kinase inhibitor according to claim 5, wherein
for general formula AG(X'Y')Z, X'Y' is group formed by the quinazoline shown by the general formula (1), R is structure shown by formula (16); Z is halogen; G is ruthenium;
for general formula [AG(XY)Z]$^+$B$^-$, XY is represented by general formula (1), R is structure represented by formula (2), formula (17), or formula (20); Z is halogen; G is ruthenium;
for general formula [AG(X1Y1)Z1]$^+$B$^-$, Z1 is represented by formula (1), R is structure represented by formula (18) or formula (19); X1Y1 is alkyl diamine of 1-2 carbon atoms; G is ruthenium;
for general formula G(M)W, M is represented by general formula (1), R is structure represented by formula (17); W is halogen and DMSO; G is ruthenium or platinum.

7. Preparation method for the quinazoline complex as protein kinase inhibitor according to claim 1, comprising coordinating coordination compound containing noble metal with ligand, said ligand is a quinazoline prepared by following steps:
providing a first reactant A represented by formula (a), in which $R_{100}$ and $R_{101}$ are either the same or different, independently selected from hydrogen or methyl group, and wherein at least one of $R_{100}$ and $R_{101}$ is hydrogen;
substituting hydrogen or methyl group at position $R_{100}$ in formula (a) with group shown by formula (Q1), and/or substituting hydrogen or methyl group at position $R_{101}$ in formula (a) with group shown by formula (Q2), said $R_{100}$ and $R_{101}$ are either the same or different, independently selected from hydrogen or methyl group; R is a group containing an atom capable of coordinating with noble metal, and m is 0, R' is hydrogen, and R is any one selected from the group consisting of fused heterocyclic imino or substituted fused heterocyclic imino, aminoalkyl imino, group having on the ring a tertiary amino group and imidazole type five-membered heterocyclic structure, six-membered aromatic heterocyclic imino or substituted six-membered aromatic heterocyclic imino, and nitrogen in said imino or tertiary amino group bonds to the 6-oxygen of the alkyl chain, n is an integer from 0 to 5; alternatively, both R and R' are —NH$_2$; n is integer from 1 to 3, m is an integer from 1 to 3; wherein noble metal is ruthenium and/or platinum;

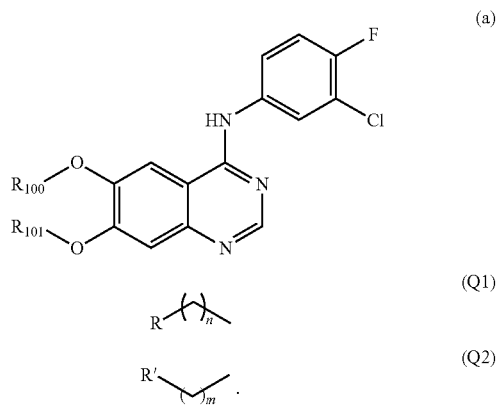

8. The preparation method according to claim 7, wherein the number of said atoms capable of coordinating with noble metal in R is 1-3.

9. The preparation method according to claim 7, wherein $R_{100}$ is hydrogen, $R_{101}$ is methyl, said substituting hydrogen in formula (a) with group shown in formula (Q1) includes:

means (I):
(1) in the presence of a first organic solvent, the first reactant A is allowed to contact and react with dihaloalkane represented by the formula (k) below to produce the intermediate product B represented by the formula (b) below, wherein, X, $X_1$, X2 all represent halogen atom;

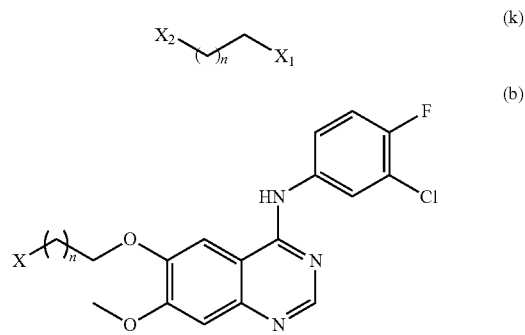

(2) in the presence of a second organic solvent and under condensation reaction conditions, intermediate product B obtained in step (1) is heated with a first organic amine containing atom capable of coordinating with noble metal to reflux so as to allow halogen atom of 6-haloalkoxy in intermediate product B to undergo condensation reaction with said first organic amine;

means (II):
(1) in the presence of a first organic solvent, the first reactant A is allowed to contact and react with a halogenated carboxylic ester represented by the following formula (1), so as to generate the intermediate product C represented by the following formula (c), wherein, X represents a halogen atom;

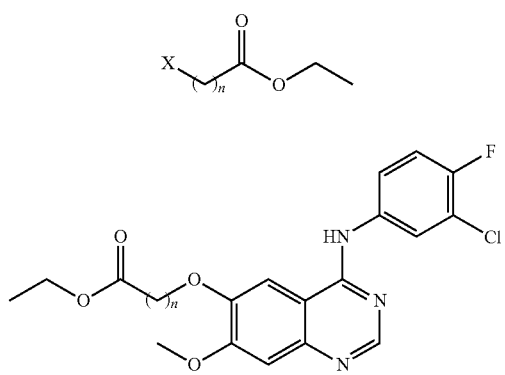

(2) catalyzed by alkali, the intermediate product C obtained in step (1) is hydrolyzed, to obtain the intermediate D represented by the following formula (d), the intermediate product D is allowed to undergo halogenation reaction to obtain an intermediate product E represented by the following formula (e) below; said intermediate product E is allowed to contact and react with a second organic amine, which is compound containing group with coordinating function under conditions allowing halogen atom in 6-alkoxy acyl halide of the intermediate product E to undergo condensation reaction with the second organic amine, so as to obtain condensation product F represented by the following formula (f);

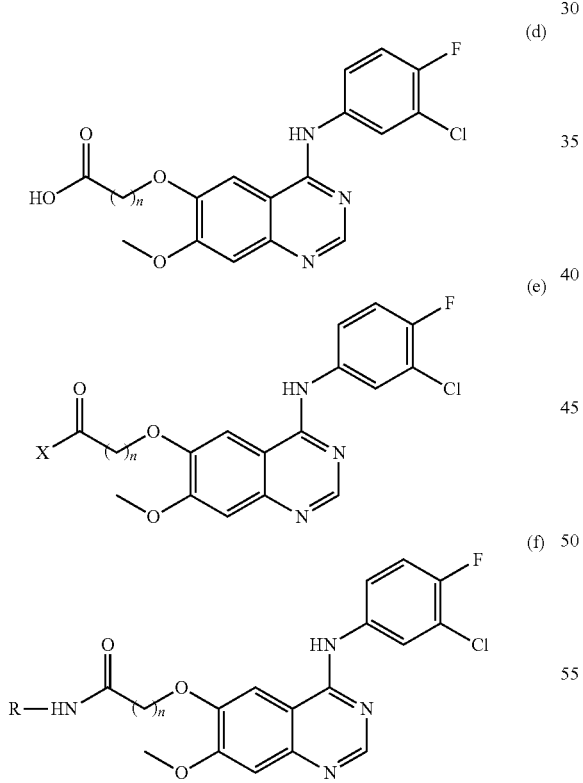

(3) carbonyl group of 6-alkoxy amide in the condensation product F obtained in step (2) is reduced to alkylene group.

10. The preparation method according to claim 9, wherein in means (I), said first organic amine is any one selected from the group consisting of alkyl diamine or substituted alkyl diamines and compound having on the ring a tertiary amino group and imidazole type five-membered heterocyclic structure; in means (II), said second organic amine is any one selected from the group consisting of fused heterocyclic group-substituted amine or substituted fused heterocyclic substituted amine and six-membered aromatic heterocyclic group-substituted amine or substituted six-membered aromatic heterocyclic substituted amine.

11. The preparation method according to claim 10, wherein said fused heterocyclic group-substituted amine or substituted fused heterocyclic substituted amine is represented by general formulae (21)-(26), said compound having on the ring a tertiary amino group and imidazole type five-membered heterocyclic structure is represented by general formula (27), six-membered aromatic heterocyclic group-substituted amine or substituted six-membered aromatic heterocyclic substituted amine is represented by general formulae (28)-(32), said alkyl diamine or substituted alkyl diamine is represented by formula (33):

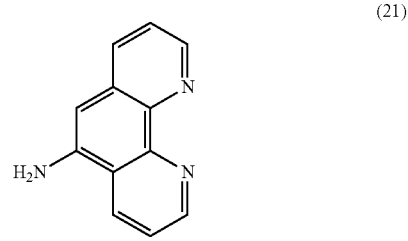

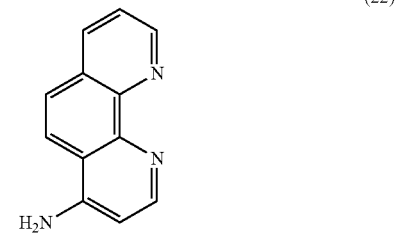

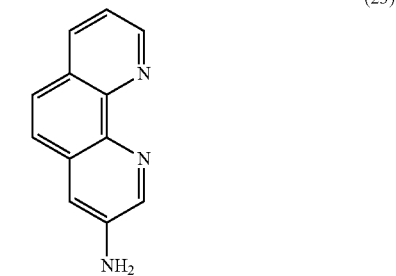

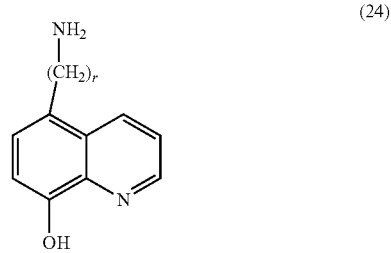

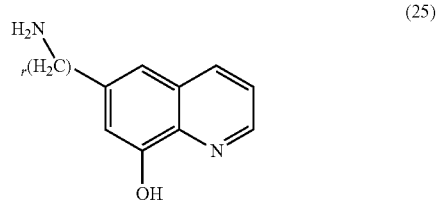

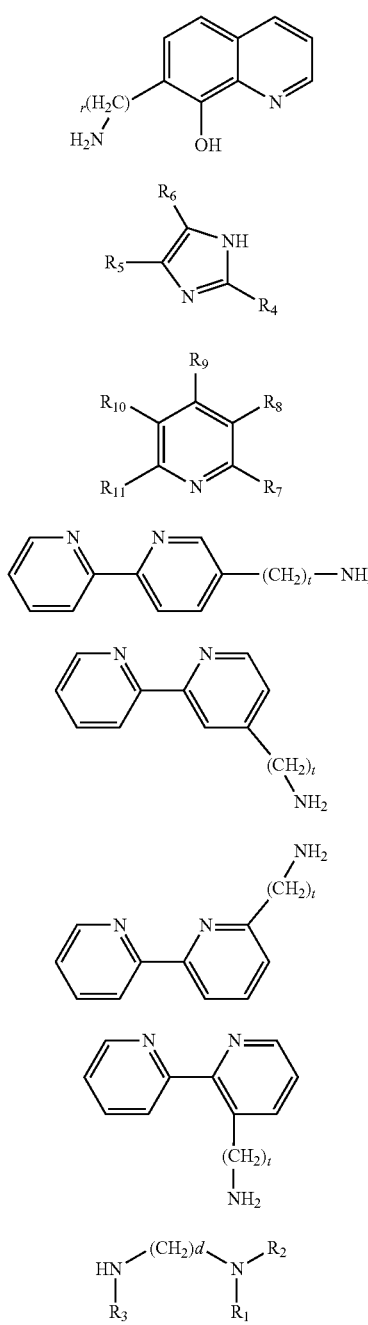

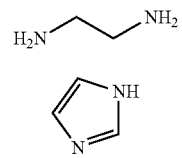

(34)

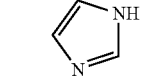

(35)

(21)

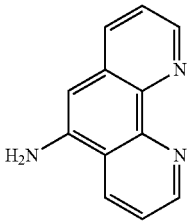

(37)

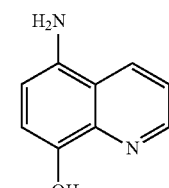

(38)

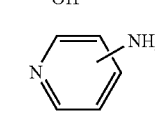

(39)

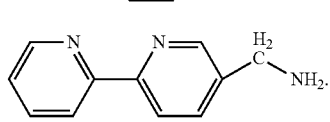

wherein r, d and t represent number of alkylidene in each general formula, and are integer from 1 to 3, from 2 to 5 and from 0 to 3, respectively; $R_1$, $R_2$, $R_3$, $R_4$, $R_5$ and $R_6$ each independently are any one selected from the group consisting of hydrogen atom and C1-C3 alkyl group; $R_7$, $R_8$, $R_9$, $R_{10}$ and $R_{11}$ each independently are any one selected from the group consisting of hydrogen atom, imino and C1-C3 alkyl group, and at least one among $R_7$, $R_8$, $R_9$, $R_{10}$ and $R_{11}$ is an imino.

12. The preparation method according to claim 9, wherein said first organic amine is the compounds as such shown in formulae (34) to (35); said second organic amine is any one of compounds as such shown in formulae (21) and (37) to (39):

13. The preparation method according to claim 9, wherein in means (I):
  (1) the conditions of allowing the first reactant A to contact and react with dihaloalkane include, the reaction temperature is 50-100° C., the reaction time is 1-10 hours, the molar ratio of the first reactant A to dihaloalkane is 1: (3-8), on the basis that the total amount of the first reactant A and dihaloalkane is 1000 mg, the amount of said first organic solvent used is 4-20 mL;
  (2) the temperature for heating the intermediate product B obtained in step (1) with a first organic amine to reflux is 50-95° C., the time of the same is 1-10 hours, the molar ratio of intermediate product B to the first organic amine is 1: (1-10); on the basis that the total amount of the intermediate product B and the first organic amine is 1000 mg, the amount of the second organic solvent used is 10-60 mL.

14. The preparation method according to claim 13, wherein in step (1), the reaction between the first reactant A and dihaloalkane is performed in the presence of acid binding agent, the molar ratio of said acid binding agent to the first reactant A is (3-8): 1; in step (2), the heating to reflux of the intermediate product B and the first organic amine is performed in the presence of acid binding agent, the molar ratio of said acid binding agent to the first organic amine is (3-8): 1.

15. The preparation method according to claim 13, wherein said dihaloalkane is one or more selected from the group consisting of dihalo ethane, dihalo propane, dihalo butane and dihalo pentane.

16. The preparation method according to claim 9, wherein in means (II):

(1) the conditions of allowing the first reactant A to contact and react with halogenated carboxylic ester include, the reaction temperature is 10-60° C. the reaction time is 0.3-5 hours, the molar ratio of first reactant A to halogenated carboxylic ester is 1: (1-1.5), on the basis that the total amount of the first reactant A and halogenated carboxylic ester is 1000 mg, the amount of said first organic solvent used is 10-20 mL;

(2) the conditions for hydrolyzing intermediate product C obtained in step (1) with catalyzation by alkali include, the temperature is 20-60° C., the time is 1-15 hours, the amount of alkali used is 3-5 times the amount of substance of the intermediate product C obtained in step (1), the performance for halogenation reaction of the intermediate product D comprises allowing intermediate product D to contact and react with thionyl chloride under the conditions that the reaction temperature is 25-75° C., the reaction time is 1-5 hours, the amount of thionyl chloride used is 5-15 times the amount of substance of intermediate product D; the reaction between the intermediate product E and the second organic amine is carried out in the presence of a third organic solvent under the conditions that the reaction temperature is 3-30° C., the reaction time is 2-8 hours, the molar ratio of said intermediate product E to the third reactant, i.e., the second organic amine, is 1: (1-2);

(3) performance of reducing the carbonyl group in 6-alkoxy amide of the condensation product F obtained in step (2) in the presence of a fourth organic solvent amide reduction, comprises heating the sodium borohydride together with the condensation product F to reflux under the temperature of 40-60° C. and the time of 6-20 hours, the amount of sodium borohydride used of 2-4 times the amount of the substance of condensation product F.

17. The preparation method according to claim 16, wherein in step (1), the reaction between the first reactant A and halogenated carboxylic ester is performed in the presence of acid binding agent, the molar ratio of said acid binding agent to the first reactant A is (2-5): 1; the reaction between intermediate product E and the second organic amine is performed in the presence of acid binding agent, the molar ratio of said acid binding agent to intermediate product E is (2-5): 1.

18. The preparation method according to claim 16, wherein said halogenated carboxylic ester is one or more selected from the group consisting of halogenated ethyl acetate, halogenated methyl acetate and halogenated ethyl pyruvate.

19. The preparation method according to claim 9, wherein said first organic solvent and the second organic solvents are one or more each independently selected from the group consisting of N,N-dimethyl formamide (DMF) and acetonitrile.

20. The preparation method according to claim 16, wherein the third organic solvent is methylene chloride and/or chloroform, on the basis that the total amount of the intermediate E and the second organic amine is 1000 mg, amount of said third organic solvent used is 30-60 mL; the fourth organic solvent is THF and/or dioxane, on the basis that the total amount of the sodium borohydride and the condensation product of F is 1000 mg, the amount of the fourth organic solvent is 50-80 mL.

21. The preparation method according to claim 14, wherein said acid binding agent is one or more selected from the group consisting of $K_2CO_3$, $CsCO_3$, NaOH and triethylamine.

22. The preparation method according to claim 7, wherein when $R_{100}$ is hydrogen and $R_{101}$ is methyl, the performances of substituting hydrogen at $R_{100}$ position of formula (a) with the group shown by formula (Q1) and of substituting methyl at $R_{101}$ position of formula (a) with the group shown by formula (Q2) comprises:

(1) under the protection of inert gas, allowing the first reactant A to the contact and react with molten pyridine hydrochloride, to produce intermediate product H represented by the following formula (h);

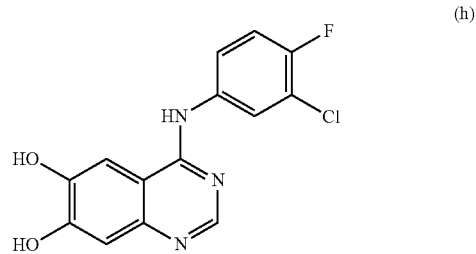 [SMILES: Oc1cc2ncnc(Nc3ccc(F)c(Cl)c3)c2cc1O]

(2) in the presence of the first organic solvent, allowing intermediate product H obtained in the step (1) to contact and react with halogenated fatty alcohol to obtain an intermediate product I represented by the following formula (i), and allowing the intermediate product I to undergo halogenation reaction, so as to obtain intermediate product J represented by the following formula (j), and then allowing intermediate product J to undergo ammonolysis reaction with ammonia, $X_1$ and $X_2$ are halogen atom;

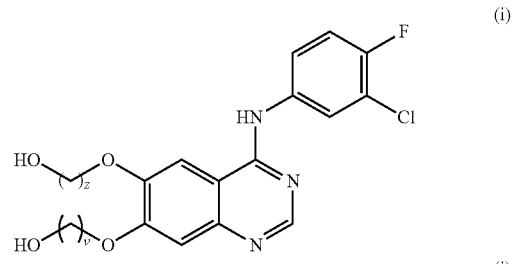

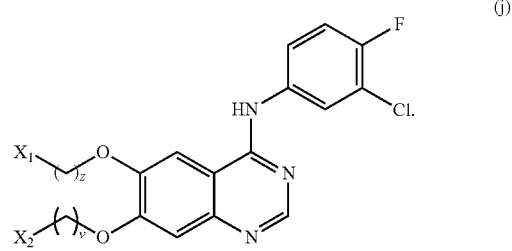

23. The preparation method according to claim 22, wherein in step (1), molar ratio of said first reactant A to molten pyridine hydrochloride is 1: (15-25); the conditions of allowing first reactant A to contact and react with molten pyridine hydrochloride include, the reaction temperature is 150-185° C., the reaction time is 2-5 hours.

24. The preparation method according to claim 22, wherein in step (2), the molar ratio of said intermediate product H obtained in step (1) to halogenated fatty alcohols is 1: (3-8); conditions of allowing said intermediate product H to contact and react with a halogenated fatty alcohol include that the reaction temperature is 40-60° C., the reaction time is 5-15 hours; said halogenated fatty alcohol is one or more selected from the group consisting of 2-haloethanol, 3-halogenated propanol and 4-halogenated butyl alcohol.

25. The preparation method according to claim 22, wherein in step (2), the performance of allowing intermediate product I to undergo halogenation reaction comprises contacting and reacting the intermediate D with the phosphorus trihalide in the presence of a fifth organic solvent, the molar ratio of intermediate D and phosphorus trihalide is 1: (1.2-2.5), the contact reaction conditions include that, the reaction temperature is 90-110° C., the reaction time is 1-10 hours; said fifth organic solvents is one or more selected from the group consisting of chlorobenzene, pyridine and N,N-dimethyl formamide, on the basis that the total amount of the intermediate product D and phosphorus trihalide is 1000 mg, amount of said fifth organic solvent used is 20-80 ml.

26. The preparation method according to claim 22, wherein in step (2), the performance to have ammonolysis between intermediate product J and ammonia comprises allowing intermediate product J to contact and react with ammonia in the presence of a sixth organic solvents, the molar ratio of intermediate product J to ammonia is 1: (10-30), the conditions of contact reaction include that, the reaction temperature is 25-50° C., and the reaction time is 5-15 hours; the sixth organic solvent is one or more selected from the group consisting of methanol, ethanol and isopropanol, on the basis that the amount of intermediate J is 1000 mg, amount of said sixth of the organic solvent used is 20-50 ml.

27. The preparation method according to claim 7, wherein, the preparation method of quinazoline complex as protein kinase inhibitor represented by general formula AG(X'Y')Z or [AG(XY)Z]$^+$B$^-$ comprises:
    allowing halogenated arene ruthenium dimer containing two A groups to contact with the chelating ligand containing two coordinating atoms in alcohol or aqueous alcohol solution, under conditions of allowing ruthenium in said halogenated arene ruthenium dimer to chelate and coordinate with two coordinating atoms in chelating ligand.

28. The preparation method according to claim 27, wherein the molar ratio of said halogenated arene ruthenium dimer containing two A groups to chelating ligand containing two coordinating atoms is 1: (1-3), the contacting temperature is 20-50° C., and contacting time is 0.5-2 hours; on the basis that the total amount of said halogenated ruthenium arene dimer containing two A groups and chelating ligand containing two coordinating atoms is 100 mg, the amount of said alcohol or aqueous alcohol solution used is 30-50 ml, and said alcohol is methanol.

29. The preparation method according to claim 27, wherein said chelating ligand containing two coordinating atoms is represented by general formula (1), wherein, m is 0, R' is hydrogen, R is fused heterocyclic imino or substituted fused heterocyclic imino represented by any one of general formulae (5)-(7), alternatively, R is any one of fused heterocyclic imino or substituted fused heterocyclic imino represented by the general formulae (2)-(4) and aminoalkyl imino represented by general formula (8) as well as six-membered aromatic heterocyclic imino or substituted six-membered aromatic heterocyclic imino represented by general formulae (11)-(13); alternatively, both R and R' are —NH$_2$; n is an integer from 1 to 3, m is an integer from 1 to 3.

30. The preparation method according to claim 27, further comprises a step of substituting halogen ion in reaction product from chelating and coordination between ruthenium in halogenated arene ruthenium dimer containing two A groups and two coordinating atoms in chelating ligand by one group selected from the group consisting of SCN, —N$_3$, —SCH$_3$, —SH, pyridyl, pyridyl which is substituted by one or several groups of alkyl with 1-3 carbon atoms, imidazolyl and imidazolyl which is substituted by one or several groups of alkyl with 1-3 carbon atoms.

31. The preparation method according to claim 30, wherein, performance of said substituting halogen ion in reaction product from chelating and coordination between ruthenium in halogenated arene ruthenium dimer containing two A groups and two coordinating atoms in chelating ligand comprises: in a ninth organic solvent, said reaction product is mixed with AgPF$_6$ or AgBF$_4$, then filtered, and the filtrate is mixed with any one selected from the group consisting of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms; the molar ratio of said any one selected from the group consisting of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms to said reaction product is 1-5:1; the filtrate is mixed with any one selected from the group consisting of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms at the temperature of 20-50° C. for 0.5-2 hours; on the basis that the total amount of any one selected from the group consisting of thiocyanate of alkali metal, azide of alkali metal, thiomethyl salt of alkali metal, sulfhydryl salt of alkali metal, saturated carboxylic acid with 1-3 carbon atoms, pyridine, pyridine substituted by one or several groups of alkyl with 1-3 carbon atoms, imidazole, and imidazole substituted by one or several groups of alkyl with 1-3 carbon atoms is 100 mg, the amount of said ninth organic solvent used is 30-50 mL; the said ninth organic solvent is methanol and/or ethanol.

32. The preparation method according to claim 7, wherein preparation method for protease inhibitor represented by general formula [AG(X1Y1)Z1]$^+$B$^-$ comprises:
    (1) making halogenated arene ruthenium dimer containing two A groups in contact with alkyl diamine with 1-5 carbon atoms in alcohol or aqueous alcohol solution, under conditions of allowing ruthenium in said halogenated arene ruthenium dimer containing two A groups to chelate and coordinate with two coordination nitrogen atoms in alkyl diamine;
    (2) step of substituting halogen ion in reaction product obtained from chelating and coordination between ruthenium in halogenated arene ruthenium dimer containing two A groups and two coordination nitrogen atoms in alkyl diamine with 1-5 carbon atoms with monodentate ligand containing a single coordinating atom.

33. The preparation method according to claim 32, wherein in step (1), the molar ratio of said halogenated arene ruthenium dimer containing two A groups to alkyl diamine with 1-5 carbon atoms is 1:1-3, and the contacting temperature is 20-50° C., the contacting time is 0.5-2 hours; on the basis that total amount of said halogenated arene ruthenium dimer containing two A groups and alkyl diamine with 1-5 carbon atoms is 100 mg, amount of said alcohol or aqueous alcohol solution used is 30-50 mL, said alcohol is methanol; in step (2), performance of said substituting halogen ion in reaction product obtained from chelating and coordination between ruthenium in halogenated arene ruthenium dimer containing two A groups and two coordination nitrogen atoms in alkyl diamine with 1-5 carbon atoms comprises: in the ninth organic solvent, said reaction product is mixed with $AgPF_6$ or $AgBF_4$, then filtered, and the filtrate is mixed with a monodentate ligand with a single coordinating atom; the molar ratio of said monodentate ligand with a single coordinating atom to said reaction product is 1-5:1, when the filtrate is mixed with a monodentate ligand with a single coordinating atom, the temperature is 20-50° C., the duration is 0.5-2 hours; on the basis that the total amount of said reaction product and monodentate ligand with a single coordinating atom is 100 mg, amount of said ninth solvent used may be 30-50 mL; said ninth organic solvent is methanol and/or ethanol.

34. The preparation method according to claim 32, wherein said monodentate ligand containing a single coordinating atom is represented by general formula (1), wherein, m is 0, R' is hydrogen, R is any one of group having on the ring a tertiary amino group and imidazole type five-membered heterocyclic structure and six-membered aromatic heterocyclic imino or substituted six-membered aromatic heterocyclic imino represented by general formula (10).

35. The preparation method according to claim 27, wherein A groups in said halogenated arene ruthenium dimer containing two A groups are selected from benzene, biphenyl, isopropyl toluene and benzo-cyclane.

36. The preparation method according to claim 7, wherein when M is ruthenium, the preparation method of the quinazoline complex as protease inhibitor represented by general formula G(M)W comprises:
  (1) in the presence of a tenth organic solvent, ruthenium halide and a mixture of aqueous hydrochloric acid and DMSO, or ruthenium halide and DMSO are heated to reflux, so as to obtain ruthenium compound coordinating with DMSO;
  (2) the ruthenium compound coordinating with DMSO obtained in step (1) is allowed to contact the quinazoline ligand containing a single or two coordinating atoms in alcohol or aqueous alcohol solution or hydrochloric acid solution of alcohol under the conditions of allowing ruthenium of ruthenium compound coordinating with DMSO to coordinate with single or two coordinating atoms in said ligand; and
  when M is platinum, the preparation method of the quinazoline complex as protease inhibitor represented by general formula G(M)W comprises allowing a dissolved platinum compound such as dipotassium tetrachloroplatinate in the presence of a eleventh organic solvent to contact the quinazoline ligand containing a single or two coordinating atoms under the conditions of allowing platinum compound coordinating with single or two coordinating atoms in said ligand.

37. The preparation method according to claim 36, wherein said chelating ligand containing two coordinating atoms is represented by general formula (1), wherein, m is 0, R' is hydrogen, R is any of fused heterocyclic imino or substituted fused heterocyclic imino represented by any of general formulae (2)-(7) and aminoalkyl imino represented by general formula (8); alternatively, both R and R' are —$NH_2$; n is an integer from 1 to 3, m is an integer from 1 to 3; said chelating ligand containing a single coordinating atom is represented by general formula (1), wherein, m is 0, R' is hydrogen, R is any one of group having on the ring a tertiary amino group and imidazole type five-membered heterocyclic structure represented by general formula (9) and six-membered aromatic heterocyclic imino or substituted six-membered aromatic heterocyclic imino represented by general formulae (10)-(13).

38. The preparation method according to claim 36, wherein in step (1), the temperature of said refluxing is 70° C. to 200° C., duration of said refluxing is 3-6 hours, the molar ratio of said ruthenium halide to chlorine hydride in aqueous hydrochloric acid is 1: (40-80), the molar ratio of said ruthenium halide to DMSO is 1: (40-80); said tenth organic solvent is one or more selected from methanol, ethanol, isopropanol; on the basis that the total amount of ruthenium halide, aqueous hydrochloric acid and DMSO is 2000 mg, the amount of said tenth organic solvent used is 30-50 mL; in step (2), the molar ratio of said ruthenium compound coordinating with DMSO to the quinazoline chelating ligand containing two coordinating atoms is 1:1-3, the contacting temperature is 20-50° C., and the contacting time is 0.5-6 hours; on the basis that the total amount of ruthenium compound coordinating with DMSO and chelating ligand containing two coordinating atoms is 100 mg, the amount of said alcohol or aqueous alcohol solution used is 3-10 ml; said alcohol is ethanol; alternatively, in step (2), the molar ratio of said ruthenium compound coordinating with DMSO to monodentate ligand containing a single coordinating atom is 1:1-3, contacting temperature is 20-50° C., the contacting time is 0.5-6 hours; on the basis that the total amount of ruthenium compound coordinating with DMSO and quinazoline derivative chelating ligand containing a single coordinating atom is 100 mg, the amount of said alcohol or hydrochloric acid solution of alcohol is 8-20 mL; said alcohol is ethanol.

* * * * *